United States Patent [19]
Janssen et al.

[11] Patent Number: 5,622,953
[45] Date of Patent: Apr. 22, 1997

[54] 1-AMINO-3-PHENOXY PROPANE DERIVATIVES AS MODULATOR AGENTS AND THEIR APPLICATIONS

[75] Inventors: Bernd Janssen, Ludwigshafen; Andreas Kling, Mannheim; Stefan Mueller, Speyer; Kurt Ritter, Heidelberg; Rainer Schlecker, Bissersheim, all of Germany; Gerhard Keilhauer, Marlboro; Cynthia Romerdahl, Wayland, both of Mass.; Ulrich Traugott, Mountain Lakes, N.J.

[73] Assignee: BASF Aktiengesellschaft, Ludwigshafen, Germany

[21] Appl. No.: 468,630

[22] Filed: Jun. 6, 1995

Related U.S. Application Data

[63] Continuation of Ser. No. 137,226, Oct. 18, 1993, abandoned, which is a continuation-in-part of Ser. No. 38,706, Mar. 29, 1993, abandoned.

[51] Int. Cl.$^6$ .................... A61K 31/495; A61K 31/445; C07D 241/04; C07D 401/10
[52] U.S. Cl. .................... 514/255; 514/317; 514/318; 514/326; 514/336; 544/359; 544/360; 544/369; 544/398; 546/194; 546/209; 546/277.4; 548/203; 548/235; 548/247; 548/452
[58] Field of Search ...................... 514/183, 212, 514/218, 255, 256, 277, 315, 317, 412; 540/484, 575; 544/215, 238, 239, 240, 241, 295, 296, 298, 333, 335, 353, 358, 360, 363, 370, 334; 546/139, 152, 153, 195; 548/152, 159, 217, 221, 241, 243, 400, 452, 525, 541

[56] References Cited

PUBLICATIONS

CA 96(25): 217826Y, 1982.

Chem. Pharm. Bull. 31(6), 2023–2032, 1983.

*Primary Examiner*—Yogendra N. Gupta
*Attorney, Agent, or Firm*—Keil & Weinkauf

[57] ABSTRACT

This invention relates to 1-amino-3-phenoxy-propane-derivatives of formula 1:

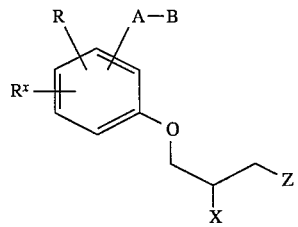

(in which A, B, R, $R^x$, X and Z are defined as in the specification described) and methods for their preparation.

These compounds may be used as modulators of multidrug resistance in cancer chemotherapy and for circumvention of resistance in the treatment of malaria.

4 Claims, No Drawings

1-AMINO-3-PHENOXY PROPANE DERIVATIVES AS MODULATOR AGENTS AND THEIR APPLICATIONS

This application is a continuation of application Ser. No. 08/137,226, filed on Oct. 18, 1993, now abandoned, which is a CIP of application Ser. No. 08/038,706, filed on Mar. 29, 1993, now abandoned.

BACKGROUND OF THE INVENTION

The development of resistance against chemotherapeutic agents is a major reason for the frequent failure in the clinical cancer therapy. Depending on the cancer cell-type, different molecular mechanisms counteract chemotherapeutic agents. The phrase Multi-Drug-Resistant (subsequently abbreviated as MDR) phenotype (S. Kuzmich et al., Med. Res. Rev. 1991, 11, 185) has been coined for a phenotype which has been selected for resistance to a single cytotoxic agent, but is found to exhibit cross-resistance to a variety of structurally and mechanistically unrelated compounds. The MDR-phenotype is observed upon treatment with vinca alkaloids, anthracyclines, and epipodophyllotoxins. A positive correlation exists between the MDR1-gene product P-glycoprotein of 170 KDalton molecular weight (subsequently abbreviated as P170) and the occurance of MDR (J. Bell, et al., Cancer Invest. 1991,9,563). P170 acts as an ATP-powered efflux-pump, which exports cytotoxic compounds from the endoplasm in a rather nonspecifc manner. In recent years, different classes of compounds were found to modulate MDR. Such compounds are: verapamil (E. Pommerenke et al., Arzneim.-Forsch. 1991, 41 (II), 855), niguldipine (A. Reymann et al., Arch.Pharmacol. 1991,343, Suppl. R50), cyclosporine A, and quinine (E. Solary et al., Cancer 1991, 68, 1714). As all of these compounds were developed for clinical applications other than MDR-modulation, they possess severe side effects (e.g. lowering blood pressure or suppression of the immune system). This makes it difficult to use the compounds as MDR-modulators in routine cancer therapy. Therefore, new modulators with reduced side effects or toxicity are required.

The present invention describes the preparation and use of 1-amino-3-phenoxy-propane-derivatives that are effective in modulating the resistance of tumor cells against chemotherapeutic agents like vincristine, vinblastine, adriamycine and etoposide.

SUMMARY OF THE INVENTION

The present invention provides novel 1-amino-3-phenoxy-propane-derivatives of formula 1:

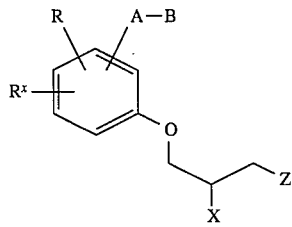

in which
X represents H, OH, $OCOR^1$, $OCOOR^1$, $OCONHR^1$, $OR^1$, $OSO_3-$, $OPO_3^{2-}$ wherein $R^1$ means linear or branched alkyl; hydroxyalkyl; aminoalkyl;

or phenyl, or pyridyl, both of which may be substituted by up to three substituents which may independently be selected from the group consisting of alkyl, alkoxy, halogen, nitro, $CF_3$, NR'R", wherein R' and R" are either hydrogen or linear or branched alkyl;

or phenylalkyl, wherein the alkyl moiety may be substituted by a hydroxy- or amino-group and the phenyl group may be substituted by up to three substituents which may independently be selected from the group consisting of linear or branched alkyl, alkoxy, halogen, nitro, $CF_3$, NR'R", wherein R' and R" are defined as above;

Z represents the aminoheterocycles:

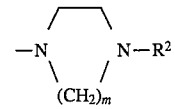

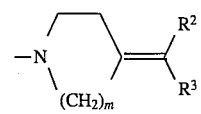

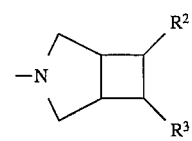

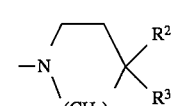

wherein
m is 2 or 3;

$R^2$ and $R^3$ independent from each other are hydrogen (provided that $R^2$ and $R^3$ are not hydrogen at the same time), cycloalkyl;

or phenyl, or phenylalkyl, or pyridyl, where the rings may be substituted by up to three substituents which are independently selected from the group consisting of linear or branched alkyl, alkoxy, alkylenedioxy, halogen, nitro, $CF_3$, NR'R", wherein R' and R" are as defined above;

or the residues:

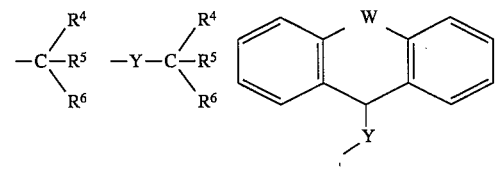

wherein
$R^4$ is hydrogen, hydroxy or cycloalkyl;
$R^5$ is hydrogen or cycloalkyl, and $R^6$ is cycloalkyl;
or $R^4$, $R^5$ and $R^6$ are independently selected from the group of phenyl, or phenylalkyl, or pyridyl, which all may be substituted by up to three substituents which may independently be selected from the groups consisting of linear or branched alkyl, alkoxy, alkylenedioxy, halogen, nitro, $CF_3$, NR'R", wherein R' and R" are as defined above;

Y means a carbonyl- or a $(CH_2)_n$-moiety, with n being 0, 1, 2 or 3,

W means oxygen, sulfur, a group represented by the formula $NR^{11}$ (wherein $R^{11}$ may be hydrogen or linear or branched alkyl), a carbonyl moiety, or one of the following moieties:
—O—(CH$_2$)$_q$—, —CH=CH—, —(CH$_2$)$_p$—, —NH—CH$_2$—, —N=CH—, —(C=O)—NR$^{1''}$, and with q being 0, 1 or 2 and p being 0, 1 or 2.

A represents the structures:

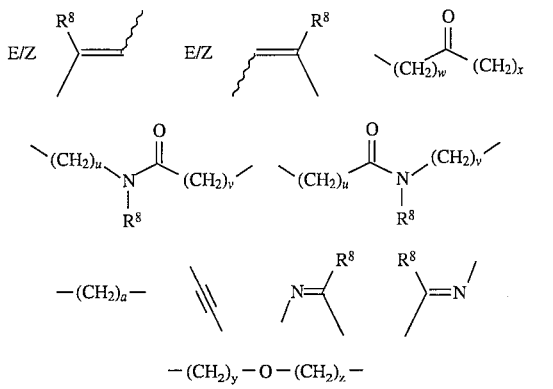

wherein R$^8$ means hydrogen, linear or branched alkyl, allyl, alkoxy, benzyl, or CF$_3$.

a is 1, 2, 3 or 4, u and v are 0, 1 or 2 (with the proviso that the sum of u and v is not larger than three), w and x are 0, 1 or 2 (with the proviso that the sum of w and x is not larger than three), y and z are independently from each other 0, 1 or 2.

B represents a ring system selected from the group consisiting of:

phenyl (with the proviso, that B is not phenyl, when A is —O—CH$_2$—), pyridyl, pyrimidyl, pyridazinyl, pyrazinyl, naphthyl, quinolinyl, isoquinolinyl, quinoxalinyl, quinazolinyl, cinnolinyl, indanyl, benzofuranyl, benzothienyl, benzoxazolyl, benzthiazolyl, benzisoxazolyl, benzisothiazolyl, naphthyridinyl, or cyclopentadienyl, which all may be substituted by up to three substituents selected from the group consisting of linear or branched alkyl, alkoxy, methoxyalkyl, trifluoromethoxyalkyl, carbonylalkoxy, CF$_3$, halogen, cyano, nitro, NR'R", wherein R' and R" are as defined above, alkyl-NR'R", wherein R' and R" are defined as above;

or 1,3,5-triazinyl, furanyl, thienyl, oxazolyl, isoxazolyl, thiazolyl, or isothiazolyl, which all may be substituted by up to two substituents selected from the group consisting of linear or branched alkyl, alkoxy, methoxyalkyl, trifluoromethoxyalkyl, carbonylalkoxy, CF$_3$, halogen, cyano, nitro, NR'R", wherein R' and R" are as defined above, alkyl-NR'R", wherein R' and R" are defined as above;

or indolyl, benzimidazolyl, pyrrolyl, imidazolyl, or pyrazolyl, which all may be substituted at carbon by up to three substituents selected from the group consisting of linear or branched alkyl, alkoxy, methoxyalkyl, trifluoromethoxyalkyl, carbonylalkoxy, CF$_3$, halogen, cyano, nitro, NR'R" or alkyl-NR'R", wherein R' and R" are as defined above, and which may be substituted at their nitrogen atoms by a substituent selected from a group consisting of linear or branched alkyl, phenylalkyl, acylalkyl, phenylacylalkyl, or phenylacyl;

or 1,2,3-triazolyl, or 1,2,4-triazolyl, which may be substituted at their carbon atoms by a substituent selected from the group consisting of linear or branched alkyl, alkoxy, methoxyalkyl, trifluoromethoxyalkyl, carbonylalkoxy, CF$_3$, halogen, cyano, nitro, NR'R" or alkyl-NR'R", wherein R' and R" are as defined above, phenyl, benzyl (wherein these two residues may independently be substituted by up to two substituents selected from halogen, alkyl, alkoxy, CF$_3$), and which may be substituted at their nitrogen atoms by a substituent selected from the group consisting of linear or branched alkyl, phenylalkyl, acylalkyl, phenylacylalkyl, or phenylacyl;

or 1,2,3-oxadiazolyl, 1,2,4-oxadiazolyl, 1,3,5-oxadiazolyl, 1,2,5-oxadiazolyl, 1,2,3-thiadiazolyl, 1,2,4-thiadiazolyl, 1,2,5-thiadiazolyl, or 1,3,5-thiadiazolyl, which may be substituted by a substituent selected from the group consisting of linear or branched alkyl, alkoxy, methoxyalkyl, trifluoromethoxyalkyl, carbonylalkoxy, CF$_3$, halogen, cyano, nitro, NR'R" or alkyl-NR'R", wherein R' and R" are as defined above, phenyl, benzyl (wherein these two residues may independently be substituted by up to two substituents selected from halogen, alkyl, alkoxy, CF$_3$);

or 1,2,3,4-oxatriazolyl, or 1,2,3,5-oxatriazolyl;

R and R$^x$ each mean a substituent selected independently from the group consisting of hydrogen, hydroxy, linear or branched alkyl, alkoxy, halogen, nitro, CF$_3$, NR'R", wherein R' and R" are as defined above, or a carbo- or heterocycle, annellated to the phenyl moiety of formula 1, thus forming a bicyclic ring system selected from the group consisting of naphthalene, tetrahydronaphthalene, tetramethyltetrahydronaphthalene, indene, indole, benzofurane, benzothiophene, benzimidazole, each of them optionally substituted at their carbon atoms by up to three substituents independently selected from the group consisting of linear or branched alkyl, alkoxy, nitro, CF$_3$, halogen, nitro, NR'R", wherein R' and R" are as defined above.

DETAILED DESCRIPTION AND PREFERRED EMBODIMENTS

It is to be understood that the compounds of formula 1 can contain various stereogenic centers and that all possible stereo- and regioisomers of foresaid compounds including all possible mixtures of isomers are covered by this claim. Enantiomerically pure material of compounds of formula 1 containing one or more stereogenic centers can be obtained by the following procedures: use of enantiomerically pure starting materials, fractional crystallisation of diastereoisomeric salts formed with optically active acids, chromatographic separation using a chiral stationary phase.

The 1-amino-3-phenoxy-propane-derivatives of formula 1 can be used as free bases or pharmaceutically suitable salts thereof. Preferred acids for the formation of salts are: hydrochloric acid, hydrobromic acid, sulfuric acid, phosphoric acid, methanesulfonic acid, 4-toluenesulfonic acid, fumaric acid, malic acid, oxalic acid, malonic acid, citric acid, tartaric acid, propionic acid, acetic acid, formic acid, benzoic acid and other physiologically tolerated acids (as described for example in J. Pharm. Sci., Vol 66, No. 1, p.1–17 (1977)).

As used herein, the terms used above have the following preferred meanings:

halogen means fluoro, chloro, bromo or iodo;

alkyl means a methyl-, ethyl-, propyl- or butyl-group, or their positional isomers;

NR'R" means an amino-, methylamino-, ethylamino-, propylamino-, isopropylamino-, butylamino-, tert.butylamino-, dimethylamino-, diethylamino-, methylethylamino-, dipropylamino-, diisopropylamino-group;

alkoxy means a methoxy-, ethoxy-, propoxy-, butoxy-group or their positional isomers;

hydroxyalkyl means a 2-hydroxyethyl-, 2-hydroxypropyl-, 2-hydroxybutyl-group;

aminoalkyl means a 1-aminomethyl-, 1-aminoethyl-, 1-amino-2-methyl-propyl-group;

phenylalkyl means a phenylmethyl-, 2-(phenyl)-ethyl, 3-(phenyl)-propyl-group or their positional isomers, which additionally may be substituted by up to three substituents which may be independently selected from the groups consisting of linear or branched alkyl (preferably $C_{1-4}$), hydroxy, alkoxy (preferably $C_{1-4}$), halogen, nitro, $CF_3$, NR'R'', wherein R' and R'' are as defined above;

alkylenedioxy means methylenedioxy, ethylenedioxy;

Z means a substituted aminoheterocycle such as piperazine, homopiperazine, piperidine, homopiperidine, or an annelated bicycle such as in 6- and/or 7-position substituted exo-3-azabicyclo-[3.2.0]-heptanes.

Examples of $R^2$ and $R^3$, which are part of Z, include the following groups: hydrogen (provided that $R^2$ and $R^3$ are not hydrogen at the same time); phenyl, 4-fluorophenyl, 4-chlorophenyl, 4-tert.butylphenyl, 4-methoxyphenyl, 4-trifluoromethylphenyl, 4-dimethylaminophenyl, 3-fluorophenyl, 3-chlorophenyl, 3-tert.butylphenyl, 3-methoxyphenyl, 3-trifluoromethylphenyl, 3-dimethylaminophenyl, 2-fluorophenyl, 2-chlorophenyl, 2-tert.butylphenyl, 2-methoxyphenyl, 2-trifluoromethylphenyl, 2-dimethylamino-phenyl, 3,4-dimethoxyphenyl, 2,3,4-trimethoxyphenyl, 3,4,5-trimethoxyphenyl, 3,4-methylenedioxyphenyl phenylmethyl, (4-fluorophenyl)-methyl, (4-chlorophenyl)-methyl, (4-tert.butylphenyl)-methyl, (4-methoxyphenyl)-methyl, (4-trifluoromethylphenyl)-methyl, (4-dimethylaminophenyl)-methyl, (3-fluorophenyl)-methyl, (3-chlorophenyl)-methyl, (3-tert.butylphenyl)-methyl, (3-methoxyphenyl)-methyl, (3-trifluoromethylphenyl)-methyl, (3-dimethylaminophenyl)-methyl, (2-fluorophenyl)-methyl, (2-chlorophenyl)-methyl, (2-tert.butylphenyl)-methyl, (2-methoxyphenyl)-methyl, (2-trifluoromethylphenyl)-methyl, (2-dimethylaminophenyl)-methyl, (3,4-dimethoxyphenyl)-methyl, (2,3,4-trimethoxyphenyl)-methyl, (3,4,5-trimethoxyphenyl)-methyl, (3,4-methylenedioxyphenyl)-methyl phenylethyl, (4-fluorophenyl)-ethyl, (4-chlorophenyl)-ethyl, (4-tert.butylphenyl)-ethyl, (4-methoxyphenyl)-ethyl, (4-trifluoroethylphenyl)-ethyl, (4-dimethylaminophenyl)-ethyl, (3-fluorophenyl)-ethyl, (3-chlorophenyl)-ethyl, (3-tert.butylphenyl)ethyl, (3-methoxyphenyl)-ethyl, (3-trifluoromethylphenyl)-ethyl, (3-dimethylaminophenyl)-ethyl, (2-fluorophenyl)-ethyl, (2-chlorophenyl)-ethyl, (2-tert.butylphenyl)-ethyl, (2-methoxyphenyl)-ethyl, (2-trifluoromethylphenyl)-ethyl, (2-dimethylaminophenyl)-ethyl, (3,4-dimethoxyphenyl)-ethyl, (2,3,4-trimethoxyphenyl)-ethyl, (3,4,5-trimethoxyphenyl)-ethyl, (3,4-methylenedioxyphenyl)-ethyl, (3,4-dimethoxyphenyl)-ethyl, (2,3,4-trimethoxyphenyl)-ethyl, 2-pyridyl, 3-pyridyl, 4-pyridyl, (2-pyridyl)-methyl, (3-pyridyl)-methyl, (4-pyridyl)-methyl, (2-pyridyl)-ethyl, (3-pyridyl)-ethyl, (4-pyridyl)-ethyl, diphenylmethyl, bis(4-fluorophenyl)-methyl, bis(4-chlorophenyl)-methyl, bis(4-tert.butylphenyl)-methyl, bis(4-methoxyphenyl)-methyl, bis(4-trifluoromethylphenyl)-methyl, bis(4-dimethylaminophenyl)-methyl, bis(3,4-dimethoxyphenyl)-methyl, bis(2,3,4-trimethoxyphenyl)-methyl, bis(3,4,5-trimethoxyphenyl)-methyl, bis(2-pyridyl)-methyl, bis(3-pyridyl)-methyl, bis(4-pyridyl)-methyl, 2,2-diphenylethyl, 2,2-bis(4-fluorophenyl)-ethyl, 2,2-bis(4-chlorophenyl)-ethyl, 2,2bis(4-tert.butylphenyl)-ethyl, 2,2-bis(4-methoxyphenyl)-ethyl, 2,2-bis(4-trifluoromethylphenyl)-ethyl, 2,2-bis(4-dimethylaminophenyl)-ethyl, 2,2-bis(3,4-dimethoxyphenyl)-ethyl, 2,2-bis(2,3,4-trimethoxyphenyl)-ethyl, 2,2-bis(3,4,5-trimethoxyphenyl)-ethyl, 2,2-bis(2-pyridyl)-ethyl, 2,2-bis(3-pyridyl)-ethyl, 2,2-bis(4-pyridyl)-ethyl, triphenylmethyl, phenyl-(2-pyridyl)-methyl, phenyl-(3-pyridyl)-methyl, phenyl-(4-pyridyl)-methyl, 2-phenyl-2-(2-pyridyl)-ethyl, 2-phenyl-2-(3-pyridyl)-ethyl, 2-phenyl-2-(4-pyridyl)-ethyl, cyclohexyl-phenyl-methyl, 2-cyclohexyl-2-phenyl-ethyl, cyclohexyl-(2-pyridyl)-methyl, cyclohexyl-(3-pyridyl)-methyl, cyclohexyl-(4-pyridyl)-methyl, 2-(cyclohexyl)-2-(2-pyridyl)-ethyl, 2-cyclohexyl-2-(3-pyridyl)-ethyl, 2-cyclohexyl-2-(4-pyridyl)-ethyl, 3,3-diphenylpropyl, 3,3,3-triphenylpropyl, phenylacetyl, 2-(4-fluorophenyl)-acetyl, 2-(4-chlorophenyl)-acetyl, 2-(4-tert.butylphenyl)-acetyl, 2-(4-methoxyphenyl)-acetyl, 2-(4-trifluoroacetylphenyl)-acetyl, 2-(4-dimethylamino-phenyl)-acetyl, 2-(3,4-dimethoxyphenyl)-acetyl, 2-(2,3,4-trimethoxyphenyl)-acetyl, 2-(2-pyridyl)-acetyl, 2-(3-pyridyl)-acetyl, 2-(4-pyridyl)-acetyl, 2,2-diphenylacetyl, 2,2-triphenylacetyl, 2,2-bis(4-fluorophenyl)-acetyl, 2,2-bis(4-chlorophenyl)-acetyl, 2,2-bis(4-tert.butylphenyl)-acetyl, 2,2-bis(4-methoxyphenyl)-acetyl, 2,2-bis(4-trifluoroethylphenyl)-acetyl, 2,2-bis(4-dimethylamino-phenyl)-acetyl, 2,2bis(3,4-dimethoxyphenyl)-acetyl, 2,2-bis(2,3,4-trimethoxyphenyl)-acetyl, 2,2-bis(2-pyridyl)-acetyl, 2,2-bis(3-pyridyl)-acetyl, 2,2-bis(4-pyridyl)-acetyl, 2-phenyl-2-(2-pyridyl)-acetyl, 2-phenyl-2-(3-pyridyl)-acetyl, 2-phenyl-2-(4-pyridyl)-acetyl, 2-cyclohexyl-2-phenyl-acetyl, 2-cyclohexyl-2-(2-pyridyl)-acetyl, 2-cyclohexyl-2-(3-pyridyl)-acetyl, 2-cyclohexyl-2-(4-pyridyl)-acetyl, 5-fluorenyl, 5-dibenzosuberanyl, 5-dibenzosuberenyl, 5-dibenzosuberanyliden, 5-dibenzosuberenyliden, 9,10-dihydroanthracenyl, 9-xanthenyl, 9-thioxanthenyl, 6,11-dihydrobenz[b,e]oxepin-11-yl, dibenzo[b,f]azepin-5-yl, 10,11-dihydrodibenzo[b,f]azepin-5-yl, fluorene-5-carbonyl, dibenzosuberone-5-carbonyl, dibenzosuberene-5-carbonyl, 9,10-dihydroanthracene-carbonyl, xanthene-9-carbonyl, 9-thioxanthencarbonyl, 6,11-dihydrobenz[b,e]oxepin-11-carbonyl, dibenzo[b,f]azepin-5-carbonyl, 10,11-dihydrodibenzo[b,f]azepin-5-carbon yl.

A means one of the following residues: (E)-vinylene, (Z)-vinylene, (E)-1-methyl-vinylene, (E)-1-ethyl-vinylene, (E)-1-propyl-vinylene, (E)-1-butyl-vinylene, (E)-1-isopropyl-vinylene, (E)-1-tert.butyl-vinylene, (Z)-1-methyl-vinylene, (Z)-1-ethyl-vinylene, (Z)-1-propyl-vinylene, (Z)-1-butyl-vinylene, (Z)-1-isopropyl-vinylene, (Z)-1-tert.butyl-vinylene, (E)-2-methyl-vinylene, (E)-2-ethyl-vinylene, (E)-2-propyl-vinylene, (E)-2-butyl-ethynyl, (E)-2-isopropyl-vinylene, (E)-2-tert.butyl-vinylene, (Z)-2-methyl-vinylene, (Z)-2-ethyl-vinylene, (Z)-2-propyl-vinylene, (Z)-2-butyl-vinylene, (Z)-2-isopropyl-vinylene, (Z)-2-tert.butyl-vinylene, (E)-1-trifluoromethyl-vinylene, (Z)-1-trifluoromethyl-vinylene; (E)-1-methoxy-vinylene, (E)-1-ethoxy-vinylene, (E)-1-propoxy-vinylene, (E)-1-butoxy-vinylene, (E)-1-isopropoxy-vinylene, (E)-1-tert.butoxy-vinylene, (E)-2-methoxy-vinylene, (E)-2-ethoxy-vinylene, (E)-2-propoxy-vinylene, (E)-2-butoxy-vinylene, (E)-2-isopropoxy-vinylene, (E)-2-tert.butoxy-vinylene, (Z)-1-methoxy-vinylene, (Z)-1-ethoxy-vinylene, (Z)-1-propoxy-vinylene, (Z)-1-butoxy-vinylene, (Z)-1-isopropoxy-vinylene, (Z)-1-tert.butoxy-vinylene, (Z)-2-methoxy-vinylene, (Z)-2-ethoxy-vinylene, (Z)-2-propoxy-vinylene, (Z)-2-butoxy-vinylene, (Z)-2-isopropoxy-vinylene, (Z)-2- tert.butoxy-vinylene; ethinylene; methylene, dimethylene, trimethylene, tetramethylene; carbonyl, carbonylmethylene, methylenecarbonyl, carbonyldimethylene, methylenecarbonylmethylene, dimethylenecarbonyl, carbonyltrimethylene, trimethylenecarbonyl, methylenecarbonyldimethyl, dimethylenecarbonylmethylene; oxy, oxymethylene, oxydimethylene, methyleneoxy, dimethyleneoxy, methyleneoxymethylene, methyleneoxydimethylene, dimethyleneoxymethylene, dimethyleneoxydimethylene; carbonylimino, methylenecarbonylimino, N-methyl-carbonylimino, N-methylmethylenecarbonylimino, iminocarbonyl, iminocarbonylmethylene, N-methyl-iminocarbonyl, N-methyl-iminomethylenecarbonyl, N-dimethylenecarbonylimino, N-ethyl-dimethylenecarbonylimino, N-ethyl-iminocarbonyl, N-ethyl-iminodimethylene, N-propyl-carbonylimino, N-propyl-dimethylenecarbonyl, N-propyl-iminocarbonyl, N-propyl-iminomethylencarbonyl, N-isopropyl-carbonylimino, N-isopropyl-methylenecarbonylimino, N-isopropyl-iminocarbonyl, N-isopropyl-iminomethylenecarbonyl, carbonyliminomethylen, dimethylenecarbonyliminomethylene, carbonyl-N-methyl-iminomethylene, carbonyl-N-ethyl-iminomethylene, carbonyl-N-propyl-iminomethylene, carbonyl-N-isopropyl-iminomethylene, dimethylene-carbonyl-N-methyl-iminomethylene, dimethylenecarbonyl-N-ethyl-iminomethylene, dimethylenecarbonyl-N-propyl-iminomethylene, dimethylenecarbonyl-N-isopropyl-iminomethyl; methylideneaza, azamethylidene, methylenmethylideneaza, dimethylenemethylideneaza, trimethylenemethylideneaza, (methyl)-methylideneaza, (isopropyl)-methylideneaza, (tert.butyl)-methylideneaza, (trifluoromethyl)-methylideneaza, azamethylidenmethylene, azamethylidenedimethylene, azamethylidenetrimethylene, aza-(methyl)-methylidene, aza-(tert.butyl)-methylidene, aza-(trifluoromethyl)methylidene, (methoxy)-methylideneaza, (ethoxy)-methylideneaza, (propoxy)methylideneaza, (butoxy)-methylideneaza, (isopropoxy)-methylideneaza, (tert.butoxy)-methylideneaza, aza-(methoxy)-methylidene, aza-(ethoxy)-methylidene, aza-(propoxy)-methylidene, aza-(butoxy)-methylidene, aza-(isopropoxy)-methylidene, aza-(tert.butoxy)-methylidene; cyclopropylene, 3-methyl-cyclopropylene, 3,3-dimethyl-cyclopropylene, 3-ethyl-cyclopropylene, 3-propyl-cyclopropylene, 3-butyl-cyclopropylene, 3-isopropyl-cyclopropylene, 3-tert.butyl-cyclopropylene, 3-fluoro-cyclopropylene, 3-chlorocyclopropylene, oxiranylene.

X means one of the following residues: hydrogen, hydroxy, methoxy, ethoxy, propoxy, butoxy, isopropoxy, tert.butoxy, phenoxy, benzyloxy, phenethoxy, formyloxy, acetyloxy, propionyloxy, 2-hydroxy-propionyloxy, 2-amino-acetyloxy, 2-amino-propionyloxy, 2-amino-3-methyl-propionyloxy, benzoyloxy, 2-pyridoyl, 3-pyridoyl, 4-pyridoyl, 2-phenyl-acetyloxy, 2-phenyl-acetyloxy, 2-hydroxy-2-phenyl-acetyloxy; methylaminocarbonyloxy, phenylaminocarbonyloxy.

R and $R^x$ each mean up to two residues which can independently be selected from the following groups: methyl, ethyl, n-propyl, butyl, isopropyl, tert.-butyl, trifluoromethyl methoxy, ethoxy, propoxy, butoxy, isopropoxy, tert.-butoxy, fluoro, chloro, bromo, nitro, amino, methylamino, ethylamino, propylamino, isopropylamino, butylamino, tert.butylamino, dimethylamino, diethylamino, methylethylamino, dipropylamino, diisopropylamino;

or R and $R^x$ together with the phenyl residue they are attached to form a bicyclic ring system selected from the group consisting of: naphtalene, tetrahydronaphtalene, tetramethyltetrahydronaphtalene, indene, indole, benzofurane, benzothiophene, benzimidazole.

Examples for B include structures such as:

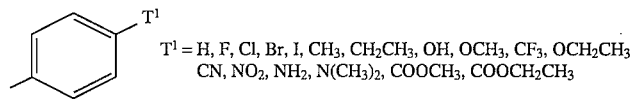

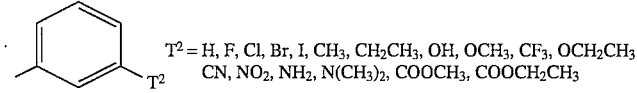

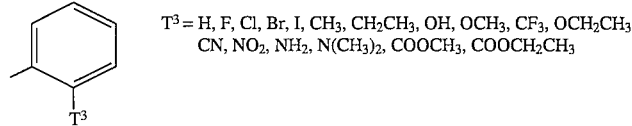

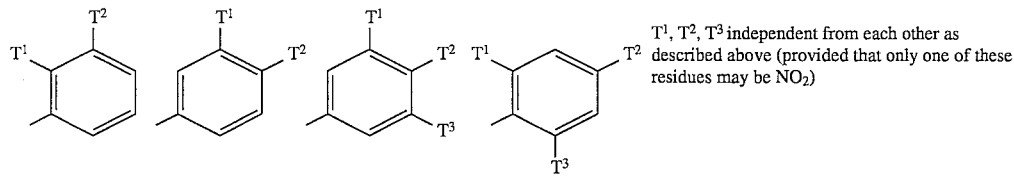

$T^1$, $T^2$, $T^3$ independent from each other as described above (provided that only one of these residues may be $NO_2$)

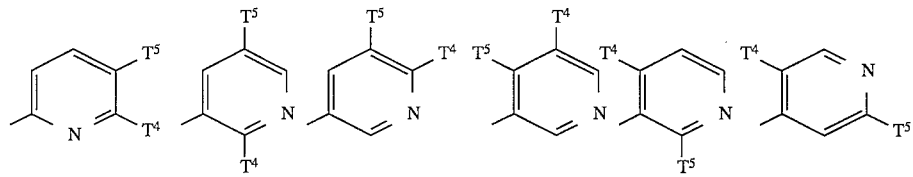

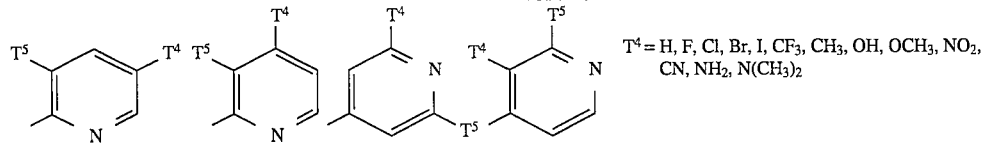
T⁴ = H, F, Cl, Br, I, CF₃, CH₃, OH, OCH₃, NO₂, CN, NH₂, N(CH₃)₂
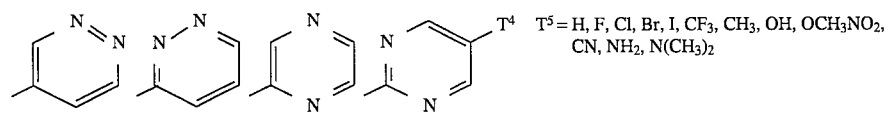
T⁵ = H, F, Cl, Br, I, CF₃, CH₃, OH, OCH₃ NO₂, CN, NH₂, N(CH₃)₂
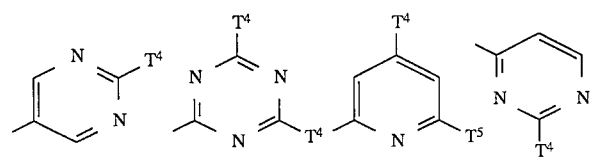
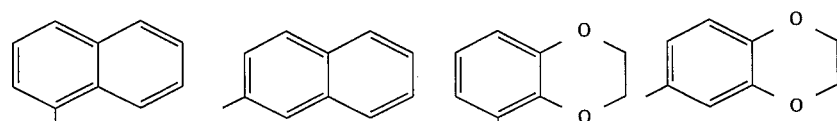
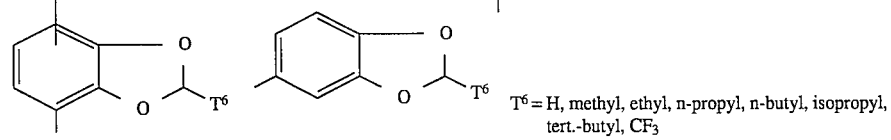
T⁶ = H, methyl, ethyl, n-propyl, n-butyl, isopropyl, tert.-butyl, CF₃
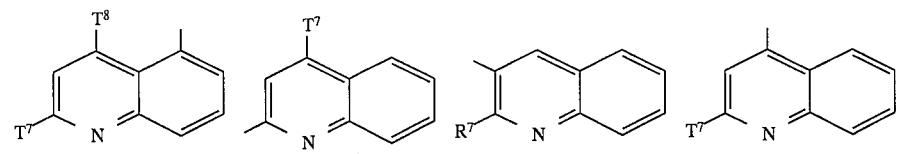
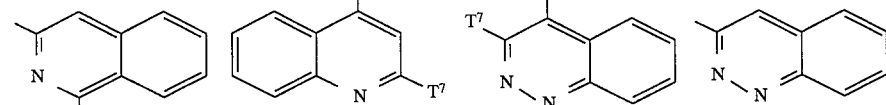
T⁷ = H, methyl, ethyl, n-propyl, n-butyl, isopropyl, tert.-butyl, CF₃
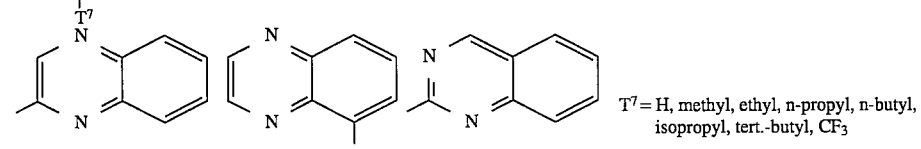
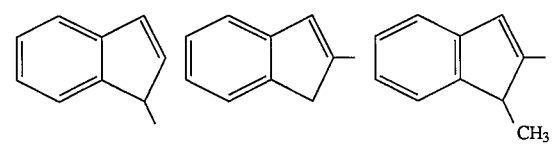
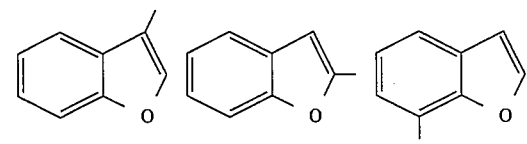
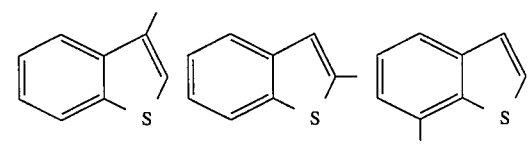

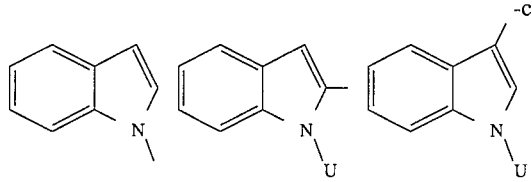
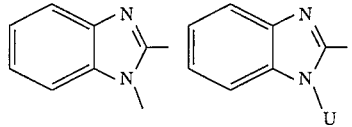
U = H, CH₃, C₂H₅, formyl, acetyl, phenyl, benzyl
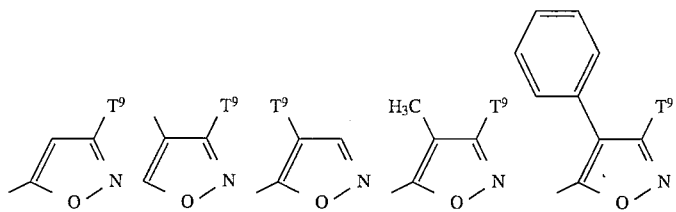
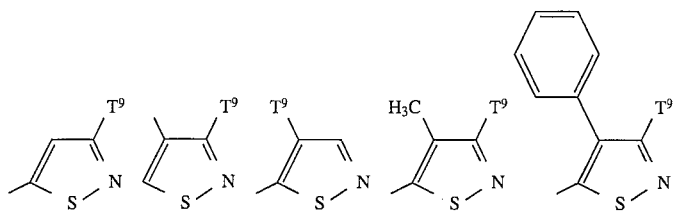
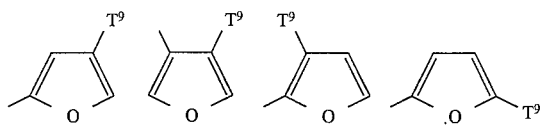
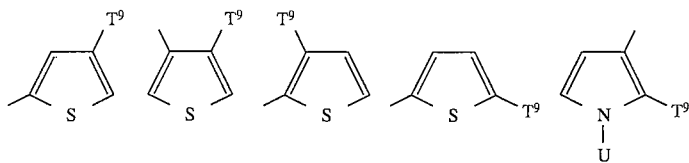
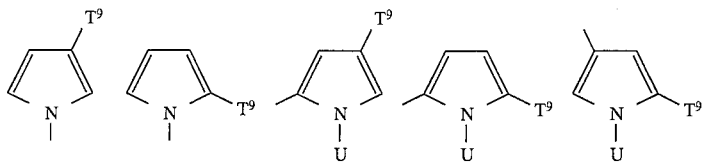
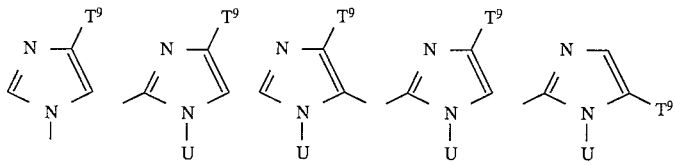
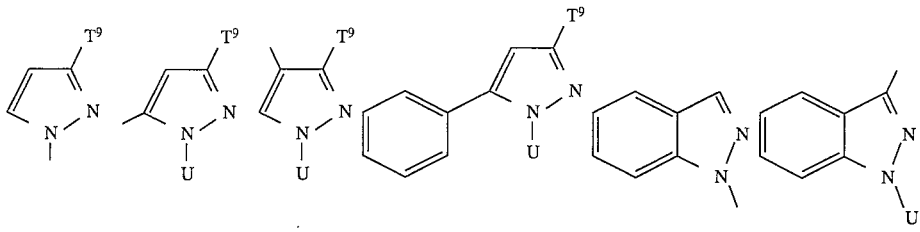

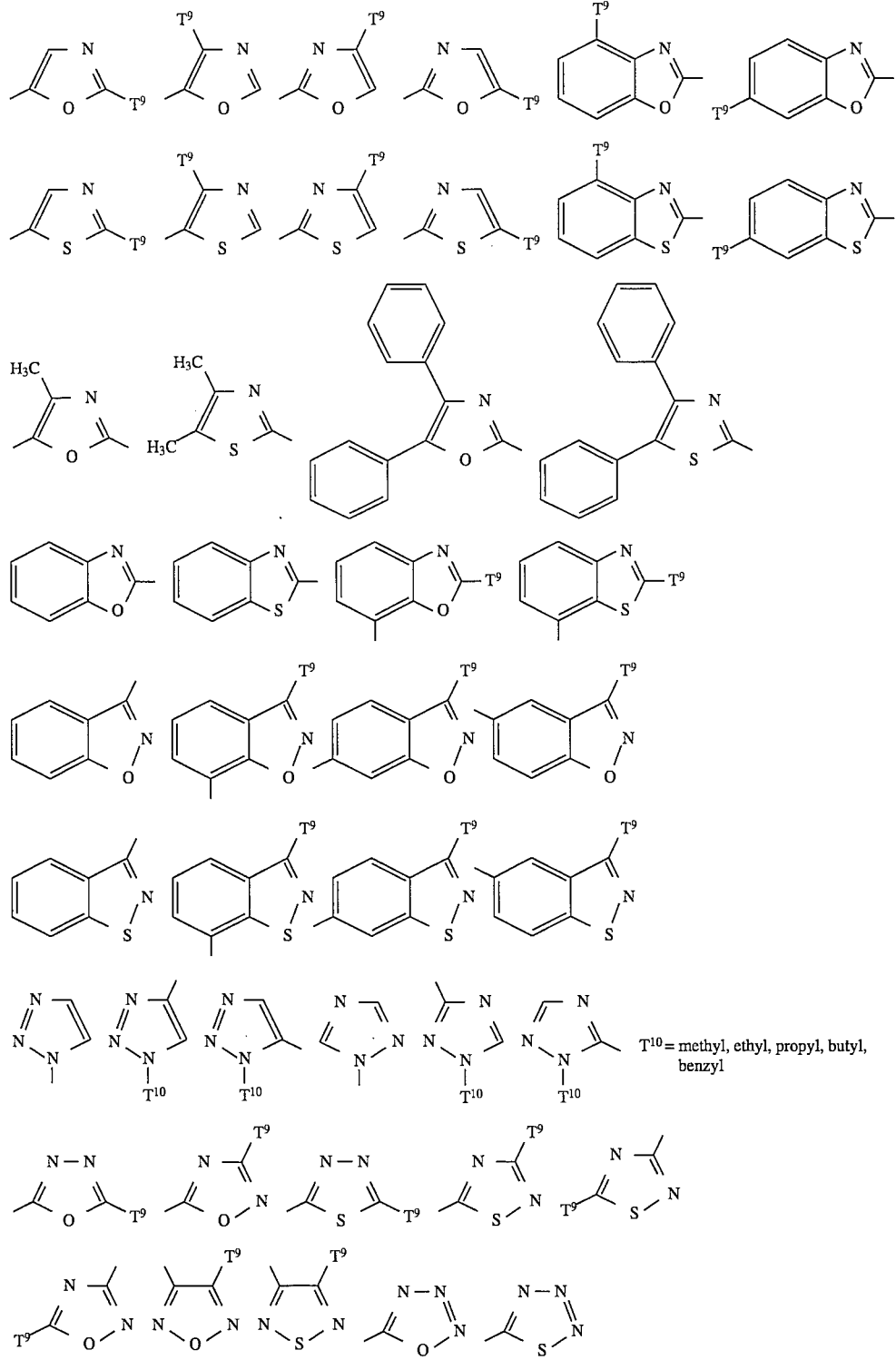
T9 for all mentioned residues =
H, F, Cl, Br, I, methyl, ethyl, n-propyl, n-butyl, isopropyl, tert.butyl,
CF3, OCH3, NO2, COOCH3, COOCH2CH3
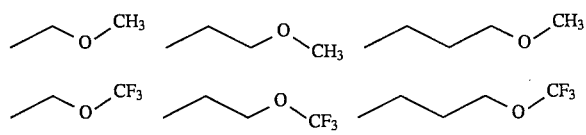

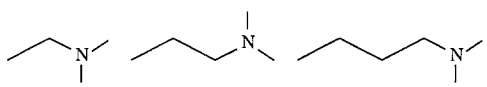

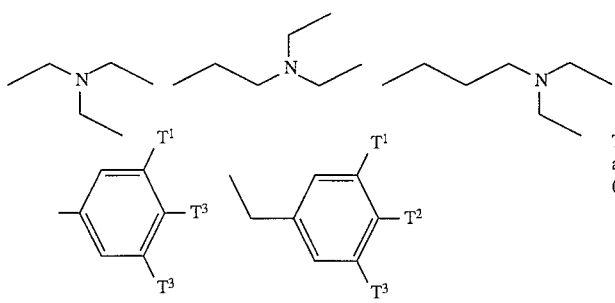

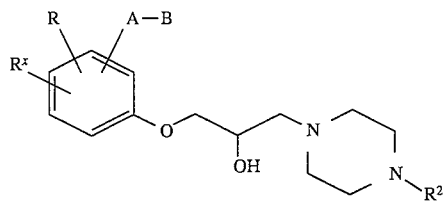

$T^1$, $T^2$, $T^3$ independent from each other as described above
(provided that only one of these residues is $NO_2$)

Specific examples of formula 1 include the following structures, classified according to the type of amino heterocycle Z: (the indication of listed compounds and examples with roman numbers, e.g. III, refer to the classification of compounds shown in the reaction schemes III to VIII):

Specific examples of type III with Z=Z–1 includes:

| Example No. | $R^2$ | A | B | R | $R^x$ |
|---|---|---|---|---|---|
| III-1 | dibenzosuberane-5-yl | 2-E-vinylene | 3-methoxymethyl-isoxazol-5-yl | H | H |
| III-2 | bis(4-methoxyphenyl)-methyl | 2-E-vinylene | 3-methoxymethyl-isoxazol-5-yl | H | H |
| III-3 | diphenyl-methyl | 4-E-vinylene | 3-methoxymethyl-isoxazol-5-yl | H | H |
| III-4 | dibenzosuberane-5-yl | 4-E-vinylene | 3-methoxymethyl-isoxazol-5-yl | H | H |
| III-5 | dibenzosuberane-5-yl | 2-E-vinylene | 3-methyl-isoxazol-5-yl | H | H |
| III-6 | diphenyl-methyl | 2-E-vinylene | 3-methyl-isoxazol-5-yl | H | H |
| III-7 | dibenzosuberane-5-yl | 2-E-vinylene | 3-ethoxy-carboxy-isoxazol-5-yl | H | H |
| III-8 | diphenyl-methyl | 2-E-vinylene | 3-ethoxy-carboxy-isoxazol-5-yl | H | H |
| III-9 | dibenzosuberane-5-yl | 3-E-vinylene | 3-methoxymethyl-isoxazol-5-yl | H | H |
| III-10 | diphenyl-methyl | 3-E-vinylene | 3-ethoxy-carboxy-isoxazol-5-yl | H | H |
| III-11 | dibenzosuberane-5-yl | 2-E-vinylene | 3-isopropyl-isoxazol-5-yl | H | H |
| III-12 | diphenyl-methyl | 2-E-vinylene | 3-phenyl-isoxazol-5-yl | H | H |
| III-13 | dibenzosuberane-5-yl | 2-E-vinylene | 3-phenyl-isoxazol-5-yl | H | H |
| III-14 | bis(4-fluorophenyl)-methyl | 2-E-vinylene | 3-methoxymethyl-isoxazol-5-yl- | H | H |
| III-15 | cyclohexyl-phenyl-methyl | 2-Z-vinylene | 3-isopropyl-isoxazol-5-yl | H | H |
| III-16 | diphenylacetyl | 2-Z-vinylene | 3-isopropyl-isoxazol-5-yl | H | H |
| III-17 | dibenzosuberane-5-yl | 2-E-vinylene | 3-methoxymethyl-isoxazol-5-yl | 4,5-(2,5-dimethyl-hexa-2,5-diyl) | |
| III-18 | dibenzosuberane-5-yl | 2-Z-vinylene | 3-methoxymethyl-isoxazol-5-yl | H | H |
| III-19 | diphenyl-methyl | 2-Z-vinylene | 3-methoxymethyl-isoxazol-5-yl | H | H |
| III-20 | dibenzosuberene-5-yl | 2-E-vinylene | 3-methoxymethyl-isoxazol-5-yl | H | H |
| III-21 | cyclohexyl-phenyl-acetyl | 3-E-vinylene | 3-methoxymethyl-isoxazol-5-yl | H | H |
| III-22 | cyclohexyl-phenyl-methyl | 2-E-vinylene | 3-methoxymethyl-isoxazol-5-yl | H | H |
| III-23 | cyclohexyl-phenyl-methyl | 2-E-vinylene | 3-phenyl-isoxazol-5-yl | H | H |
| III-24 | diphenyl-methyl | 2-E-vinylene | 3-methoxymethyl-isoxazol-5-yl | H | H |
| III-25 | diphenyl-methyl | 2-E-vinylene | 3-methoxymethyl-isoxazol-5-yl | 4,5-dimethoxy | |
| III-26 | diphenyl-methyl | 2-E-vinylene | 3-methoxymethyl-isoxazol-5-yl | 5-diethyl-amino | H |
| III-27 | dibenzosuberane-5-yl | 2-E-vinylene | 3-methoxymethyl-isoxazol-5-yl | 4,5-dimethoxy | |
| III-28 | dibenzosuberane-5-yl | 2-E-vinylene | 3-methoxymethyl-isoxazol-5-yl | 5-diethyl-amino | H |
| III-29 | cyclohexyl-phenyl-methyl | 2-E-vinylene | 3-methoxymethyl-isoxazol-5-yl | 4,5-dimethoxy | |
| III-30 | cyclohexyl-phenyl-methyl | 2-E-vinylene | 3-methoxymethyl-isoxazol-5-yl | 5-diethyl-amino | H |
| III-31 | diphenyl-acetyl | 2-E-vinylene | 3-methoxymethyl-isoxazol-5-yl | 4,5-dimethoxy | |
| III-32 | diphenyl-acetyl | 2-E-vinylene | 3-methoxymethyl-isoxazol-5-yl | H | H |

-continued

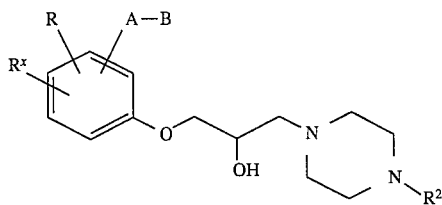

| Example No. | R² | A | B | R | Rˣ |
|---|---|---|---|---|---|
| III-33 | dibenzosuberane-5-yl | 2-E-vinylene | 3-methoxymethyl-isoxazol-5-yl | 4,5 buta-1,3-dien-1,4-diyl | |
| III-34 | dibenzosuberane-5-yl | 2-E-vinylene | 3-methoxymethyl-isoxazol-5-yl | 4-chloro | H |
| III-35 | diphenyl-methyl | 2-E-vinylene | 3-isopropyl-isoxazol-5-yl | H | H |
| III-36 | diphenyl-methyl | 2-E-vinylene | 3-methyl-isoxazol-5-yl | H | H |
| III-37 | diphenyl-methyl | 2-E-vinylene | 2-(4-methoxyphenyl)-oxazol-4-yl | H | H |
| III-38 | dibenzosuberane-5-yl | 2-E-vinylene | 2-(4-methoxyphenyl)-oxazol-4-yl | H | H |
| III-39 | dibenzosuberane-5-yl | 2-E-vinylene | 5-(4-methylphenyl)-1,3,4-oxdiazol-2-yl | H | H |
| III-40 | diphenyl-methyl | 2-E-vinylene | 5-(4-methylphenyl)-1,3,4-oxdiazol-2-yl | H | H |
| III-41 | diphenyl-methyl | 2-E-vinylene | N-methyl-pyrazol-4-yl | H | H |
| III-42 | diphenyl-methyl | 2-E-vinylene | 3,5-dimethyl-isoxazol-4-yl | H | H |
| III-43 | dibenzosuberane-5-yl | 2-E-vinylene | 3,5-dimethyl-isoxazol-4-yl | H | H |
| III-44 | bis-(4-fluorophenyl)-methyl | 2-E-vinylene | 3,5-dimethyl-isoxazol-4-yl | H | H |
| III-45 | diphenyl-methyl | 2-E-vinylene | 2-methoxymethyl-thiazol-4-yl | H | H |
| III-46 | dibenzosuberane-5-yl | 2-E-vinylene | 2-methoxymethyl-thiazol-4-yl | H | H |
| III-47 | bis(4-fluorophenyl)-methyl | 2-E-vinylene | 2-methoxymethyl-thiazol-4-yl | H | H |
| III-48 | diphenyl-methyl | 2-E-vinylene | thiophen-2-yl | H | H |
| III-49 | diphenyl-methyl | 2-E-vinylene | thiophen-3-yl | H | H |
| III-50 | diphenyl-methyl | 2-E-vinylene | 5-methyl-1,3,4-thiadiazol-2-yl | H | H |
| III-51 | 2-(3,4-dimethoxyphenyl)-ethyl | 2-E-vinylene | 3-methoxymethyl-isoxazol-5-yl | H | H |
| III-52 | dibenzosuberane-5-yl | 2-E-vinylene | 3-methoxymethyl-isoxazol-5-yl | 4-nitro | H |
| III-53 | diphenyl-methyl | 2-E-vinylene | 3-methoxymethyl-isoxazol-5-yl | 4-nitro | H |
| III-54 | diphenyl-methyl | 2-E-vinylene | 5-methoxymethyl-isoxazol-3-yl | H | H |
| III-55 | dibenzosuberane-5-yl | 2-E-vinylene | 5-methoxymethyl-isoxazol-3-yl | H | H |
| III-56 | bis(4-methoxyphenyl)-methyl | 2-E-vinylene | 2-methoxymethyl-thiazol-4-yl | H | H |
| III-57 | cyclohexyl-phenyl-methyl | 2-E-vinylene | pyridin-3-yl | H | H |
| III-58 | cyclohexyl-phenyl-methyl | 2-E-vinylene | pyridin-2-yl | H | H |
| III-59 | dibenzosuberene-5-yl | 2-Z-vinylene | 3-methoxymethyl-isoxazol-5-yl | H | H |
| III-60 | dibenzosuberane-5-yl | 2-Z-vinylene | 3-methyl-isoxazol-5-y | H | H |
| III-61 | dibenzosuberane-5-yl | 2-Z-vinylene | 3-isopropyl-isoxazol-5-yl | H | H |
| III-62 | dibenzosuberane-5-yl | 2-Z-vinylene | 3-phenyl-isoxazol-5-yl | H | H |
| III-63 | dibenzosuberane-5-yl | 2-Z-vinylene | 3-ethoxycarboxy-isoxazol-5-yl | H | H |
| III-64 | dibenzosuberane-5-yl | 2-Z-vinylene | thiophen-2-yl | H | H |

| Example No. | R² | A | B | R=Rˣ |
|---|---|---|---|---|
| III-65 | dibenzosuberane-5-yl | 2-Z-vinylene | thiophen-3-yl | H |
| III-66 | dibenzosuberane-5-yl | 2-Z-vinylene | pyridin-2-yl | H |
| III-67 | dibenzosuberane-5-yl | 2-Z-vinylene | pyridin-3-yl | H |
| III-68 | dibenzosuberane-5-yl | 2-Z-vinylene | pyridin-4-yl | H |
| III-69 | dibenzosuberane-5-yl | 2-Z-vinylene | pyrazol-2-yl | H |
| III-70 | dibenzosuberane-5-yl | 2-Z-vinylene | pyrazol-3-yl | H |
| III-71 | dibenzosuberane-5-yl | 2-Z-vinylene | N-methyl-pyrazol-3-yl | H |
| III-72 | dibenzosuberane-5-yl | 2-Z-vinylene | furan-2-yl | H |
| III-73 | dibenzosuberane-5-yl | 2-Z-vinylene | furan-3-yl | H |
| III-74 | dibenzosuberene-5-y | 2-Z-vinylene | 3-methyl-isoxazol-5-yl | H |
| III-75 | dibenzosuberene-5-yl | 2-Z-vinylene | 3-isopropyl-isoxazol-5-yl | H |
| III-76 | dibenzosuberene-5-yl | 2-Z-vinylene | 3-phenyl-isoxazol-5-yl | H |
| III-77 | dibenzosuberene-5-yl | 2-Z-vinylene | 3-ethoxycarboxy-isoxazol-5-yl | H |
| III-78 | dibenzosuberene-5-yl | 2-Z-vinylene | thiophen-2-yl | H |
| III-79 | dibenzosuberene-5-yl | 2-Z-vinylene | thiophen-3-yl | H |
| III-80 | dibenzosuberene-5-y | 2-Z-vinylene | pyridin-2-yl | H |
| III-81 | dibenzosuberene-5-yl | 2-Z-vinylene | pyridin-3-y | H |
| III-82 | dibenzosuberene-5-yl | 2-Z-vinylene | pyridin-4-yl | H |
| III-83 | dibenzosuberene-5-yl | 2-Z-vinylene | pyrazol-2-yl | H |
| III-84 | dibenzosuberene-5-yl | 2-Z-vinylene | pyrazol-3-yl | H |
| III-85 | dibenzosuberene-5-yl | 2-Z-vinylene | N-methyl-pyrazol-2-yl | H |
| III-86 | dibenzosuberene-5-yl | 2-Z-vinylene | N-methyl-pyrazol-3-yl | H |
| III-87 | dibenzosuberene-5-yl | 2-Z-vinylene | furan-2-yl | H |
| III-88 | dibenzosuberene-5-yl | 2-Z-vinylene | furan-3-yl | H |
| III-89 | diphenyl-methyl | 2-Z-vinylene | 3-methoxymethyl-isoxazol-5-yl | H |
| III-90 | diphenyl-methyl | 2-Z-vinylene | 3-methyl-isoxazol-5-yl | H |
| III-91 | diphenyl-methyl | 2-Z-vinylene | 3-isopropyl-isoxazol-5-yl | H |
| III-92 | diphenyl-methyl | 2-Z-vinylene | 3-phenyl-isoxazol-5-yl | H |
| III-93 | diphenyl-methyl | 2-Z-vinylene | 3-ethoxycarboxy-isoxazol-5-yl | H |
| III-94 | diphenyl-methyl | 2-Z-vinylene | thiophen-2-yl | H |
| III-95 | diphenyl-methyl | 2-Z-vinylene | thiophen-3-yl | H |

-continued

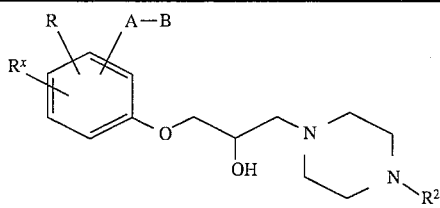

| Example No. | R² | A | B | R | Rˣ |
|---|---|---|---|---|---|
| III-96 | diphenyl-methyl | 2-Z-vinylene | pyridin-2-yl | | H |
| III-97 | diphenyl-methyl | 2-Z-vinylene | pyridin-3-yl | | H |
| III-98 | diphenyl-methyl | 2-Z-vinylene | pyridin-4-yl | | H |
| III-99 | diphenyl-methyl | 2-Z-vinylene | pyrazol-2-yl | | H |
| III-100 | diphenyl-methyl | 2-Z-vinylene | pyrazol-3-yl | | H |
| III-101 | diphenyl-methyl | 2-Z-vinylene | N-methyl-pyrazol-2-yl | | H |
| III-102 | diphenyl-methyl | 2-Z-vinylene | N-methyl-pyrazol-3-yl | | H |
| III-103 | diphenyl-methyl | 2-Z-vinylene | furan-2-yl | | H |
| III-104 | diphenyl-methyl | 2-Z-vinylene | furan-3-yl | | H |
| III-105 | diphenyl-methyl | 2-Z-vinylene | pyrrol-2-yl | | H |
| III-106 | cyclohexyl-phenyl-methyl | 2-E-vinylene | pyridin-4-yl | | H |
| III-107 | cyclohexyl-phenyl-methyl | 2-E-vinylene | N-methyl-pyrrol-2-yl | | H |
| III-108 | diphenyl-methyl | 2-E-vinylene | N-methyl-pyrrol-2-yl | | H |
| III-109 | diphenyl-methyl | 2-E-vinylene | pyridin-4-yl | | H |
| III-110 | diphenyl-methyl | 2-E-vinylene | pyridin-3-yl | | H |
| Example No. | R² | A | B | R | Rˣ |
| III-111 | diphenyl-methyl | 2-E-vinylene | pyridin-2-yl | H | H |
| III-112 | (9H)-xanthen-9-yl-carboxy | 2-E-vinylene | 3-methoxymethyl-isoxazol-5-yl | H | H |
| III-113 | cyclohexyl-phenyl-acetyl | 2-E-vinylene | 3-methoxymethyl-isoxazol-5-yl | H | H |
| III-114 | dibenzosuberane-5-yl | 2-E-vinylene | 3-methoxymethyl-isoxazol-5-yl | 6-fluroro | H |
| III-115 | diphenyl-methyl | 2-E-vinylene | 3-methoxymethyl-isoxazol-5-yl | 6-fluoro | H |
| III-116 | dibenzosuberane-5-yl | 2-E-vinylene | 4-dimethyl-1,3-oxazolin-3-yl | H | H |
| III-117 | diphenyl-methyl | 2-E-vinylene | 4-dimethyl-1,3-oxazolin-3-yl | H | H |
| III-142 | dibenzosuberane-5-yl | 2-Z-vinylene | 3-trifluormethyl-isoxazol-5-yl | H | H |
| III-143 | diphenyl-methyl | 2-E-vinylene | 3-trifluormethyl-isoxazol-5-yl | H | H |
| III-144 | dibenzosuberane-5-yl | 2-E-vinylene | 3-trifluormethyl-isoxazol-5-yl | H | H |
| III-145 | bis(4-fluorophenyl)methyl | 2-E-vinylene | 3-isopropyl-isoxazol-5-yl | H | H |
| III-146 | diphenyl-acetyl | 2-E-vinylene | 3-isopropyl-isoxazol-5-yl | H | H |
| III-147 | dibenzosuberane-5-yl | 2-E-vinylene | 3-methox-isoxazol-5-yl | H | H |
| III-148 | dibenzosuberane-5-yl | 2-Z-vinylene | 3-methoxy-isoxazol-5-yl | H | H |
| III-149 | diphenyl-methyl | 2-E-vinylene | 3-methoxy-isoxazol-5-yl | H | H |
| III-150 | diphenyl-methyl | 2-Z-vinylene | 3-methoxy-isoxazol-5-yl | H | H |
| III-155 | diphenyl-acetyl | 2-E-vinylene | 3-trifluoromethyl-isoxazol-5-yl | H | H |
| III-156 | bis(4-fluorophenyl)methyl | 2-E-vinylene | 3-trifluoromethyl-isoxazol-5-yl | H | H |
| III-157 | diphenylacetyl | 2-E-vinylene | 2-methoxymethyl-thiazol-4-yl | H | H |
| III-158 | dibenzosuberane-5-yl | 2-E-vinylene | 2-methoxymethyl-1,3,4-thiadiazol-5-yl | H | H |
| III-159 | diphenyl-methyl | 2-E-vinylene | 2-methoxymethyl-1,3,4-thiadiazol-5-yl | H | H |
| III-160 | diphenyl-acetyl | 2-E-vinylene | 2-methoxymethyl-1,3,4-thiadiazol-5-yl | H | H |
| III-161 | dibenzosuberane-5-yl | 2-Z-vinylene | 2-methoxymethyl-1,3,4-thiadiazol-5-yl | H | H |
| III-162 | bis(4-fluorophenyl)-methyl | 2-E-vinylene | 2-methoxymethyl-1,3,4-thiadiazol-5-yl | H | H |
| III-163 | cyclohexyl-phenyl-acetyl | 2-E-vinylene | 2-methoxymethyl-1,3,4-thiadiazol-5-yl | H | H |

Specific examples of type III with Z=Z–2 include:

| Example No. | R² = R³ | A | B | R | Rˣ |
|---|---|---|---|---|---|
| III-118 | phenyl | 2-E-vinylene | 3-methoxymethyl-isoxazol-5-yl | H | H |
| III-119 | phenyl | 4-E-vinylene | 3-methoxymethyl-isoxazol-5-yl | H | H |
| III-120 | phenyl | 2-E-vinylene | 3-methyl-isoxazol-5-yl | H | H |
| III-121 | phenyl | 2-E-vinylene | 3-ethoxycarboxy-isoxazol-5-yl | H | H |
| III-122 | phenyl | 3-E-vinylene | 3-methoxymethyl-isoxazol-5-yl | H | H |
| III-123 | phenyl | 2-E-vinylene | 3-isopropyl-isoxazol-5-yl | H | H |
| III-124 | phenyl | 2-E-vinylene | 3-phenyl-isoxazol-5-yl | H | H |
| III-125 | phenyl | 2-Z-vinylene | 3-methoxymethyl-isoxazol-5-yl | H | H |
| III-126 | phenyl | 3-Z-vinylene | 3-methoxymethyl-isoxazol-5-yl | H | H |
| III-127 | phenyl | 2-E-vinylene | 3-methoxymethyl-isoxazol-5-yl | 5-diethylamino | H |
| III-128 | phenyl | 2-E-vinylene | 3-methoxymethyl-isoxazol-5-yl | 4,5-dimethoxy | |
| III-129 | phenyl | 2-E-vinylene | 3,5-dimethyl-isoxazol-4-yl | H | H |
| III-130 | phenyl | 2-E-vinylene | 3-methoxymethyl-isoxazol-5-yl | 4-nitro | H |
| III-131 | phenyl | 2-E-vinylene | 3-methoxymethyl-isoxazol-5-yl | 6-fluoro | H |
| III-132 | phenyl | 2-E-vinylene | 4-dimethyl-1,3-oxazolin-2-yl | H | H |
| III-151 | phenyl | 2-E-vinylene | 5-methoxymethyl-isoxazol-3-yl | H | H |
| III-152 | phenyl | 2-E-vinylene | 3,5-dimethyl-isoxazol-4-yl | H | H |
| III-162 | phenyl | 2-E-vinylene | trifluoromethyl-isoxazol-5-yl | H | H |
| III-163 | phenyl | 2-E-vinylene | 2-methoxymethyl-thiazol-4-yl | H | H |
| III-164 | phenyl | 2-E-vinylene | 2-methoxymethyl-1,3,4-thiadiazol-5-yl | H | H |

Specific examples of type III with Z=Z–1 include:

| Example No. | R² | A | B | R = Rˣ |
|---|---|---|---|---|
| III-133 | dibenzo-suberane-5-yl | 2-E-(methyl)-vinylene | 3-methoxymethyl-isoxazol-5-yl | H |
| III-134 | dibenzo-suberane-5-yl | 2-Z-(methyl)-vinylene | 3-methoxymethyl-isoxazol-5-yl | H |
| III-135 | diphenylmethyl | 2-E-(methyl)-vinylene | 3-methoxymethyl-isoxazol-5-yl | H |
| III-136 | diphenylmethyl | 2-Z-(methyl)-vinylene | 3-methoxymethyl-isoxazol-5-yl | H |

Specific examples of type III with Z=Z–2 include:

| Example No. | R² = R³ | A | B | R = Rˣ |
|---|---|---|---|---|
| III-137 | phenyl | 2-E-(methyl)-vinylene | 3-methoxymethyl-isoxazol-5-yl | H |
| III-138 | phenyl | 2-Z-(methyl)-vinylene | 3-methoxymethyl-isoxazol-5-yl | H |

Specific examples of type III with Z=Z–3 include:

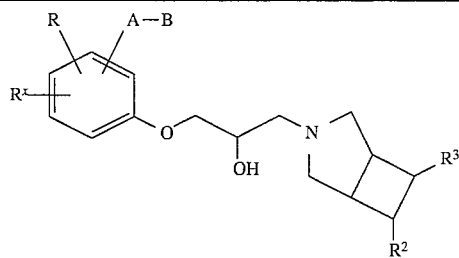

| Example No. | R² | R³ | A | B | R | Rˣ |
|---|---|---|---|---|---|---|
| III-139 | 6-phenyl | 7-phenyl | 2-E-vinylene | 3-methoxymethyl-isoxazol-5-yl | H | H |
| III-140 | (4-fluor-phenyl) | H | 2-E-vinylene | 3-methoxymethyl-isoxazol-5-yl | H | H |
| III-141 | 4-t.butyl-phenyl | H | 2-E-vinylene | 3-methoxymethyl-isoxazol-5-yl | 3,4-butadien-1,4-diyl | |
| III-153 | 6-phenyl | 7-phenyl | 2-E-vinylene | 3-isopropyl-isoxazol-5-yl | H | H |
| III-154 | 4-t.butyl-phenyl | H | 2-E-vinylene | 5-methoxymethyl-isoxazol-3-yl | H | H |

Specific examples of type III with Z=Z–4 include:

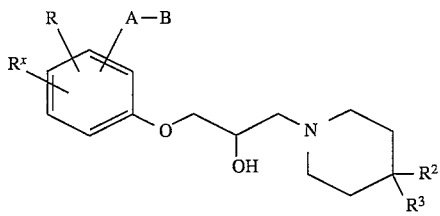

| Example No. | R² = R³ | A | B | R = Rˣ |
|---|---|---|---|---|
| III-165 | phenyl | 2-E-vinylene | 3-methoxymethyl-isoxazol-5-yl | H |
| III-166 | phenyl | 2-Z-vinylene | 3-methoxymethyl-isoxazol-5-yl | H |
| III-167 | phenyl | 3-E-vinylene | 3-methoxymethyl-isoxazol-5-yl | H |
| III-168 | phenyl | 3-Z-vinylene | 3-methoxymethyl-isoxazol-5-yl | H |
| III-169 | phenyl | 4-E-vinylene | 3-methoxymethyl-isoxazol-5-yl | H |
| III-170 | phenyl | 4-Z-vinylene | 3-methoxymethyl-isoxazol-5-yl | H |

| Example No. | R² + R³ | A | B | R = Rˣ |
|---|---|---|---|---|
| III-171 | dibenzo-suberane-5-yliden | 2-E-vinylene | 3-methoxymethyl-isoxazol-5-yl | H |
| III.172 | dibenzo-suberane-5-yliden | 2-Z-vinylene | 3-methoxymethyl-isoxazol-5-yl | H |
| III-173 | dibenzo-suberane-5-yliden | 3-E-vinylene | 3-methoxymethyl-isoxazol-5-yl | H |
| III-174 | dibenzo-suberane-5-yliden | 3-Z-vinylene | 3-methoxymethyl-isoxazol-5-yl | H |
| III-175 | dibenzo-suberane-5-yliden | 4-E-vinylene | 3-methoxymethyl-isoxazol-5-yl | H |
| III-176 | dibenzo-suberane-5-yliden | 4-Z-vinylene | 3-methoxymethyl-isoxazol-5-yl | H |
| III-177 | dibenzo-suberene-5-yliden | 2-E-vinylene | 3-methoxymethyl-isoxazol-5-yl | H |
| III-178 | dibenzo-suberene-5-yliden | 2-Z-vinylene | 3-methoxymethyl-isoxazol-5-yl | H |

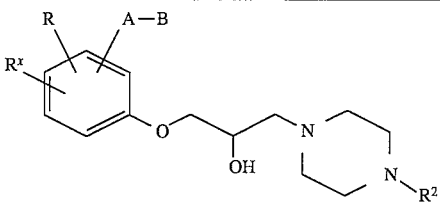

| Example No. | R² | A | B | R = Rˣ |
|---|---|---|---|---|
| III-179 | dibenzo-suberane-5-yliden | 2-E-vinylene | 2-methylmethoxy-thiazol-4-yl | H |

Specific examples of type IV with Z=Z–1 include:

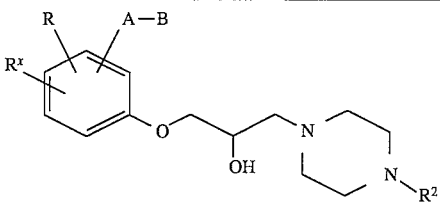

| Example No. | R² | A | B | R = Rˣ |
|---|---|---|---|---|
| IV-1 | diphenyl-methyl | 2-E-vinylene | 3-methoxymethyl-isoxazol-5-yl | H |
| IV-2 | dibenzo-suberane-5-yl | 2-E-vinylene | 3-methoxymethyl-isoxazol-5-yl | H |
| IV-3 | diphenyl-acetyl | 2-E-vinylene | 3-methoxymethyl-isoxazol-5-yl | H |
| IV-4 | cyclohexyl-phenyl-methyl | 2-E-vinylene | 3-methoxymethyl-isoxazol-5-yl | H |

Specific examples of type IV with Z=Z–2 include:

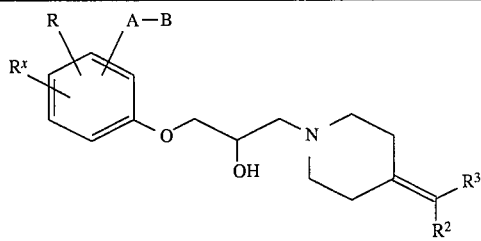

| Example No. | $R^2 = R^3$ | A | B | R = $R^x$ |
|---|---|---|---|---|
| IV-5 | phenyl | 2-E-vinylene | 3-methoxymethyl-isoxazol-5-yl | H |
| IV-6 | phenyl | 2-Z-vinylene | 3-methoxymethyl-isoxazol-5-yl | H |
| IV-7 | phenyl | 3-E-vinylene | 3-methoxymethyl-isoxazol-5-yl | H |
| IV-8 | phenyl | 3-Z-vinylene | 3-methoxymethyl-isoxazol-5-yl | H |
| IV-9 | phenyl | 4-E-vinylene | 3-methoxymethyl-isoxazol-5-yl | H |
| IV-10 | phenyl | 4-Z-vinylene | 3-methoxymethyl-isoxazol-5-yl | H |

Specific examples of type V with Z=Z–1 include:

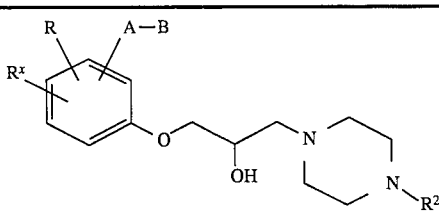

| Example No. | $R^2$ | A | B | R = $R^x$ |
|---|---|---|---|---|
| V-1 | dibenzo-suberane-5-yl | 2-methyleneoxy | 3-methoxymethyl-isoxazol-5-yl | H |
| V-2 | dibenzo-suberane-5-yl | 2-methyleneoxymethylene | 3-methoxymethyl-isoxazol-5-yl | H |
| V-3 | diphenyl-methyl | 2-methyleneoxymethylene | 3-methoxymethyl-isoxazol-5-yl | H |
| V-4 | diphenyl-methyl | 2-methyleneoxy | 3-methoxymethyl-isoxazol-5-yl | H |
| V-5 | cyclohexyl-phenyl-methyl | 2-methyleneoxy | 3-methoxymethyl-isoxazol-5-yl | H |
| V-6 | diphenyl-methyl | 2-methyleneoxy | 3-methyl-isoxazol-5-yl | H |
| V-7 | dibenzo-suberane-5-y | 2-methyleneoxy | 3-methyl-isoxazol-5-yl | H |
| V-8 | dibenzo-suberane-5-y | 2-methyleneoxy | 3-isopropyl-isoxazol-5-yl | H |
| V-9 | dibenzo-suberane-5-yl | 2-methyleneoxy | 3-phenyl-isoxazol-5-yl | H H |
| V-10 | dibenzo-suberane-5-yl | 2-methyleneoxy | 3-ethoxy-carboxy-isoxazol-5-yl | H H |
| V-11 | dibenzo-suberane-5-y | 2-methyleneoxy | thiophen-2-yl | H |
| V-12 | dibenzo-suberane-5-yl | 2-methyleneoxy | thiophen-3-yl | H |
| V-13 | dibenzo-suberane-5-yl | 2-methyleneoxy | pyridin-2-yl | H |
| V-14 | dibenzo-suberane-5-yl | 2-methyleneoxy | pyridin-3-yl | H |

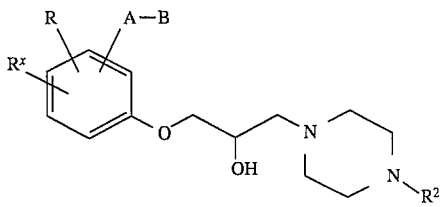

| Example No. | $R^2$ | A | B | R = $R^x$ |
|---|---|---|---|---|
| V-15 | dibenzo-suberane-5-yl | 2-methyleneoxy | pyridin-4-yl | H |
| V-16 | dibenzo-suberane-5-yl | 2-methyleneoxy | pyrazol-2-y | H |
| V-17 | dibenzo-suberane-5-yl | methyleneoxy | pyrazol-3-y | H |
| V-18 | dibenzo-suberane-5-yl | methyleneoxy | N-methyl-pyazol-2-yl | H |
| V-19 | dibenzo-suberane-5-yl | 2-methyleneoxy | furan-2-yl | H |
| V-20 | dibenzo-suberane-5-yl | 2-methyleneoxy | furan-3-yl | H |
| V-21 | dibenzo-suberene-5-yl | 2-methyleneoxy | 3-methoxy-methyl-isoxazol-5-yl- | H |
| V-22 | dibenzo-suberene-5-yl | 2-methyleneoxy | 3-methyl-isoxazol-5-yl | H |
| V-23 | dibenzo-suberene-5-yl | 2-methyleneoxy | 3-isopropyl-isoxazol-5-yl | H |
| V-24 | dibenzo-suberene-5-yl | 2-methyleneoxy | 3-phenyl-isoxazol-5-yl | H |
| V-25 | dibenzo-suberene-5-yl | 2-methyleneoxy | 3-ethoxy-carboxy-isoxazol-5-yl | H |
| V-26 | dibenzo-suberene-5-yl | 2-methyleneoxy | thiophen-2-yl | H |
| V-27 | dibenzo-suberene-5-yl | 2-methyleneoxy | thiophen-3-yl | H |
| V-28 | dibenzo-suberene-5-yl | 2-methyleneoxy | pyridin-2-yl | H |
| V-29 | dibenzo-suberene-5-yl | 2-methyleneoxy | pyridin-3-yl | H |
| V-30 | dibenzo-suberene-5-yl | 2-methyleneoxy | pyridin-4-yl | H |
| V-31 | dibenzo-suberene-5-yl | 2-methyleneoxy | pyrazol-2-yl | H |
| V-32 | dibenzo-suberene-5-yl | 2-methyleneoxy | pyrazol-3-yl | H |
| V-33 | dibenzo-suberene-5-yl | 2-methyleneoxy | N-methyl-pyrazol-2-yl | H |
| V-34 | dibenzo-suberene-5-yl | 2-methyleneoxy | N-methyl-pyrazol-3-yl- | H |
| V-35 | dibenzo-suberene-5-yl | 2-methyleneoxy | furan-2-yl | H |
| V-36 | dibenzo-suberene-5-yl | 2-methyleneoxy | furan-3-yl | H |
| V-37 | diphenyl-methyl | 2-methyleneoxy | 3-phenyl-isoxazol-5-yl | H |
| V-38 | diphenyl-methyl | 2-methyleneoxy | 3-ethoxy-carboxy-isoxazol-5-yl | H |
| V-39 | diphenyl-methyl | 2-methyleneoxy | thiophen-2-yl | H |
| V-40 | diphenyl-methyl | 2-methyleneoxy | thiophen-3-yl | H |
| V-41 | diphenyl-methy | 2-methyleneoxy | pyridin-2-yl | H |
| V-42 | diphenyl-methyl | 2-methyleneoxy | pyridin-3-yl | H |
| V-43 | diphenyl-methyl | 2-methyleneoxy | pyridin-4-yl | H |
| V-44 | diphenyl-methyl | 2-methyleneoxy | pyrazol-2-yl | H |
| V-45 | diphenyl-methyl | 2-methyleneoxy | pyrazol-3-yl | H |
| V-46 | diphenyl-methyl | 2-methyleneoxy | N-methyl-pyazol-2-yl | H |

-continued

Structure (for V-47 to V-52):
Aryl ring with R, Rx substituents and A–B group, connected via –O–CH2–CH(OH)–CH2–N(piperazine)–N–R2

| Example No. | R² | A | B | R = Rˣ |
|---|---|---|---|---|
| V-47 | diphenyl-methyl | 2-methyleneoxy | N-methyl-pyazol-3-yl | H |
| V-48 | diphenyl-methyl | 2-methyleneoxy | furan-2-yl | H |
| V-49 | diphenyl-methyl | 2-methyleneoxy | furan-3-yl | H |
| V-50 | phenyl | 2-methyleneoxy | 3-methoxy-methyl-isoxazol-5-yl | H |
| V-51 | phenyl | 2-methylene-oxymethylene | 3-methoxy-methyl-isoxazol-5-yl | H |
| V-52 | diphenyl-methyl | 2-methyleneoxy | 3-isopropyl-isoxazol-5-yl | H |

Specific examples of type V with Z=Z–2 include:

Structure: aryl–O–CH2–CH(OH)–CH2–N(piperidine)=C(R²)(R³)

| Example No. | R² = R³ | A | B | R = Rˣ |
|---|---|---|---|---|
| V-53 | phenyl | 2-methyleneoxy | 3-methoxymethyl-isoxazol-5-yl | H |
| V-54 | phenyl | 2-methyleneoxy-methylene | 3-methoxymethyl-isoxazol-5-yl | H |

Specific examples of type VI with Z=Z–1 include:

Structure: aryl–O–CH2–CH(OH)–CH2–N(piperazine)–N–R²

| Example No. | R² | A | B | R = Rˣ |
|---|---|---|---|---|
| VI-1 | diphenyl-methyl | 2-ethylene | 4,5-dimethyl-oxazol-2-yl | H |
| VI-2 | dibenzo-suberane-5-yl | 2-ethylene | 3-methoxymethyl-isoxazol-5-yl | H |
| VI-3 | diphenyl-methyl | 2-ethylene | 3-methoxymethyl-isoxazol-5-yl | H |
| VI-4 | diphenyl-acetyl | 2-ethylene | 3-methoxymethyl-isoxazol-5-yl | H |
| VI-5 | cyclohexyl-phenyl-methyl | 2-ethylene | 3-methoxymethyl-isoxazol-5-yl | H |

Specific examples of type VI with Z=Z–2 include:

Structure: aryl–O–CH2–CH(OH)–CH2–N(piperidine)=C(R²)(R³)

| Example No. | R² = R³ | A | B | R = Rˣ |
|---|---|---|---|---|
| VI-6 | phenyl | 2-ethylene | 3-methoxymethyl-isoxazol-5-yl | H |

Specific examples of type VI with Z=Z–3 include:

Structure: aryl–O–CH2–CH(OH)–CH2–N(bicyclic)–R², R³

| Example No. | R² | R³ | A | B | R = Rˣ |
|---|---|---|---|---|---|
| VI-7 | 6-(4-fluoro-phenyl) | H | 2-ethylene | quinolin-2-yl | H |

Specific examples of type V with Z=Z–1 include:

Structure: aryl–O–CH2–CH(OH)–CH2–N(piperazine)–N–R²

| Example No. | R² | A | B | R = Rˣ |
|---|---|---|---|---|
| VII-1 | diphenyl-methyl | 2-ethinylene | 3-methoxymethyl-isoxazol-5-yl | H |
| VII-2 | dibenzo-suberane-5-yl | 2-ethinylene | 3-methoxymethyl-isoxazol-5-yl | H |
| VII-3 | diphenyl-methyl | 2-ethinylene | 3-methoxymethyl-isoxazol-5-yl | H |
| VII-4 | diphenyl-acetyl | 2-ethinylene | 3-methoxymethyl-isoxazol-5-yl | H |
| VII-5 | cyclohexyl-phenyl-methyl | 2-ethinylene | 3-methoxymethyl-isoxazol-5-yl | H |
| VII-6 | diphenyl-methyl | 2-ethinylene | 3-methyl-isoxazol-5-yl | H |
| VII-7 | dibenzo-suberane-5-yl | 2-ethinylene | 3-methyl-isoxazol-5-yl | H |
| VII-8 | diphenyl-methyl | 2-ethinylene | 3-methyl-isoxazol-5-yl | H |
| VII-9 | diphenyl-acetyl | 2-ethinylene | 3-methyl-isoxazol-5-yl | H |
| VII-10 | cyclohexyl-phenyl-methyl | 2-ethinylene | 3-methyl-isoxazol-5-yl | H |

Specific examples of type VIII with Z=Z–1 include:

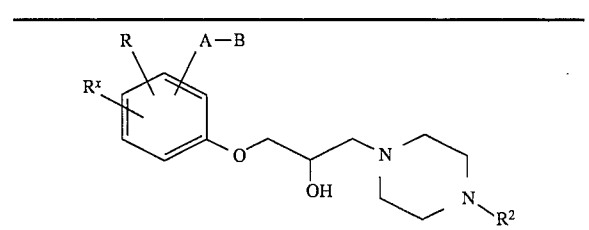

| Example No. | R² | A | B | R = Rˣ |
|---|---|---|---|---|
| VIII-1 | dibenzo-suberane-5-yl | 2-carbonyl | 3-methoxy-methyl-isoxazol-5-yl | H |
| VIII-2 | diphenyl-methyl | 2-carbonyl | 3-methoxy-methyl-isoxazol-5-yl | H |
| VIII-3 | diphenyl-acetyl | 2-carbonyl | 3-methoxy-methyl-isoxazol-5-yl | H |
| VIII-4 | cyclohexyl-phenyl-methyl | 2-carbonyl | 3-methoxy-methyl-isoxazol-5-yl | H |
| VIII-5 | dibenzo-suberane-5-yl | 2-carbonyl | 3-methoxy-methyl-isoxazol-5-yl | 4,5-di-methoxy |
| VIII-6 | diphenyl-methyl | 2-carbonyl | 3-methoxy-methyl-isoxazol-5-yl | 4,5-di-methoxy |
| VIII-7 | diphenyl-methyl | 2-carbonyl | 3-methoxy-methyl-isoxazol-5-yl | 4,5-di-methoxy |
| VIII-8 | cyclohexyl-phenyl-methyl | 2-carbonyl | 3-methoxy-methyl-isoxazol-5-yl | 4,5-di-methoxy |
| VIII-9 | dibenzo-suberane-5-yl | 2-carbonyl | phenyl | H |
| VIII-10 | diphenyl-methyl | 2-carbonyl | phenyl | H |
| VIII-11 | diphenyl-acetyl | 2-carbonyl | phenyl | H |
| VIII-12 | cyclohexyl-phenyl-methyl | 2-carbonyl | phenyl | H |
| VIII-13 | dibenzo-suberane-5-yl | 2-carbonyl | phenyl | 4,5-di-methoxy |
| VIII-14 | diphenyl-methyl | 2-carbonyl | phenyl | 4,5-di-methoxy |
| VIII-15 | diphenyl-acetyl | 2-carbonyl | phenyl | 4,5-di-methoxy |
| VIII-16 | cyclohexyl-phenyl-methyl | 2-carbonyl | phenyl | 4,5-di-methoxy |
| VIII-17 | dibenzo-suberane-5-yl | 2-carbonyl-dimethylene | 3-methoxy-methyl-isoxazol-5-yl | H |
| VIII-18 | diphenyl-methyl | 2-carbonyl-dimethylene | 3-methoxy-methyl-isoxazol-5-yl | H |
| VIII-19 | diphenyl-acetyl | 2-carbonyl-dimethylene | 3-methoxy-methyl-isoxazol-5-yl | H |
| VIII-20 | cyclohexyl-phenyl-methyl | 2-carbonyl-dimethylene | 3-methoxy-methyl-isoxazol-5-yl | H |
| VIII-21 | dibenzo-suberane-5-yl | 3-carbonyl-dimethylene | 3-methoxy-methyl-isoxazol-5-yl | 4,5-di-methoxy |
| VIII-22 | diphenyl-methyl | 2-carbonyl-dimethylene | 3-methoxy-methyl-isoxazol-5-yl | 4,5-di-methoxy |
| VIII-23 | diphenyl-acetyl | 2-carbonyl-dimethylene | 3-methoxy-methyl-isoxazol-5-yl | 4,5-di-methoxy |
| VIII-24 | cyclohexyl-phenyl-methyl | 2-carbonyl-dimethylene | 3-methoxy-methyl-isoxazol-5-yl | 4,5-di-methoxy |

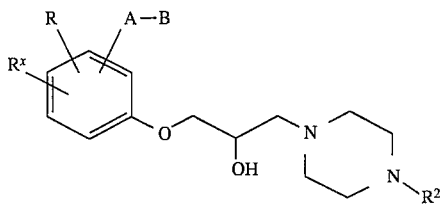

| Example No. | R² | A | B | R = Rˣ |
|---|---|---|---|---|
| VIII-25 | dibenzo-suberane-5-yl | 2-carbonyl-dimethylene | phenyl | H |
| VIII-26 | diphenyl-methyl | 2-carbonyl-dimethylene | phenyl | H |
| VIII-27 | diphenyl-acetyl | 2-carbonyl-dimethylene | phenyl | H |
| VIII-28 | cyclohexyl-phenyl-methyl | 2-carbonyl-dimethylene | phenyl | H |
| VIII-29 | dibenzo-suberene-5-yl | 2-carbonyl-dimethylene | phenyl | H |
| VIII-30 | bis(4-fluoro-phenyl)-methyl | 2-carbonyl-dimethylene | phenyl | H |
| VIII-31 | bis(4-methoxy-phenyl)-methyl | 2-carbonyl-dimethylene | phenyl | H |
| VIII-32 | 4-methoxy-phenyl | 2-carbonyl-dimethylene | phenyl | H |
| VIII-33 | 3-methoxy-phenyl | 2-carbonyl-dimethylene | phenyl | H |
| VIII-34 | 2-methoxy-phenyl | 2-carbonyl-dimethylene | phenyl | H |
| VIII-35 | 4-fluoro-phenyl | 2-carbonyl-dimethylene | phenyl | H |
| VIII-36 | 3-fluoro-phenyl | 2-carbonyl-dimethylene | phenyl | H |
| VIII-37 | 2-fluoro-phenyl | 2-carbonyl-dimethylene | phenyl | H |
| VIII-38 | 4-trifluoro-methylphenyl | 2-carbonyl-dimethylene | phenyl | H |
| VIII-39 | 3-trifluoro-methylphenyl | 2-carbonyl-dimethylene | phenyl | H |
| VIII-40 | 2-trifluoro-methylphenyl | 2-carbonyl-dimethylene | phenyl | H |
| VIII-41 | 4-tert.butyl-phenyl | 2-carbonyl-dimethylene | phenyl | H |
| VIII-42 | 3,4-di-methoxy-phenyl | 2-carbonyl-dimethylene | phenyl | H |
| VIII-43 | 2,3,4-tri-methoxy-phenyl | 2-carbonyl-dimethylene | phenyl | H |
| VIII-44 | 3,4,5-tri-methoxy-phenyl | 2-carbonyl-dimethylene | phenyl | H |
| VIII-45 | 3,4-methylene-dioxyphenyl | 2-carbonyl-dimethylene | phenyl | H |
| VIII-46 | (4-methoxy-phenyl)-methyl | 2-carbonyl-dimethylene | phenyl | H |
| VIII-47 | (3-methoxy-phenyl)-methyl | 2-carbonyl-dimethylene | phenyl | H |
| VIII-48 | (2-methoxy-phenyl)-methyl | 2-carbonyl-dimethylene | phenyl | H |
| VIII-49 | (4-fluoro-phenyl)-methyl | 2-carbonyl-dimethylene | phenyl | H |
| VIII-50 | (3-fluoro-phenyl)-methyl | 2-carbonyl-dimethylene | phenyl | H |
| VIII-51 | (2-fluoro-phenyl)- | 2-carbonyl-dimethylene | phenyl | H |

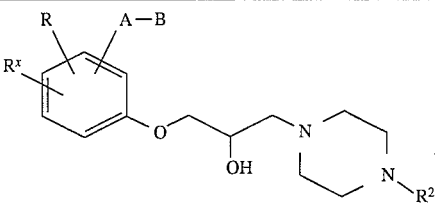

| Example No. | R² | A | B | R = Rˣ |
|---|---|---|---|---|
| VIII-52 | (4-trifluoro-methyl-phenyl)-methyl | 2-carbonyl-dimethylene | phenyl | H |
| VIII-53 | (3-trifluoro-methyl-phenyl)-methyl | 2-carbonyl-dimethylene | phenyl | H |
| VIII-54 | (2-trifluoro-methyl-phenyl)-methyl | 2-carbonyl-dimethylene | phenyl | H |
| VIII-55 | (4.tert.butyl-phenyl)-methyl | 2-carbonyl-dimethylene | phenyl | H |
| VIII-56 | (3,4-methylene-dioxy-phenyl)-methyl | 2-carbonyl-dimethylene | phenyl | H |
| VIII-57 | (2,3,4-tri-methoxy-phenyl)-methyl | 2-carbonyl-dimethylene | phenyl | H |
| VIII-58 | (3,4,5-tri-methoxy-phenyl)-methyl | 2-carbonyl-dimethylene | phenyl | H |
| VIII-59 | (3,4-dimethoxy-phenyl)-methyl | 2-carbonyl-dimethylene | phenyl | H |
| VIII-60 | (4-methoxy-phenyl)-ethyl | 2-carbonyl-dimethylene | phenyl | H |
| VIII-61 | (4-fluoro-phenyl)-ethyl | 2-carbonyl-dimethylene | phenyl | H |
| VIII-62 | (4-trifluoro-methyl-phenyl)-methyl | 2-carbonyl-dimethylene | phenyl | H |
| VIII-63 | (4-tert.butyl-phenyl)-ethyl | 2-carbonyl-dimethylene | phenyl | H |
| VIII-64 | (3,4-methylene-dioxyphenyl)-methyl | 2-carbonyl-dimethylene | phenyl | H |
| VIII-65 | (2,3,4-tri-methoxy-phenyl)-methyl | 2-carbonyl-dimethylene | phenyl | H |
| VIII-66 | (3,4,5-tri-methoxy-phenyl)-methyl | 2-carbonyl-dimethylene | phenyl | H |
| VIII-67 | (3,4-di-methoxy-phenyl-methyl | 2-carbonyl-dimethylene | phenyl | H |
| VIII-68 | (2,3,4-tri-methoxy-phenyl)-methyl | 2-carbonyl-dimethylene | phenyl | 4,5-di-methoxy |
| VIII-69 | diphenyl-methyl | 2-carbonyl-dimethylene | phenyl | 4,5-di-methoxy |
| VIII-70 | diphenyl-acetyl | 2-carbonyl-dimethylene | phenyl | 4,5-di-methoxy |

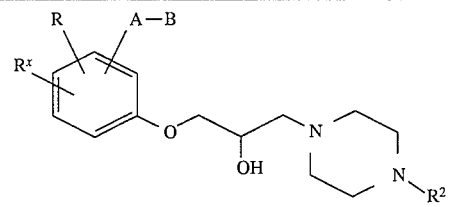

| Example No. | R² | A | B | R = Rˣ |
|---|---|---|---|---|
| VIII-71 | cyclohexyl-methyl | 2-carbonyl-dimethylene | phenyl | 4,5-di-methoxy |
| VIII-72 | dibenzo-suberene-5-yl | 2-carbonyl-dimethylene | phenyl | 4,5-di-methoxy |
| VIII-73 | bis(4-fluoro-phenyl)-methyl | 2-carbonyl-dimethylene | phenyl | 4,5-di-methoxy |
| VIII-74 | bis(methoxy-phenyl)-methyl | 2-carbonyl-dimethylene | phenyl | 4,5-di-methoxy |
| VIII-75 | 4-methoxy-phenyl | 2-carbonyl-dimethylene | phenyl | 4,5-di-methoxy |
| VIII-76 | 3-methoxy-phenyl | 2-carbonyl-dimethylene | phenyl | 4,5-di-methoxy |
| VIII-77 | 2-methoxy-phenyl | 2-carbonyl-dimethylene | phenyl | 4,5-di-methoxy |
| VIII-78 | 4-fluoro-phenyl | 2-carbonyl-dimethylene | phenyl | 4,5-di-methoxy |
| VIII-79 | 3-fluoro-phenyl | 2-carbonyl-dimethylene | phenyl | 4,5-di-methoxy |
| VIII-80 | 2-fluoro-phenyl | 2-carbonyl-dimethylene | phenyl | 4,5-di-methoxy |
| VIII-81 | 4-trifluoro-methyl-phenyl | 2-carbonyl-dimethylene | phenyl | 4,5-di-methoxy |
| VIII-82 | 3-trifluoro-methyl-phenyl | 2-carbonyl-dimethylene | phenyl | 4,5-di-methoxy |
| VIII-83 | 2-trifluoro-methyl-phenyl | 2-carbonyl-dimethylene | phenyl | 4,5-di-methoxy |
| VIII-83 | 4-tert.butyl-phenyl | 2-carbonyl-dimethylene | phenyl | 4,5-di-methoxy |
| VIII-84 | 3,4-di-methoxy-phenyl | 2-carbonyl-dimethylene | phenyl | 4,5-di-methoxy |
| VIII-85 | 2,3,4-tri-methoxy-phenyl | 2-carbonyl-dimethylene | phenyl | 4,5-di-methoxy |
| VIII-86 | 3,4,5-tri-methoxy-phenyl | 2-carbonyl-dimethylene | phenyl | 4,5-di-methoxy |
| VIII-87 | 3,4-methylene-dioxyphenyl | 2-carbonyl-dimethylene | phenyl | 4,5-di-methoxy |
| VIII-88 | (4-methoxy-phenyl)-methyl | 2-carbonyl-dimethylene | phenyl | 4,5-di-methoxy |
| VIII-89 | (3-methoxy-phenyl)-methyl | 2-carbonyl-dimethylene | phenyl | 4,5-di-methoxy |
| VIII-90 | (2-methoxy-phenyl)-methyl | 2-carbonyl-dimethylene | phenyl | 4,5-di-methoxy |
| VIII-91 | (4-fluoro-phenyl)-methyl | 2-carbonyl-dimethylene | phenyl | 4,5-di-methoxy |
| VIII-92 | (3-fluoro-phenyl)-methyl | 2-carbonyl-dimethylene | phenyl | 4,5-di-methoxy |
| VIII-93 | (2-fluoro-phenyl)-methyl | 2-carbonyl-dimethylene | phenyl | 4,5-di-methoxy |
| VIII-94 | (4-trifluoro-methyl-phenyl)- | 2-carbonyl-dimethylene | phenyl | 4,5-di-methoxy |

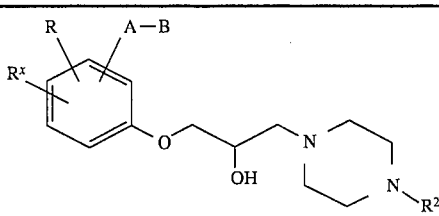

| Example No. | R² | A | B | R = Rˣ |
|---|---|---|---|---|
| VIII-95 | methyl (3-trifluoro-methyl-phenyl)-methyl | 2-carbonyl-dimethylene | phenyl | 4,5-di-methoxy |
| VIII-96 | (2-trifluoro-methyl-phenyl)-methyl | 2-carbonyl-dimethylene | phenyl | 4,5-di-methoxy |
| VIII-97 | (4-tert.butyl-phenyl)-methyl | 2-carbonyl-dimethylene | phenyl | 4,5-di-methoxy |
| VIII-98 | (3,4-methylene-dioxy-phenyl)-methyl | 2-carbonyl-dimethylene | phenyl | 4,5-di-methoxy |
| VIII-99 | dibenzo-suberane-5-yl | 2-carbonyl-dimethylene | phenyl | 4,5-di-methoxy |
| VIII-100 | (3,4,5-tri-methoxy-phenyl)-methyl | 2-carbonyl-dimethylene | phenyl | 4,5-di-methoxy |
| VIII-101 | (3,4-di-methoxy-phenyl)-methyl | 2-carbonyl-dimethylene | phenyl | 4,5-di-methoxy |
| VIII-102 | (4-methoxy-phenyl)-ethyl | 2-carbonyl-dimethylene | phenyl | 4,5-di-methoxy |
| VIII-103 | (4-fluoro-phenyl)-ethyl | 2-carbonyl-dimethylene | phenyl | 4,5-di-methoxy |
| VIII-104 | (4-trifluoro-methyl-phenyl)-ethyl | 2-carbonyl-methylene | phenyl | 4,5-di-methoxy |
| VIII-105 | (4-tert.butyl-phenyl)-ethyl | 2-carbonyl-dimethylene | phenyl | 4,5-di-methoxy |

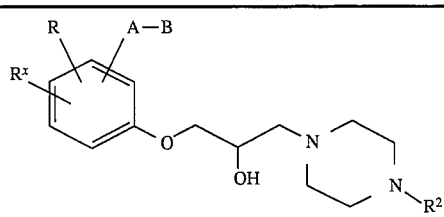

| Example No. | R² | A | B | R = Rˣ |
|---|---|---|---|---|
| VIII-106 | (3,4-methylene-dioxyphenyl)-ethyl | 2-carbonyl-dimethylene | phenyl | 4,5-di-methoxy |
| VIII-107 | (2,3,4-tri-methoxy-phenyl)-ethyl | 2-carbonyl-dimethylene | phenyl | 4,5-di-methoxy |
| VIII-108 | (3,4,5-tri-methoxy-phenyl)-ethyl | 2-carbonyl-dimethylene | phenyl | 4,5-di-methoxy |
| VIII-109 | (3,4-di-methoxy-phenyl)-ethyl | 2-carbonyl-methylene | phenyl | 4,5-di-methoxy |
| VIII-142 | phenyl | 2-carbonyl-dimethylene | phenyl | 4,5-di-methoxy |
| VIII-143 | phenylmethyl | 2-carbonyl-dimethylene | phenyl | 4,5-di-methoxy |
| VIII-144 | phenylethyl | 2-carbonyl-dimethylene | phenyl | 4,5-di-methoxy |
| VIII-145 | phenyl | 2-carbonyl-dimethylene | phenyl | H |
| VIII-146 | phenylmethyl | 2-carbonyl-dimethylene | phenyl | H |
| VIII-147 | phenylethyl | 2-carbonyl-dimethylene | phenyl | H |
| VIII-148 | phenyl | 2-carbonyl | phenyl | 4,5-di-methoxy |
| VIII-149 | phenylethyl | 2-carbonyl | phenyl | 4,5-di methoxy |
| VIII-150 | phenylethyl | 2-carbonyl | phenyl | 4,5-di-methoxy |
| VIII-151 | phenyl | 2-carbonyl | phenyl | H |
| VIII-152 | phenylmethyl | 2-carbonyl | phenyl | H |
| VIII-153 | phenylethyl | 2-carbonyl | phenyl | H |

Specific examples of type VIII with Z=Z–2 include:

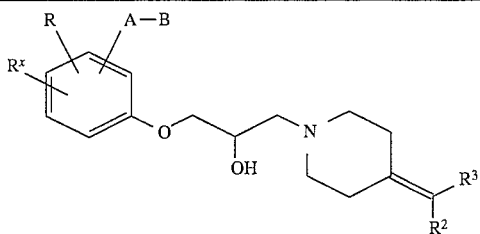

| Example No. | $R^2 = R^3$ | A | B | $R = R^x$ |
|---|---|---|---|---|
| VIII-110 | phenyl | 2-carbonyl | 3-methoxymethyl-isoxazol-5-yl | H |
| VIII-111 | phenyl | 2-carbonyl | 3-methoxymethyl-isoxazol-5-yl | 4,5-dimethoxy |
| VIII-112 | phenyl | 2-carbonyl | phenyl | H |
| VIII-113 | phenyl | 2-carbonyl | phenyl | 4,5-dimethoxy |
| VIII-114 | phenyl | 2-carbonyldimethylene | 3-methoxymethyl-isoxazol-5-yl | H |
| VIII-115 | phenyl | 2-carbonyldimethylene | 3-methoxymethyl-isoxazol-5-yl | 4,5-dimethoxy |
| VIII-116 | phenyl | 2-carbonyldimethylene | phenyl | H |
| VIII-117 | phenyl | 2-carbonyldimethylene | phenyl | 4,5-dimethoxy |

Specific examples of type VIII with Z=Z–3 include:

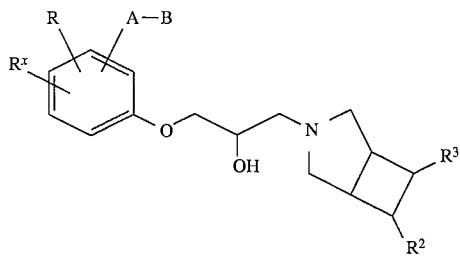

| Example No. | $R^2$ | $R^3$ | A | B | $R = R^x$ |
|---|---|---|---|---|---|
| VIII-118 | 6-phenyl | 7-phenyl | 2-carbonyl | 3-methoxymethyl-isoxazol-5-yl | H |
| VIII-119 | 6-phenyl | H | 2-carbonyl | 3-methoxymethyl-isoxazol-5-yl | 4,5-dimethoxy |
| VIII-120 | 6-phenyl | 7-phenyl | 2-carbonyl | phenyl | H |
| VIII-121 | 6-phenyl | H | 2-carbonyl | phenyl | 4,5-dimethoxy |
| VIII-122 | 6-phenyl | 7-phenyl | 2-carbonyldimethylene | 3-methoxymethyl-isoxazol-5-yl | H |
| VIII-123 | 6-phenyl | H | 2-carbonyldimethylene | 3-methoxymethyl-isoxazol-5-yl | 4,5-dimethoxy |
| VIII-124 | 6-phenyl | 7-phenyl | 2-carbonyldimethylene | phenyl | H |
| VIII-125 | 6-phenyl | H | 2-carbonyldimethylene | phenyl | 4,5-dimethoxy |

Specific examples of type VIII with Z=Z–4 include:

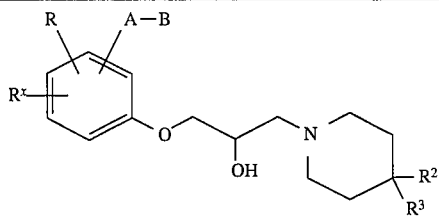

| Example No. | $R^2 = R^3$ | A | B | $R = R^x$ |
|---|---|---|---|---|
| VIII-126 | phenyl | 2-carbonyl | 3-methoxymethyl-isoxazol-5-yl | H |
| VIII-127 | phenyl | 2-carbonyl | 3-methoxymethyl-isoxazol-5-yl | 4,5-dimethoxy |
| VIII-128 | phenyl | 2-carbonyl | phenyl | H |
| VIII-129 | phenyl | 2-carbonyl | phenyl | 4,5-dimethoxy |
| VIII-130 | phenyl | 2-carbonyldimethylene | 3-methoxymethyl-isoxazol-5-yl | H |
| VIII-131 | phenyl | 2-carbonyldimethylene | 3-methoxymethyl-isoxazol-5-yl | 4,5-dimethoxy |
| VIII-132 | phenyl | 2-carbonyldimethylene | phenyl | H |
| VIII-133 | phenyl | 2-carbonyldimethylene | phenyl | 4,5-dimethoxy |

| Example No. | $R^2 + R^3$ | A | B | $R = R^x$ |
|---|---|---|---|---|
| VIII-134 | dibenzosuberane-5-yliden | 2-carbonyl | 3-methoxymethyl-isoxazol-5-yl | H |
| VIII-135 | dibenzosuberane-5-yliden | 2-carbonyl | 3-methoxymethyl-isoxazol-5-yl | 4,5-dimethoxy |
| VIII-136 | dibenzosuberane-5-yliden | 2-carbonyl | phenyl | H |
| VIII-137 | dibenzosuberane-5-yliden | 2-carbonyl | phenyl | 4,5-dimethoxy |
| VIII-138 | dibenzosuberane-5-yliden | 2-carbonyldimethylene | 3-methoxymethyl-isoxazol-5-yl | H |
| VIII-139 | dibenzosuberane-5-yliden | 2-carbonyldimethylene | 3-methoxymethyl-isoxazol-5-yl | 4,5-dimethoxy |
| VIII-140 | dibenzosuberene-5-yliden | 2-carbonyldimethylene | phenyl | H |
| VIII-141 | dibenzosuberene-5-yliden | 2-arbonyldimethylene | phenyl | 4,5-dimethoxy |

Specific examples of type IX with Z=Z-1 include:

| Example No. | $R^2$ | A | B | $R = R^x$ |
|---|---|---|---|---|
| IX-1 | dibenzo-suberane-5-yl | 2-carbonylimino | 3-methoxy-methyl-isoxazol-5-yl | H |
| IX-2 | diphenyl-methyl | 2-carbonylimino | 3-methoxy-methyl-isoxazol-5-yl | H |
| IX-3 | diphenyl-acetyl | 2-carbonylimino | 3-methoxy-methyl-isoxazol-5-yl | H |
| IX-4 | cyclohexyl-phenyl-methyl | 2-carbonylimino | 3-methoxy-methyl-isoxazol-5-yl | H |
| IX-5 | dibenzo-suberane-5-yl | 2-(N-methyl)-carbonylimino | 3-methoxy-methyl-isoxazol-5-yl | H |
| IX-6 | diphenyl-methyl | 2-(N-methyl)-carbonylimino | 3-methoxy-methyl-isoxazol-5-yl | H |
| IX-7 | diphenyl-acetyl | 2-(N-methyl)-carbonylimino | 3-methoxy-methyl-isoxazol-5-yl | H |
| IX-8 | cyclohexyl-phenyl-methyl | 2-(N-methyl)-carbonylimino | 3-methoxy-methyl-isoxazol-5-yl | H |
| IX-9 | dibenzo-suberane-5-yl | 2-iminocarbonyl | 3-methoxy-methyl-isoxazol-5-yl | H |
| IX-10 | diphenyl-methyl | 2-iminocarbonyl | 3-methoxy-methyl-isoxazol-5-yl | H |
| IX-11 | diphenyl-acetyl | 2-iminocarbonyl | 3-methoxy-methyl-isoxazol-5-yl | H |
| IX-12 | cyclohexyl-phenyl-methyl | 2-iminocarbonyl | 3-methoxy-methyl-isoxazol-5-yl | H |
| IX-13 | dibenzo-suberane-5-yl | 2-(N-methyl)-iminocarbonyl | 3-methoxy-methyl-isoxazol-5-yl | H |
| IX-14 | diphenyl-methyl | 2-(N-methyl)-iminocarbonyl | 3-methoxy-methyl-isoxazol-5-yl | H |
| IX-15 | diphenyl-acetyl | 2-(N-methyl)-iminocarbonyl | 3-methoxy-methyl-isoxazol-5-yl | H |
| IX-16 | cyclohexyl-phenyl-methyl | 2-(N-methyl)-iminocarbonyl | 3-methoxy-methyl-isoxazol-5-yl | H |
| IX-17 | diphenyl-methyl | 2-carbonylimino | 5-methyl-isoxazol-3-yl | H |
| IX-18 | dibenzo-suberane-5-yl | 2-carbonylimino | 5-methyl-isoxazol-3-yl | H |

-continued

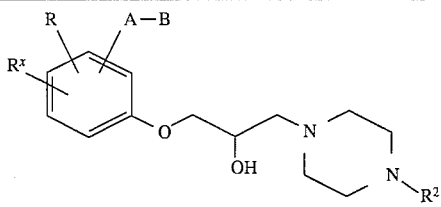

| Example No. | $R^2$ | A | B | R = $R^x$ |
|---|---|---|---|---|
| IX-19 | bis(4-fluor-phenyl)-methyl | 2-carbonylimino | 5-methyl-isoxazol-3-yl | H |

Specific examples of type IX with Z=Z–2 include:

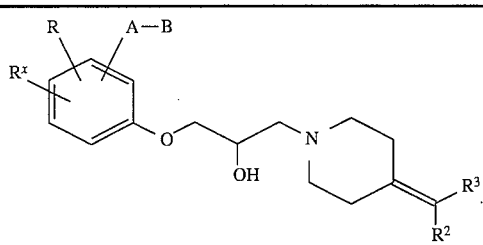

| Example No. | $R^2 = R^3$ | A | B | R = $R^x$ |
|---|---|---|---|---|
| IX-20 | phenyl | 2-carbonylimino | 3-methoxymethyl-isoxazol-5-yl | H |
| IX-21 | phenyl | 2-(N-methyl)-carbonylimino | 3-methoxymethyl-isoxazol-5-yl | H |
| IX-22 | phenyl | 2-iminocarbonyl | 3-methoxymethyl-isoxazol-5-yl | H |
| IX-23 | phenyl | 2-(N-methyl)-iminocarbonyl | 3-methoxymethyl-isoxazol-5-yl | H |
| IX-17 | phenyl | 2-carbonylimino | 5-methyl-isoxazol-3-yl | H |

The compounds of the present invention were prepared according to the following schemes and descriptions:

Scheme I)

a) A compound represented by the general formula I (with A, B, Z, R and $R^x$ in the meaning as defined above; X=OH) is prepared by reaction of an amine Z—H (Z in the meaning as described above) with a glycidether of formula Ia in a suitable solvent, if necessary in the presence of a base.

Suitable solvents are organic solvents such as aliphatic alcohols (like methanol, ethanol, n- and isopropanol); linear dialkyl- and dialkylglycolethers (like diethylether, methyl-tert.-butylether), cyclic ethers (such as tetrahydrofuran, dioxane); aliphatic and aromatic hydrocarbons or their halogenated derivatives (pentane, hexane, heptane, cyclohexane, dichloromethane, trichloromethane, benzene, toluene, xylene, chlorobenzene); aliphatic ketones (acetone, methylethylketone, methylisobutylketone); dialkylform- and dialkyl-acetamides (such as dimethylformamide, dimethylacetamide), dimethylsulfoxide, cyclic ureas (such as 1,3-dimethyl-tetrahydro-2[1H]-pyrimidone), acetonitrile, $H_2O$ and mixtures of the here mentioned solvents. The reaction can be run at room temperature or elevated temperature preferably at the boiling point of the applied solvent or solvent system. The above mentioned base can be an alkalimetal-hydroxide, -carbonate, -hydrogencarbonate, -alcoholate (especially -methylate,-ethylate and -tert.butylate), or a tertiary amine like a trialkylamine, N-alkylmorpholine, pyridine, dimethylaminopyridine or diazabicycloundecane.

Amines like Z—H (with Z in the meaning as defined above) are generally known, and are either commercially available or can be prepared according to standard methods described in the literature (e.g. EP 363 212).

Compounds represented by the general formula I are prepared from glycidethers Ia by reaction with equimolar amounts or excess up to two equivalents of an amine Z—H in a polar aprotic solvent, preferably in alcohols, especially preferred are ethanol or isopropanol, if necessary in the presence of a base, especially potassium carbonate or N-methylmorpholin, and under stirring at elevated temparatures.

Glycidethers of the general formula Ia (with A, B, R, $R^x$ in the meaning as described above) are obtained by alkylation of the corresponding phenols Ib (with A, B, R in the meaning as described above) with epihalohydrins (e.g. epibromo-, epichloro-, epiiodohydrine), 1,3-dihalogen-2-propanols (e.g. 1,3-dibromo- or 1,3-dichloro-2-propanol), or the corresponding glycidtosylates or -mesylates, in the presence of a base.

These reactions are carded out at 0° C. or elevated temperatures up to 120° C. at atmospheric pressure or elevated pressure in an autoclave. Suitable solvents for these reactions are aliphatic ketones (like acetone, methylethylketone, methylisobutylketone), aliphatic alcohols (like methanol, ethanol, n- and isopropanol), aliphatic dialkylethers or cyclic ethers (like diethylether, tetrahydrofuran, dioxane), polar aprotic solvents like dialkylform- or -acetamides (e.g. dimethylformamide, dimethylacetamide), dimethylsulfoxide, nitromethane, hexamethylphosphoric triamide, cyclic ureas (such as 1,3-dimethyl-tetrahydro-2[1H]-pyrimidone); mixtures of the above mentioned solvents or an excess of the alkylating agent. The reaction should be carded out in the presence of base as acid scavenger, e.g. alkalimetal-carbonates (preferably from sodium or potassium), -hydrogencarbonates, -hydroxides, -hydrides, -alcoholates; basic oxides like aluminum- or calcium-oxide; basic ion exchange resins; tertiary amines such as trialkylamines, N-alkylmorpholines or piperidine. The addition of a crown ether (like 18-crown-6) or a phase transfer catalyst (like "Aliquat 336" or triethylbenzylammoniumchloride) may be useful to increase the yield of the reaction as well as addition of a catalytic amount of alkalimetall iodide (especially sodium or potassium iodide).

Compounds represented by the general formula Ia are obtained preferably by reaction of the corresponding phenols Ib with equmolar amounts or in excess with up to two equivalents of epibromo- or epichlorohydrine and 1.0–1.3 equivalents of sodium hydride or potassium tert.butylate in tetrahydrofuran or dimethylformamide, 1–2 equivalents of potassium carbonate in acetone, methylisobutylketone or dimethylformamide at a temperature of 0° C. up to elevated temperatures like 100° C.

b) An alternative method for the synthesis of compounds represented by formula I is the reaction of phenols Ib (with A, B, R, $R^x$ in the meaning as defined above) with a compound represented by formula Ic (where Z is an amine residue as defined above), wherein D means the residues [—$CH_2$—(CH)—O—($CH_2$)] or [—$CH_2$—CHOH—$CH_2$—E], wherein E means a general "leaving group". The reaction can be carried out using the same reaction conditions as described above for the conversion of Ia to I. The leaving group E in formula Ic can mean a halogen radical like chloro, bromo, iodo, an aromatic or aliphatic sulfonic acid residue (like p-toluenesulfonate, p-bromo- or p-nitrobenzenesulfonate, methanesulfonate or trifluoromethanesulfonate). In order to prepare compounds represented by the general formula I, the precursor Ic can also be used as a mixture of the corresponding epoxides and epihalohydrines, if the preparation of Ic affords such mixtures.

c) A compound represented by formula Ic (with Z, D, E in the meaning as described above) is obtained by reaction of an amine Z—H with an epihalohydrine (e.g. epibromo-, epichloro-, epiiodohydrine), 1,3-dihalogen-2-propanols (e.g. 1,3-dibromo- or 1,3-dichloro-2-propanol), or the corresponding glycidtosylates or -mesylates, optionally in the presence of an additional base. The reaction conditions applicable to this step are generally known and are described for example in U.S. Pat. No. 4,980,351.

d) The compounds represented by formula I (with A, B, Z, R, $R^x$ in the meaning as definded above; X═OH) are converted into their corresponding esters Id (with A, B, R, $R^x$, Z in the meaning as described above, X is OC(═O)$R^1$, wherein $R^1$ is defined as in general formula 1) by reaction of compound I with an acid derivative $R^1$CO—G Ie. G can be a general leaving group, preferably a halogen radical (like chlorine, bromine, iodine) or an azide. Ie may also represent a symmetric or asymmetric anhydride with G in the meaning of $R^1$COO or $R^{1*}$COO respectively (with $R^{1*}$ in the meaning of lower alkyl); an "active ester" (with G in the meaning of N-hydroxysuccinimidyl-, imidazolidyl-, N-hydroxybenzotriazolyl-, pentafluorphenyl-residue; examples are given in M. Bodanszky's "Principles of Peptide Synthesis", p. 28–35, Springer Verlag 1984). In case of G in the meaning of OH the use of a dehydrating agent is necessary, such as a carbodiimide (e.g. dicyclohexylcarbodiimide, N,N-diisopropyl-ethylaminocarbodiimide), or other suitable agents generally used for ester formation. The reaction is usually run in an inert organic solvent, the addition of a base might be necessary depending on the nature of the leaving group G. The reaction conditions applicable to this step are generally known and described for example in J. March's "Advanced Organic Chemistry", 3rd edition, p.348–353, (John Wiley and Sons) and the literature cited therein. Precursors and other reagents are commercially available or can be prepared by known methods.

Scheme II)

a) Compounds represented by the general formula II (with A, B, Z, R, $R^x$ in the meaning as described above) are prepared by reaction of an amine Z—H (Z in the meaning as described above) with a compound represented by formula IIa (with A, B, R, $R^x$ in the meaning as described above) in a suitable solvent in the presence of a base. The leaving group E in formula IIa can be a halogen radical like chlorine, bromine or iodine, an aromatic or aliphatic sulfonic acid residue (like p-toluenesulfonate, p-bromo- or p-nitrobenzenesulfonate, methanesulfonate or trifluoromethanesulfonate).

Suitable solvents are organic solvents such as aliphatic alcohols (like methanol, ethanol, n- and isopropanol); linear dialkyl- and dialkylglycolethers (like diethylether, methyltert.-butylether), cyclic ethers (such as tetrahydrofuran, dioxane); aliphatic and and aromatic hydrocarbons or their halogenated derivatives (such as pentane, hexane, heptane, cyclohexane, dichloromethane, trichloromethane, benzene, toluene, xylene, chlorbenzene); aliphatic ketones (acetone, methylethylketone, methylisobutylketone); dialkylform- and dialkylacetamides (such as dimethylformamide, dimethylacetamide), dimethylsulfoxide, nitromethane, hexamethylphosphoric triamide, cyclic ureas (such as 1,3-dimethyltetrahydro-2[1H]-pyrimidone), water and mixtures of the above mentioned solvents. The reaction should be carried out in the presence of base as acid scavenger, e.g. alkalimetal-carbonates (preferably sodium or potassium carbonate), -hydrogencarbonates, -hydroxides, hydrides, alcoholates; basic oxides like aluminum- or calcium-oxide; basic ion exchange resins, tertiary amines such as trialkylamines, N-alkylmorpholines or piperidine. The addition of a crown ether (like 18-crown-6) or a phase transfer catalyst (like "Aliquat 336" or triethylbenzylammoniumchloride) may be useful to increase the yield of the reaction as well as addition of a catalytic amount of alkalimetall iodide (especially sodium or potassium iodide). The reaction can be carried out at a temperature of −10° C. or elevated temperatures up to the boiling point of the solvent or solvent system.

Compounds represented by the general formula II are preferably prepared by reaction of compounds IIa (with A, B, R, $R^x$ with the meaning as described above and E preferably in the meaning of a halogen radical like chlorine, bromine, iodide) with an amine Z—H (with Z in the meaning as described above) at a temperature range from 0° C. up to 80° C. using equimolar amounts or an excess of potassium carbonate or N-methylmorpholin as base, in an alcohol, preferably ethanol or isopropanol, or dimethylformamide as solvent.

Compounds represented by formula IIa (with A, B, R, $R^x$, E in the meaning as described above) are obtained by alkylation of phenol Ib with 1,3-dihalopropanes (such as 1,3-dibromo-, 1,3-dichloro or 1-bromo-3-chloropropane) or their corresponding tosylates or mesylates (such as 3-halopropyltosylate or -mesylate) in the presence of a base using a suitable solvent. The reaction is carried out according to the alkylation of IIa to II applying similar reaction conditions (solvents, base, additives and temperatur range).

Compounds represented by the general formula IIa are preferably prepared from compounds IIb (with A, B, R, $R^x$ in the meaning as described above) by alkylation with equimolar amounts or an excess of 1,3-dibromopropane or 1,3-dichloropropane and 1.0–1.3 equivalents of sodium hydride or potassium tert.butylate in tetrahydrofuran or dimethylformamide, 1–2 equivalents of potassium carbonate in acetone, methylisobutylketone or dimethylformamide at a temperature range from 0° C. or elevated temperatures up to 70° C.

b) Another method for the preparation of compounds represented by formula II (with A, B, Z, R, $R^x$ in the meaning as described above) is the reductive alkylation of an aldehyde IIb (with A, B, R, $R^x$ in the meaning as described above) with an amine Z—H (with Z in the meaning as described above) in the presence of a reducing agent like hydrogen (or any hydrogen source such as ammonium-formate, hydrazine, diimine) and a hydrogenation catalyst (heterogenous or homogeneous), sodium cyanoborohydride, sodium borohydride or formic acid. This type of reaction is well known, the reagents and reaction conditions applicable are described for example in J. March's "Advanced Organic Chemistry", 3rd edition, p.798–800, (John Wiley and Sons) and the literature cited therein.

Aldehydes represented by general formula IIb (with A, B, R, $R^x$ in the meaning as described above) is obtained by alkylation of phenols Ib (with A, B, R, $R^x$ in the meaning as described above) with a compound E—(CH$_2$)$_2$—CHO in the presence of a base in a suitable solvent (with E in the meaning of a general leaving group as mentioned above, preferably a halogen radical like chlorine and bromine). The reaction can be carried out according to the synthesis of IIa.

c) A third method for the preparation of compounds represented by formula II (with A, B, Z, R, $R^x$ in the meaning as described above) can be the reaction of a phenol Ib (with A, B, R, $R^x$ in the meaning as described above) with a compound represented by formula IIc (with Z in the meaning as defined above) in a suitable solvent. In case that E means a general leaving group like a halogen radical (such as chlorine, bromine, iodine), an aromatic or aliphatic sulfonic acid residue (like p-toluenesulfonate, p-bromo- or p-nitrobenzenesulfonate, methanesulfonate or trifluoromethanesulfonate), the conversion represents a simple alkylation of phenol Ib which has been mentioned and described above.

If E means a hydroxy group, the reaction is carried out by using dehydrating agents (for example according to the so-called "Mitsunobu" reaction, using triphenylphosphine and a dialkylazodicarboxylate, preferably diethyldiazocarboxylate; a description of the reaction and the conditions applicable is given for example in Synthesis 1981, p.1–28 and the literature cited therein), at a temperature in the range of 0° C. to room temperature.

Compounds represented by formula IIc (with Z, E in the meaning as mentioned above) are prepared by alkylation of an amine Z—H (with Z as above) with 1,3-dihalopropanes such as 1,3-dichloro-, 1,3-dibromo- or 1-bromo-3-chloropropane, which are commercially available, in the presence of a base using a suitable solvent. The reaction is run according to the synthesis of II from IIa applying the same reaction conditions as described above.

Scheme III)

a) Compounds represented by the general formula III (with B, Z, R, $R^x$, $R^8$ as described for formula 1; X=OH) are prepared according to the methods already described above (scheme I) for the synthesis of compounds such as formula I using intermediates like IIIa or IIIg as precursor. Compounds of formula IIIg are already known and are prepared as described in DE 30 06 351.

Compounds represented by the general formula IIIa (with B, R, $R^x$, $R^8$ in the meaning as described above) are already known and can be prepared by a Wittig or a Wittig-Horner reaction of heterocyclic phosphonates IIIc (with $R^9$=aryl, O-alkyl) or heterocyclic phosphoniumylides IIIc' (with $R^9$=aryl) with the corresponding carbonyl compounds represented by formula IIIb (with R, $R^x$, $R^8$ in the meaning as described above). Both types of reaction are generally known and are carried out according to standard methods, for example the Wittig-Horner reactions using a phosphonate like IIIc according to Houben-Weyl's "Methoden der Organischen Chemie", Vol. 5/1b, p.395–401, the Wittig reaction using a phosphoniumylide such as IIIc' according to Houben-Weyl's "Methoden der Organischen Chemie", Vol. 5/1 b, p. 383–394. Examples for the preparation of compounds represented by formula III with $R^8$=H are given in DE 30 06 351, compounds with $R^8$=alkyl can be prepared according to these methods.

The compounds represented by formula IIIa are usually obtained as mixtures of the corresponding Z- and E-isomers referred to the C=C double bond, the E/Z-ratio usually depends on the method applied (Wittig or Wittig-Horner reaction). The isomers can be separated by column chromatography on silica gel or crystallization in appropriate solvents. Generally Z-isomers, or E/Z-mixtures, can be isomerized photochemically or by treatment with catalytic amounts of iodine in a suitable solvent to afford the pure E-isomers. The reaction is run at a temperature in the range from 0° C. or at elevated temperature up to the boiling point of the solvent applied. Suitable solvents are inert organic solvents such as aliphatic and cyclic ethers (diethylether, diisopropylether, methyl-tert.butylether, tetrahydrofuran, dioxane); aliphatic and aromatic hydrocarbons or their halogenated derivatives (like pentane, hexane, heptane, cyclohexane, dichloromethane, trichloromethane, benzene, toluene, xylene, chlorbenzene). E/Z-mixtures were pereferably converted into pure E-isomers by treating them with catalytic amounts of iodine, preferably using an aliphatic ether like diethylether, methyl-tert.butylether or an aliphatic hydrocarbon like hexane or heptane at a temperature ranging from room temperature to the boiling point of the solvent applied.

Heterocyclic phosphonates such as compound IIIc ($R^9$= aryl, O-alkyl) are generally known in the literature and can be prepared by standard methods converting the corresponding halogenmethylheterocycles according to Arbusov- or Michaelis-Becker conditions, as for example described in Houben-Weyl's "Methoden der Organischen Chemie", Vol. 12, p.433–453 (special examples are given in EP 34754, DE 30 06 35). Heterocyclic phosphoniumylides such as compound IIIc' are generally known in the literature and can be prepared according to Houben-Weyl's "Methoden der Organischen Chemie", Vol. 12, p.79–90. The halogenmethylheterocycles applied are generally known and either commercialy available or can be prepared according to standard methods described in the literature (examples are given e.g. in DE 27 54 832).

Compounds represented by formula IIIb (with R, $R^x$, $R^8$ in the meaning as described above) are usually obtained by alkylation of the corresponding phenols according to the methods described for the preperation of glycidethers such as formula Ia. Especially the various (2,3-epoxypropoxy)-substituted benzaldehydes and acetophenones are known from the literature (e.g. Angew. Makromol. Chemie, 1968, p. 168–169; DE 32 10 061 ) and can be prepared according to the methods described therein.

Compounds represented by the general formula IIIb are preferably obtained by reaction of the corresponding phenols with equimolar amounts or excess of .of epibromo- or epichlorohydrine with 1.0–1.3 equivalents of sodium hydride or potassium tert.butanolate in tetrahydrofuran or dimethylformamide, 1–2 equivalents of potassium carbonate in acetone, methylisobutylketone or dimethylformamide at a temperature ranging from 0° C. to 70° C.

b) Another method for the synthesis of compounds represented by formula III is by Wittig or Wittig-Horner reaction of a carbonyl compound IIIf (with X, Z, R, $R^x$, $R^8$ in the meaning as described above) with a heterocyclic phosphonate or phosphoniumylide like IIIc or IIIc' according to standard methods as described above. Compounds represented by formula IIIf are known in the literature and can be prepared for example as described DE 22 37 228 or DE 23 27 270.

c) Another method for the preparation of compounds represented by formula IIIa (with B, R, $R^x$ in the meaning as described above), wherein $R^8$ is hydrogen, is the reaction of a formylheterocycle B—CHO (with B in the meaning as described above) with phosphonate IIId (with R in the meaning as described above; $R^9$=O-alkyl) according to Wittig-Horner conditions described above. Formylheterocycles such as B—CHO are either commercially available or can be synthesized by using standard methods generally known.

Compounds IIIa (with B, R, $R^x$ in the meaning as described above), wherein $R^8$ is hydrogen, are preferably prepared by reaction of a compound B—CHO (with B in the meaning as described above) and a phosphonate IIId (with R, $R^x$ in the meaning as described above; $R^9$=O-alkyl) in the presence of a 1–1.3 equivalents of a base such as sodium hydride or potassium tert.butylate at a temperature ranging from 0° C. to elevated temperatures such as 50° C., using polar aprotic solvents like dimethylformamide, dimethylsulfoxide, hexamethylphosphoric triamide, dimethylpropyleneurea or mixtures of the above mentioned solvents.

Compounds represented by general formula IIId (with R, $R^x$ in the meaning as described above; $R^9$=O-alkyl) are prepared by alkylation of the corresponding phenol IIIe (with $R^9$ in the meaning as described above) applying the same methods as described above for several other glycidethers like Ia and IIb.

Compounds represented by formula IIIe are obtained by Arbusov-reaction of the corresponding hydroxybenzylalcohols with a trialkylphosphite such as triethylphosphite at elevated temperatures in an inert organic solvent according to the literature mentioned above.

Compounds like IIIe are preferably prepared by reaction of a hydroxybenzylalcohol with excess of trialkylphosphite, such as triethylphosphite, at elevated temperatures ranging from 100° to 140° C. in a polar aprotic solvent like dimethylformamide, dimethylsulfoxide, or 1,3-dimethyl-tetrahydro-2[1H]-pyrimidone.

d) Another method for the preparation of compounds III (with B, X, Z, R, $R^x$ in the meaning as described above, $R^8$=H) is a Wittig-Horner reaction of a compound such as IIIh (with X, Z, R, $R^x$ and $R^9$ in the meaning as described above) with an aldehyde B—CHO (B in the meaning as mentioned above) according to the methods already mentioned above.

Compounds such as IIIh (with X, Z, R, $R^x$ and $R^9$ in the meaning as described above) are prepared by reaction of a glycidether such as IIId (with R, $R^x$ and $R^9$ in the meaning as described above) with an amine Z—H (with Z in the meaning as definded above) according to the methods already described above.

Scheme IV a) Compounds represented by formula IV (with B, Z, R, $R^x$, $R^8$ in the meaning as described above; X=H) are prepared by standard methods already described for the synthesis of compounds II (scheme II). Compounds represented by the general formula IIIg (with B, R, $R^x$, $R^8$ in the meaning as defined above) are already known and described for example in DE 30 06 351.

Scheme V a) Compounds represented by general formula V (with B, X, Z, R, $R^x$, y, z as described above) are prepared according to the methods already described for compounds I and II (scheme I and scheme II) using precursors Va and Vb.

Compounds Vb (with B, R, $R^x$, $R^{10}$, y, z in the meaning as described above) are obtained by alkylation of the corresponding alcohols with halogenmethylheterocycles in the presence of a base in a suitable organic solvent according to standard procedures generally known.

Compounds Vb (wherein $R^{10}$ means hydrogen, y=0 and z=1) are known and can be synthesized by direct alkylation of the corresponding catechols without the need for any additional protecting group, as described for example in DE 20 45 050 and DE 21 29 803.

Compounds like Vb (with B, R, $R^x$, y, z as described above) are prepared by alkylation of benzylalcohols like Vc, wherein $R^{10}$ means a protecting group suitable for phenols or catechols like an ether (such as methyl-, methoxymethyl-, tetrahydropyranyl-, allyl-, isopropyl-, trimethylsilyl-, tert-.butyldimethyl-ether) or an ester (such as acetyl-, benzoylester). Application and cleavage of such protecting groups as well as the preparation of protected phenols is generally known in the literature, see for example in T. W. Greene, P. G. Wuts, "Protective Groups in Organic Synthesis", p. 143–174, 2nd Edition (J. Wiley and Sons, 1991 ).

Scheme VI)

a) Compounds represented by the general formula VI (with B, Z, R, $R^x$ as defined for formula I; X=OH; a=0–4) are prepared according to the methods already described above (scheme I) using glycidethers VIa or phenols VIb (with a, B, R, $R^x$ as defined above) as precursors.

b) Compounds represented by the general formula VI (with B, Z, R, $R^x$ as defined for formula I; X=OH; a=2) are obtained by hydrogenation of unsaturated compounds such as III (with B, Z, X, R, $R^x$ as defined before, cf. scheme III, and $R^8$=H) or VII (with B, Z, X, R, $R^x$ as defined, cf. scheme VII) in a suitable solvent and in the presence of a homogeneous or heterogeneous catalyst at atmospheric pressure or elevated pressure in an autoclave. The source of hydrogen can be hydrogen itself, hydrides such as boron hydrides, aluminum hydrides, tin hydrides or trialkyl- or triphenylsilanes or diimine,. preferably hydrogen gas. Suitable solvents for the hydrogenation with hydrogen gas are polar solvents such as aliphatic alcohols (such as methanol, ethanol, isopropanol), linear, branched or cyclic ethers (e.g. diethylether, methyl tert. butyl ether, tetrahydrofuran, dioxane), aliphatic or aromatic hydrocarbons and their halogenated derivatives (e.g. heptane, benzene, toluene, dichloromethane), aliphatic ketones (e.g. acetone, methylethylketone), dialkylformamides and dialkylacetamides (e.g. dimethylformamide), dimethylsulfoxide, linear and cyclic amines (e.g. triethylamine, morpholine), acetonitrile, water and mixtures of the here mentioned solvents. The reaction can be catalyzed by homogeneous catalysts such as Wilkinson catalyst, rhodium or iridium salts or by heterogeneous catalysts such as rhodium on aluminum oxide or on charcoal, platinoxide or palladium on charcoal. The reaction can be carried out at temperatures between room temperature and 300° C., preferably between room temperature and 100° C. High pressure can be applied in the range of 1–1000 bar, preferably between 1–10 bar. Methods for hydrogenation of such compounds are described in P. N. Rylander, "Hydrogenation Methods", Academic Press, New York (1985).

c) Compounds represented by the general formula VIa (with a=0–4, B, Z, R, $R^x$ in the meaning as described above) are prepared from the corresponding phenols VIb (with a=0–4, B, Z, R, $R^x$ as defined above) according to the methods already described for compounds Ia (scheme I) or III11 (scheme III).

d) Compounds represented by the general formula VIb (with a=0–4, B, Z, R, $R^x$ in the meaning as described above) are obtained by cleavage of the hydroxy-protecting group $R^{10}$ (with $R^{10}$ in the meaning as described, cf. scheme V) from the compounds VIc (with a=0–4, B, Z, R, $R^x$, $R^{10}$ in the meaning as described above) by the methods already described for the synthesis of compounds Vb (cf. scheme V).

e) Compounds represented by the general formula VIc (with a=0–4, B, Z, R, $R^x$, $R^{10}$ in the meaning as described above; a=0–4) are prepared by cycloaddition reactions of unsaturated compounds VId ( with a=0–4, J=carbon—carbon double or triple bond, carbon-nitrogen double or triple bond), thus generating the heterocycles B such as isoxazoles or oxadiazoles. Suitable solvents for the cycloaddition are organic solvents such as aliphatic alcohols (e.g. methanol, ethanol, isopropanol), linear, branched or cyclic ethers (e.g. diethylether, methyl tert. butyl ether, tetrahydrofuran, dioxane), aliphatic or aromatic hydrocarbons or their halogenated derivatives (e.g. heptane, benzene, toluene, dichloromethane), aliphatic ketones (such as acetone, methylethylketone), alkyl ester (e.g. ethyl acetate), dialkylformamides and dialkylacetamides (e.g. dimethylformamide), dimethylsulfoxide, acetonitrile, water and mixtures of the above mentioned solvents. Isoxazoles are usually prepared by the reaction of in situ generated nitriloxides and substituted alkynes in the above mentioned solvents at temperatures ranging from −50° C. to 150° C. preferably between −20° C. and 40° C. The nitriloxides are generated by dehydrohalogenation of the corresponding α-halo-oximes with bases such as amines (like triethylamine) or alkali carbonates and hydrogen carbonates (sodium carbonate, potassium hydrogen carbonate) or by treatment of nitro-methyl-derivatives with isocyanates (Mukaiyama reaction), as described in Houben-Weyl, "Methoden der organischen Chemie", Vol.E5, p. 1591, Thieme Verlag, Stuttgart. Furthermore one-pot-conversion of oximes to isoxazoles are achieved by using a system of halogenation agent and suitable base such as N-chlorosuccinimide/sodium or potassium hydrogencarbonate or sodium hypochlorite/sodium hydroxide in the presence of the unsaturated compound VId in an inert solvent such as dichloromethane, ethyl acetate or water. Generation of nitriloxides and their conversion to isoxazoles are described in K. B. G. Torsell, "Nitrile Oxides, Nitrones and Nitronates in Organic Synthesis", Verlag Chemie, 1988.

The compounds VId are commercially available or can be prepared according to literature procedures as described e.g. in F. -T. Luo et al., J. Org. Chem. 1992, 57, 2213.

f) Another approach to compounds represented by the general formula VIc (with a=0–4, B, Z, R, $R^x$, $R^{10}$ in the meaning as described above) is the catalyzed or uncatalyzed cross-coupling reaction between an organometallic compound VIe or VIg (with Met=boron, lithium, magnesium, sodium, potassium, zinc, tin, copper) and an electrophilic compound such as organic halide, tosylate, mesylate or triflate in an inert solvent. Suitable solvents are polar aprotic solvents such as linear, branched or cyclic ethers (e.g. diethylether, methyl tert. butyl ether, tetrahydrofuran, dioxane, dimethoxyethane), aliphatic or aromatic hydrocarbons and their halogenated derivatives (e.g. heptane, benzene, toluene, chloroform), dimethylsulfoxide, amides (e.g. dimethylformamide, N-methylpyrrolidone, hexamethyl-phosphoric triamide), cyclic ureas (e.g. 1,3-dimethyl-tetrahydro-2[1H]-pyrimidinon), acetonitrile or mixtures thereof. For legs reactive organometallic compounds catalysis of the reaction is required using catalysts such as palladium (e.g. palladium acetate or tetrakistriphenylphosphinepalladium), copper (e.g. dilithiumtetrachlorocuprate) or nickel reagents (e.g. bis(cyclooctadienyl)nickel). The reaction is usually carried out in the case of reactive organometallic compounds at low temperatures between −100° C. and 50° C., preferably between −78° C. and room temperature, in the case of less reactive compounds between 0° C. and 200° C., preferably between room temperature and 150° C. or at the boiling point of the solvent. General methods for such, often transition metal-catalyzed (Ni, Pd, Cu) reactions are described in "Comprehensive Organic Chemistry", Vol. 3, Chapter 2; Ed. B. M. Trost, (1991).

Thus, metallated phenyl-derivatives VIe (with aa=0; R, $R^x$, $R^{10}$, Met in the meaning as described above) or benzyl-derivatives VIe (with aa=1; R, $R^x$, $R^{10}$, Met in the meaning as described above) react with heterocyclic derivatives VIf (with ab=0 or 1; E, B in the meaning as described above and E in the meaning of a general leaving group as defined before) to VIc in an above mentioned solvent. Correspondingly, metallated heterocycles VIg (with ad=0; B and Met in the meaning as described above) or methylheterocycles VIg (with ad=1; B, Met in the meaning as described above) react with phenylalkyl-derivatives VIh (with ac=0 or 1; R, $R^x$, $R^{10}$ in the meaning as described above, E in the meaning of a general leaving group as described before) to VIc under the conditions described above. The metallation of methylheterocycles has been reported for isoxazoles and other cycles with N, S and O as heteroatom by R. G. Micetich et al., Heterocycles, 1985, 23, 585 (isoxazoles) or B. C. Lipshutz and R. W. Hungate, J. Org. Chem. 1981, 46, 1410 (oxazoles). Furthermore the metallated compounds are conveniently synthesized from the corresponding halides by methods as described in Houben-Weyl "Methoden der organischen Chemie", saturated E 13/1–8, Thieme Verlag, Stuttgart. A convenient approach to 5-tributylstannylisoxazoles VIg (B as isoxazole, ad=0; Met as tributylstannyl) is the [2+3]-dipolar cycloaddition of nitriloxides to tributylstannylacetylen as described e.g. by Y. Kondo et al., Tetrahedron Lett. 1989, 30, 4249 or K. Gothelf et al., Acta Chemica Scand. 1992, 46, 494. Other 5-metallated isoxazoles can be obtained from the stannyl compounds by transmetallation reactions as described e.g. by Seyferth, D. et al. J. Org. Chem. 1959, 1395 or J. Am. Chem .Soc. 1962, 84, 361.

g) The compounds represented by formula VI (with a, B, Z, R, $R^x$ as defined above; X=OH) are converted into their corresponding esters VIi (with a, B, Z, R, $R^x$, $R^1$ in the meaning as described above) using the same methods as described in scheme I for the transformation of I to Id. Scheme VII)

a) Compounds represented by the general formula VII (with B; Z, R, $R^x$ as defined for formula I; X=OH) are prepared according to the methods already described above (scheme I) using compounds VIIa or VIIb as precursors.

b) Compounds represented by the general formula VIIa (with B, R, $R^x$ in the meaning as described above) are prepared from the corresponding phenols VIIb (with B, R, $R^x$ in the meaning as described above) by the same methods already described for the synthesis of compounds Ia (scheme I).

c) Compounds represented by the general formula VIIb (with B, R, $R^x$ in the meaning as described above) are obtained by cleavage of the hydroxy-protecting group $R^{10}$ ($R^{10}$ in the meaning as described above, c.f. scheme V) from the compounds VIe (with B, R, $R^x$, $R^{10}$ in the meaning as described above) by the same methods already described for the synthesis of compounds Vb (scheme V).

d) Compounds represented by the general formula VIIc (with B, R, $R^x$, $R^{10}$ in the meaning as described above) are prepared by catalyzed or uncatalyzed cross-coupling reactions of alkinyl-derivatives with organic electrophiles such as halides, triflates, tosylates or mesylates in the presence of a base in a suitable solvent. Suitable solvents for the cross-coupling reaction are organic solvents such as aliphatic alcohols (such as methanol, ethanol, isopropanol), linear, branched or cyclic ethers (e.g. diethylether, methyl-tert.butylether, tetrahydrofuran, dioxane), aliphatic or aromatic hydrocarbons or their halogenated derivatives (e.g. heptane, benzene, toluene, dichloromethane), aliphatic ketones (e.g. acetone, methylethylketone), amines (e.g. triethylamine, diethylamine, dicyclohexylamine) alkyl ester (e.g. ethyl acetate), heteroaromates (e.g. pyridine), dialkylform- and dialkylacetamides (e.g. dimethylformamide), dimethylsulfoxide or acetonitrile and mixtures thereof. The liquid amines such as triethylamine, diethylamine, morpholine or pyridine can serve as solvent and base at the same time. Other bases used for neutralization of acid, generated during the reaction are alkali carbonates or hydrogencarbonates, phosphates or metal alcoholates. The reaction may be run at temperatures between −20° C. and 200° C., preferably at temperatures between room temperature and 150° C. or at the boiling point of the solvent. The reaction is catalyzed by transition metal catalysts such as palladium acetate or bis(triphenylphosphine)palladium dichloride. Furthermore, if necessary, salts as copper halides or nickel halides are added. Instead of the alkynyl-derivatives also the metallated alkynes can be used (with Met=Li, Mg, Zn, Cu).

The compounds VIIe (with R, $R^x$, $R^{10}$ as described above) are either commercially available or can be prepared acording to published procedures.

Thus, phenyl-ethinyl-derivatives VIIe (with R, $R^x$, $R^{10}$ as defined above) react with compounds VIf (with ab=0; B as defined before, E as a general leaving group as defined before) in a cross-coupling reaction under the conditions described above. The starting phenyl-ethinyl-derivatives VIIe (with R, $R^x$, $R^{10}$ as described above) are obtained by a similiar catalyzed or uncatalyzed cross-coupling reaction of phenyl-derivatives VIId (with R, $R^x$, $R^{10}$ in the meaning as described before, E as a general leaving group as described before) with trimethylsilylacetylene and subsequent desilylation with potassium fluoride or carbonate or with silver nitrate/cyanide. This reaction is carried out as described above. Methods for the cleavage of the silyl group from the triple bond are described in e.g. M. Jung et al., J. Org. Chem. 1987, 52, 1888.

e) Another approach to compounds represented by the general formula VIIc (with B, R, $R^x$, $R^{10}$ in the meaning as described above) is the formal dehydration of ketones VIIIc (with w=0, x=1 or w=1, x=0 and B, R, $R^{10}$ in the meaning as described above), which are prepared according to scheme VIII. Several two-step procedures are known (R. C. Larock, "Comprehensive Organic Reactions", Verlag Chemie (1989), chapter alkynes, p.289 and references) for the conversion of ketones to alkynes, for example via the corresponding enol phosphate. Mukaiyama et al. report an one-step-procedure for the conversion of aryl-methylenketones to phenyl-alkynes (Chem. Lett. 1979, 481) using 2-chloro-3-ethylbenzoxazolium salts and a base in an inert solvent such as dichloromethane. Thus, alkynes VIIc are obtained from the ketones VIIIc by treatment with 2-halo-3-alkyl benzoxazolium salts and two or more equivalents of base such as triethylamine. The reaction is carried out in an inert solvent such as linear, branched or cyclic ethers (such as diethylether, methyl tert. butyl ether, tetrahydrofuran, dioxane), aliphatic or aromatic hydrocarbons or their halogenated derivatives (such as heptane, benzene, toluene, dichloromethane or chloroform) at temperatures between $-30°$ C. and $100°$ C., preferably in a range from room temperature to $80°$ C. or at the boiling point of the solvent.

f) A reliable method for the preparation of compounds represented by the general formula VIIc (with B, R, $R^x$, $R^{10}$ in the meaning as described above) is the double elimination of HL (L=I, Br, Cl) from the dihalocompounds VIIf (with L=I, Br, Cl and B, R, $R^x$, $R^{10}$ in the meaning as described above). The dehydrohalogenation can be carried out with basic reagents such as alkali amides (e.g. sodium or potassium amide), alkali hydroxides (e.g. potassium or sodium hydroxide), or alkali fluorides such as potassium fluoride on aluminum(III)oxide. Addition of crown-ethers such as 18-crown-6 may improve the yield of the reaction. Furthermore, the reaction can be carried out in a two-phase-system of water and an organic solvent as aromatic or nonaromatic hydrocarbons or their halogenated derivatives (e.g. heptane, benzene, toluene, dichloromethane or chloroform) or ethers (e.g. diethylether) under phase transfer catalysis. Suitable catalysts are e.g. tetraalkylammonium halides such as tetrabutylammonium chloride or benzyl trimethylammonium chloride. A survey of methods can be found in R. C. Larock, "Comprehensive Organic Reactions", Verlag Chemie (1989), chapter alkynes, p.289.

The dihalocompounds VIIf are easily obtained by addition of halogen to the alkenes III (with B, R, $R^{10}$ in the meaning as described above), which are prepared according to scheme III. Methods for halogenation of alkenes are found in H. O. House, "Modern Synthetic Methods", 2nd ed, W. A. Benjamin (1972), p. 422.

g) The compounds represented by formula VII (with B, Z, R, $R^x$ as defined above; X=OH) are converted into their corresponding esters VIIh (with B, Z, R, $R^x$, $R^1$ as defined above) using the same methods as described in scheme I for the transformation of I to Id.
Scheme VIII)

a) Compounds represented by the general formula VIII (with w, x=0–2 and provided that w+x is not exceeding 3 and B, Z, R, $R^x$ as defined for formula I; X=OH) are prepared from compounds VIIIa or VIIIb according to the methods already described above (scheme I).

b) Compounds represented by the general formula VIIIa (with w, x, B, R, $R^x$ in the meaning as described above) are prepared from the corresponding phenols VIIIb (with w, x, B, R, $R^x$ in the meaning as described above) by the same methods already described for the synthesis of compounds Ia (scheme I).

c) Compounds represented by the general formula VIIIb (with w, x, B, R, $R^x$ in the meaning as described above) are obtained by cleavage of the hydroxy-protecting group $R^{10}$ ($R^{10}$ in the meaning as described in scheme V) from the compounds VIIIc (with w, x, B, R, $R^x$, $R^{10}$ in the meaning as described above) using the same methods already described for the synthesis of compounds Vb (scheme V).

d) Compounds represented by the general formula VIIIc (with w, x, B, R, $R^x$, $R^{10}$ in the meaning as described above) are prepared by catalyzed or uncatalyzed coupling reactions of carboxyl derivatives VIIId or VIIIf with organometallic compounds VIIIe or VIIIg (with metals such as boron, lithium, magnesium, aluminum, sodium, potassium, zinc, tin, copper) in an inert solvent. Suitable solvents are polar aprotic solvents such as linear, branched or cyclic ethers (such as diethylether, methyl tert. butyl ether, tetrahydrofuran, dioxane, dimethoxyethane), aliphatic or aromatic hydrocarbons or their halogenated derivatives (such as heptane, benzene, toluene, chloroform), dimethylsulfoxide, amides (such as dimethylformamide, N-methylpyrrolidone, hexamethylphosphoric triamide), cyclic ureas (such as 1,3-dimethyl-tetrahydro-2(1H)-pyrimidinon) or acetonitrile. For less reactive organometallic compounds catalysis of the reaction is required using catalysts such as palladium (e.g. palladium acetate or tetrakistriphenylphosphinepalladium), copper (such as dilithiumtetrachlorocuprate) or nickel reagents (such as bis(cyclooctadienyl)nickel). The reaction is usually carried out for reactive organometallic compounds at low temperatures between $-100°$ C. and $50°$ C., preferably between $-78°$ C. and room temperature, for less reactive compounds between $0°$ C. and $200°$ C., preferably between room temperature and $150°$ C. or at the boiling point of the solvent. Thus, carboxyl derivatives VIIId (with x, B in the meaning as described above) react with organometallic compounds VIIIe (with w, Met, R, $R^x$, $R^{10}$ as defined above) with or without catalysts in a solvent mentioned above to give the ketones VIIIc (with w, x, B, R, $R^x$, $R^{10}$ in the meaning as described above). M is a general leaving group, preferably alkoxy (e.g. methoxy or ethoxy), halogen (e.g. chlorine, bromide or iodide), tosylate, mesylate or triflate.

Furthermore, the reaction of compounds such as VIIIf (with w, M, R, $R^x$, $R^{10}$ in the meaning as described above) and VIIIg (with x=0–2 and B, Met in the meaning as described above) provides the ketones VIIIc (with w, x, B, R, $R^x$, $R^{10}$ in the meaning as described above).

d1) Stille et al. reported the palladium-catalyzed cross-coupling reaction of acylchlorides with organotin compounds (J. Org. Chem. 1983,48, 4634). Thus, the above described reactions for VIIIe or VIIIg (with Met=trialkylstannyl and B, R, $R^x$, $R^{10}$ in the meaning as described above) with acid chlorides VIIId (with M=Cl and x, B in the meaning as described above) or VIIIf (with M=Cl and w, R, $R^x$, $R^{10}$ in the meaning as described above) were carried out under palladium-catalysis in solvents such as tetrahydrofuran, chloroform or N-methylpyrrolidone at temperatures in a range from 0° C. to 200° C., preferably from room temperature to 150° C. or at the boiling point of the solvent. Commercially available palladium catalysts such as tetrakistriphenylphosphinepalladium or benzyl-bis(triphenylphosphine)palladium(II)chloride can be used as catalysts for these reactions.

The acid chlorides VIIIe or VIIIf (with M=Cl and B, R, $R^x$, $R^{10}$ in the meaning as described above) are prepared from the corresponding acids by reaction with chlorinating agents, e.g thionyl chloride or phosphorous trichloride as such or in inert solvents such as diethyl ether. Methods for the synthesis of acid chlorides are found in Houben-Weyl, "Methoden der organischen Chemie", Vol. E5, p. 587, Thieme Verlag, 1985. The acids are either commercially available or prepared according to published procedures. The organometallic compounds VIIIe or VIIIg are prepared using the same methods already for the synthesis of the corresponding compounds VIe or VIg (c.f. scheme VI).

d2) The reaction of protected hydroxy benzoates with lithiated methylheterocycles has been described by N. A. Meanwell et al. (J. Med. Chem. 1992, 35, 3483). Thus, hydroxy protected benzoates VIIIf (with M=alkoxy and w, R, $R^x$, $R^{10}$ in the meaning as described above) were converted into the corresponding ketones VIIIc (with w, x, B, R, $R^x$, $R^{10}$ in the meaning as described above) by reaction with compounds VIIIc (with Met=Li and x, B in the meaning as described above). The organolithium compounds VIIIg are prepared using the same methods as for the synthesis of the corresponding compounds VIg (c.f. scheme VI). Low temperatures between −100° C. and 0° C. were used for the coupling reaction to avoid side reactions, preferably −78° C. to −20° C. Suitable solvents are polar aprotic solvents as tetrahydrofuran, diethyl ether, dimethoxyethane, hexamethylphosphoric triamide, 1,3-dimethyl-tetrahydro-2[1H]-pyrimidone or mixtures thereof.

e) The compounds represented by formula VIII (with w, x, B, Z, R, $R^x$ as defined before; X=OH) are converted into their corresponding esters VIIIh (with w, x, B, Z, R, $R^x$, $R^1$ as defined before) using the same methods already described in scheme I for the transformation of I to Id.

Scheme IX)

a) Compounds represented by the general formula IX (with B, Z, R, $R^x$ as defined for formula I; X=OH; A in the meaning of the following amide linkage: $(CH_2)_u$—CO—$NR^8$—$(CH_2)_v$ or $(CH_2)_u$—$NR^8$—CO—$(CH_2)_v$ with u, v=0–2, independently from each other, but u+v not exceeding three, and $R^8$ as defined before) are prepared according to the methods already described above (scheme I) using glycidethers IXa or phenols IXb as precursors.

b) Compounds represented by the general formula IXa (with B, R, $R^x$ in the meaning as described above and A as amide linkage as defined above) are prepared from the corresponding phenols IXb (with B, R, $R^x$ in the meaning as described before and A as amide linkage as defined above) by the same methods already described for the synthesis of compounds Ia (scheme I).

c) Compounds represented by the general formula IXb (with B, R, $R^x$ in the meaning as described before and A as amide linkage as defined above) are obtained by cleavage of the hydroxy-protecting group $R^{10}$ (in the meaning as described above, cf. scheme V) from the compounds IXc (with B, R, $R^x$, $R^{10}$ in the meaning as described above and A as amide linkage as defined above) by the same methods already described for the synthesis of Vb (scheme V).

d1) Compounds represented by the general formula IXc (with B, R, $R^x$, $R^{10}$ in the meaning as described above and A as amide linkage as defined above) are prepared by the reaction of amines IXd (with u, R, $R^x$, $R^{10}$, $R^8$ in the meaning as described above) with the compounds IXe (with v and B in the meaning as described above and Q in the meaning of a general leaving group such as hydroxy, alkoxy, halogen (e.g. Cl, Br, I), tosylate, mesylate or triflate), if necessary in presence of a base or a carboxyl group activating agent. Suitable bases are tertiary amines (e.g. triethylamine), heteroaromates such as pyridine or inorganic bases such as potassium carbonate, sodium hydroxide. Carboxyl group activating agents for the coupling of acids with amines are for example carbodiimide such as cyclohexylcarbodiimide or phosphorus reagents such as N,N'-bis(2-oxo-3-oxazolidinyl)-phosphorylchloride. The reactions are carried out in an inert solvent at temperatures between −50° C. and 160° C. Suitable solvents for the amide fomation are organic solvents such as linear, branched or cyclic ethers (e.g. diethylether, methyl tert. butyl ether, tetrahydrofuran, dioxane), aliphatic or aromatic hydrocarbons or their halogenated derivatives (e.g. heptane, benzene, toluene, dichloromethane), aliphatic ketones (e.g. acetone, methylethylketone), tertiary amines (e.g. triethylamine), alkyl ester (e.g. ethyl acetate), heteroaromates (e.g. pyridine), dialkylformand dialkylacetamides (e.g. dimethylformamide), dimethylsulfoxide, acetonitrile, alcohols, water and mixtures thereof.

A direct route to compounds IXb (with B, R, $R^x$ in the meaning as described before and A as amide linkage as defined above) is the reaction of the non-protected phenolderivatives IXd (with u, R, $R^x$, $R^8$ in the meaning as described above and $R^{10}$=H with the compounds IXe (with v and B in the meaning as described above and Q in the meaning of a general leaving group such as hydroxy, alkoxy, halogen (e.g. Cl, Br, I), tosylate, mesylate or triflate), using the same methods for the formation of the amide bond as described before.

The synthesis of amides is described in Houben-Weyl, "Methoden der organischen Chemie", Vol. E5, Thieme Verlag, 1985.

d2) Compounds represented by the general formula IXc (with B, R, $R^x$, $R^{10}$ in the meaning as described above and A as amide linkage as defined above) are prepared by the reaction of amines IXg (with v, B, $R^8$ in the meaning as described above) with the compounds IXf (with u, R, $R^x$, $R^{10}$ in the meaning as described above and Q in the meaning of a general leaving group such as hydroxy, alkoxy, halogen (e.g. Cl, Br, I), tosylate, mesylate or triflate), if necessary in presence of a base or a carboxyl group activating agent, using the same methods as described before.

e) The compounds represented by formula IX (with B, Z, R, $R^x$ as defined above and A as amide linkage as defined above; X=OH) are converted into their corresponding esters IXh (with B, Z, R, $R^x$ and $R^1$ in the meaning as described before and A as amide linkage as defined above) by the same methods as described in scheme I for the transformation of I to Id.

Generally the compounds of the present invention can be prepared according to standard procedures of organic chemistry. The applied methods should be familiar and available to those who are skilled in the art.

Scheme I
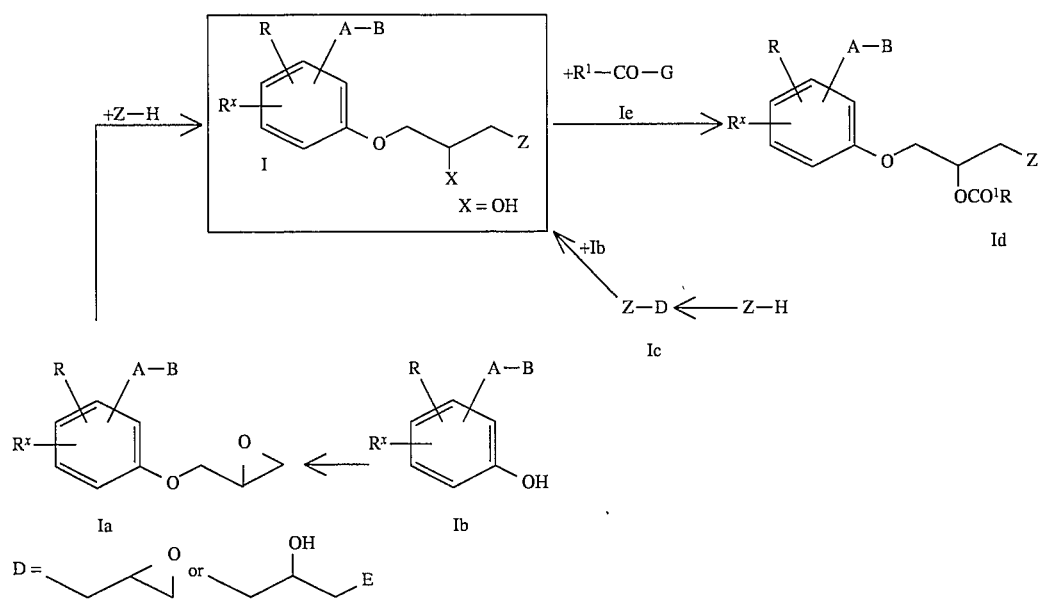
Scheme II
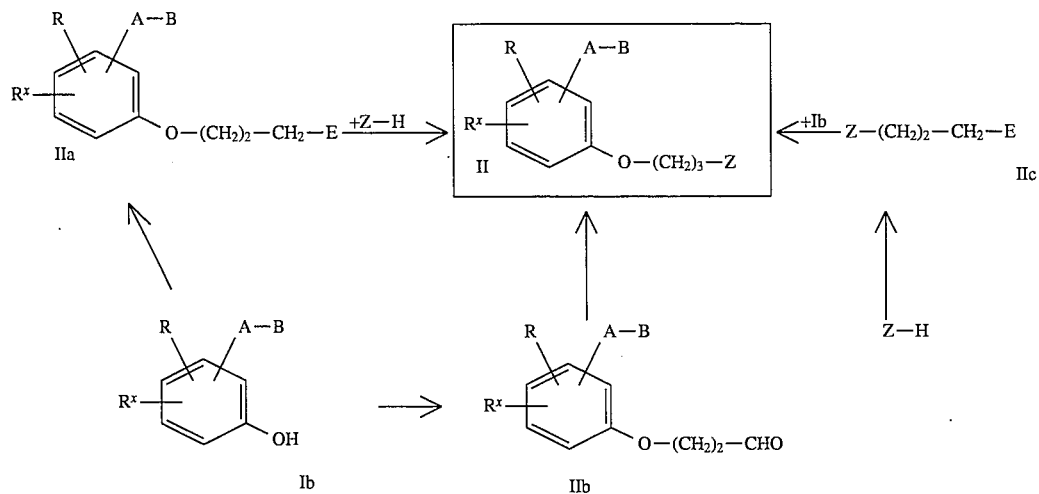

SCHEME III
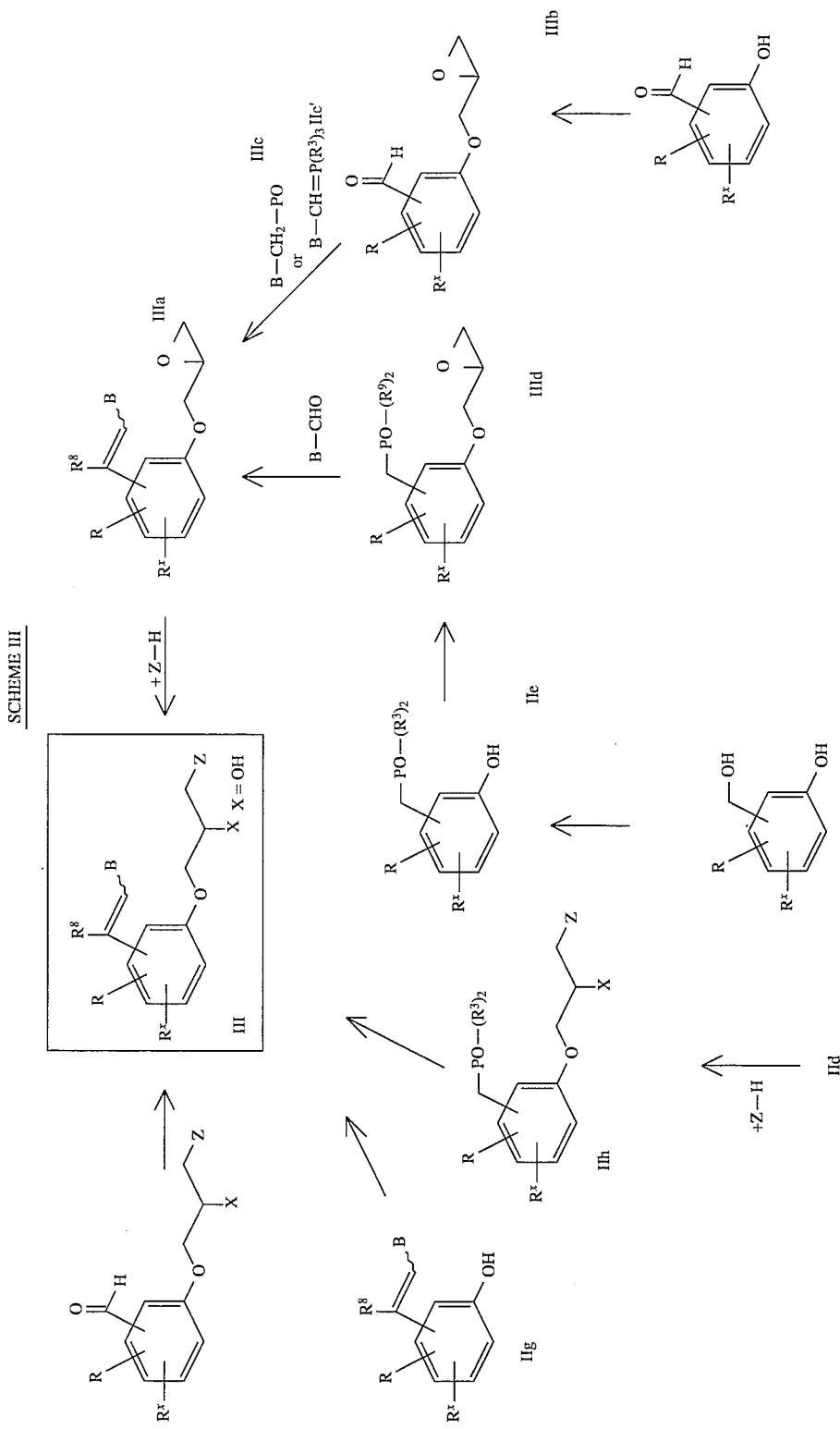

Scheme IV
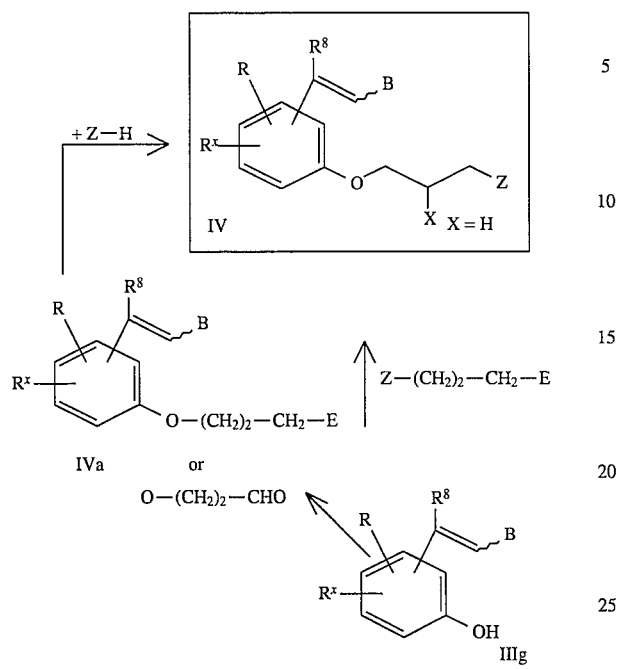
Scheme V
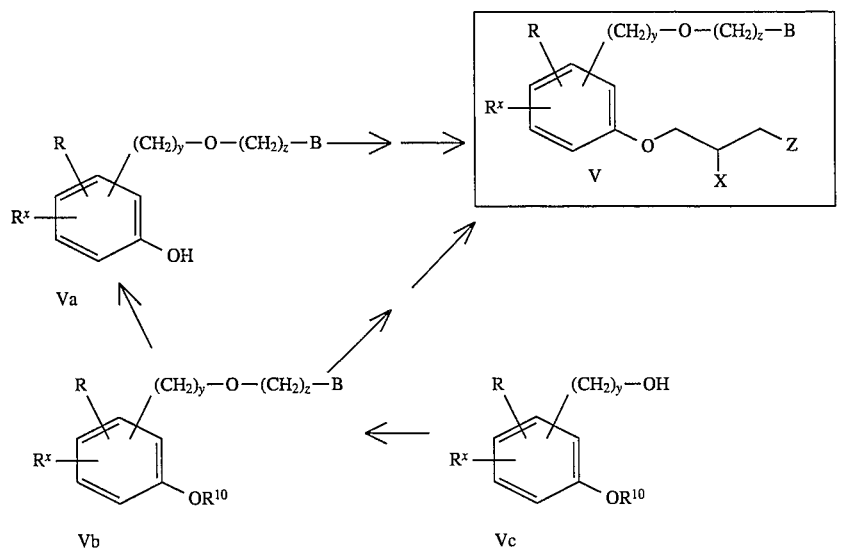

Scheme VI
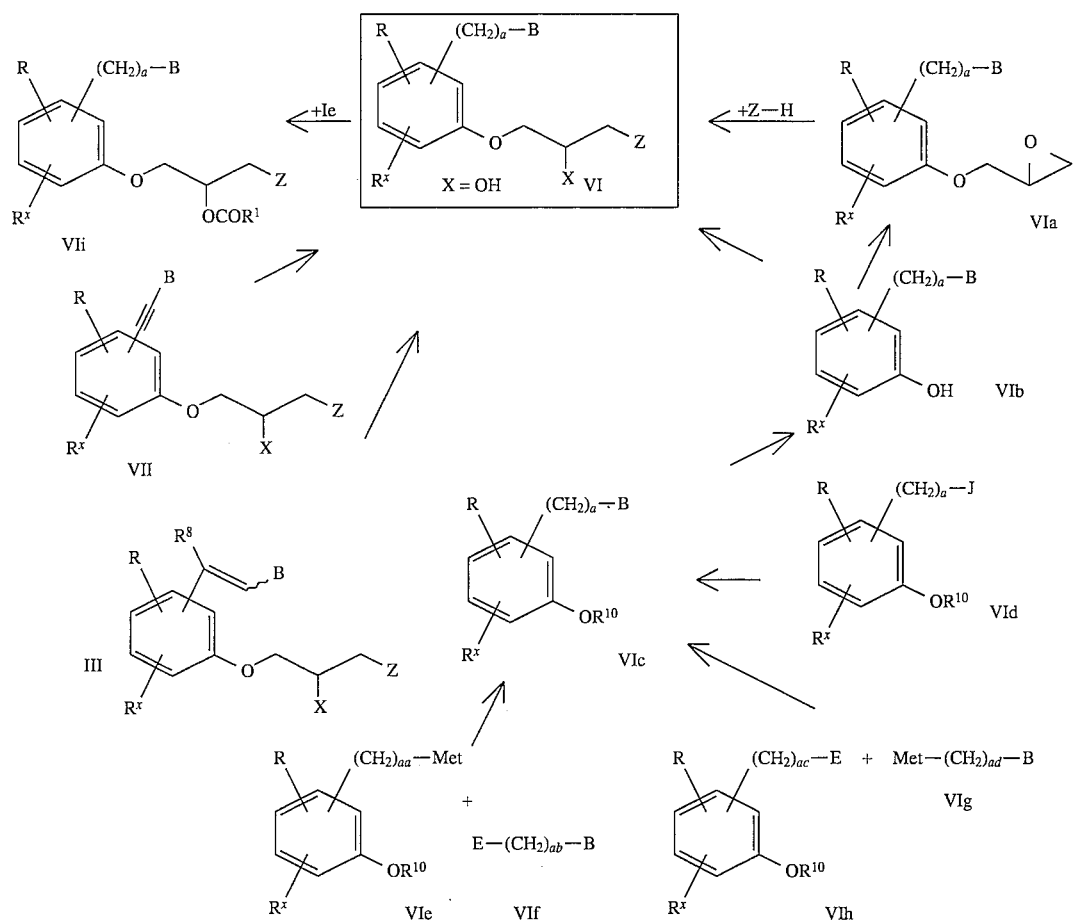
Scheme VII
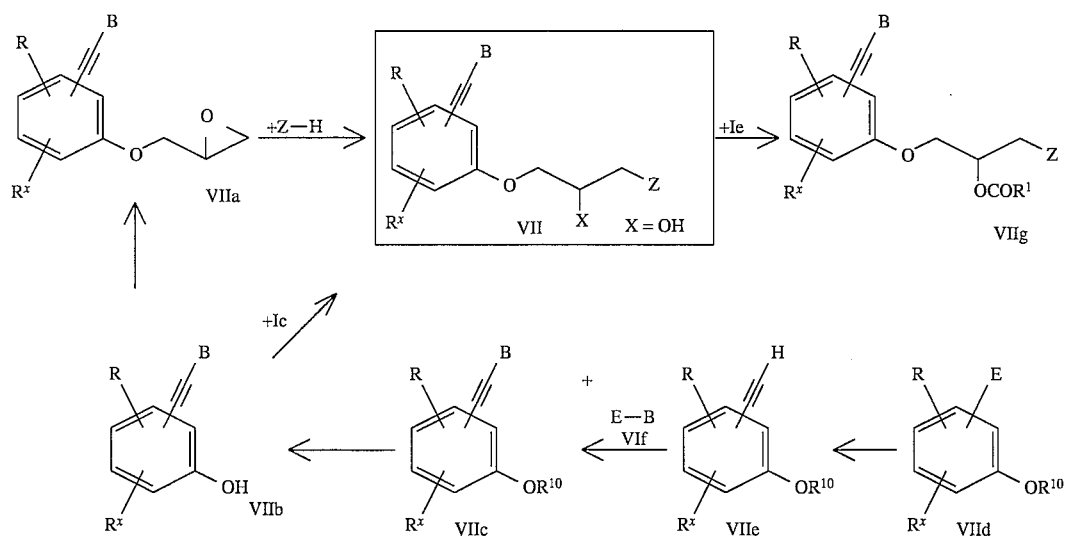

-continued
Scheme VII
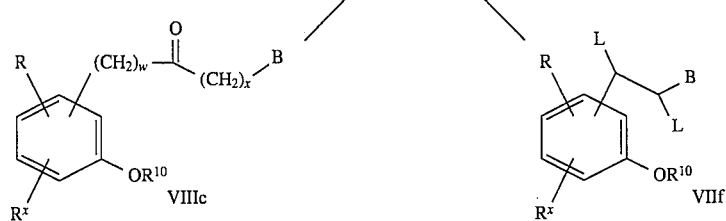
Scheme VIII
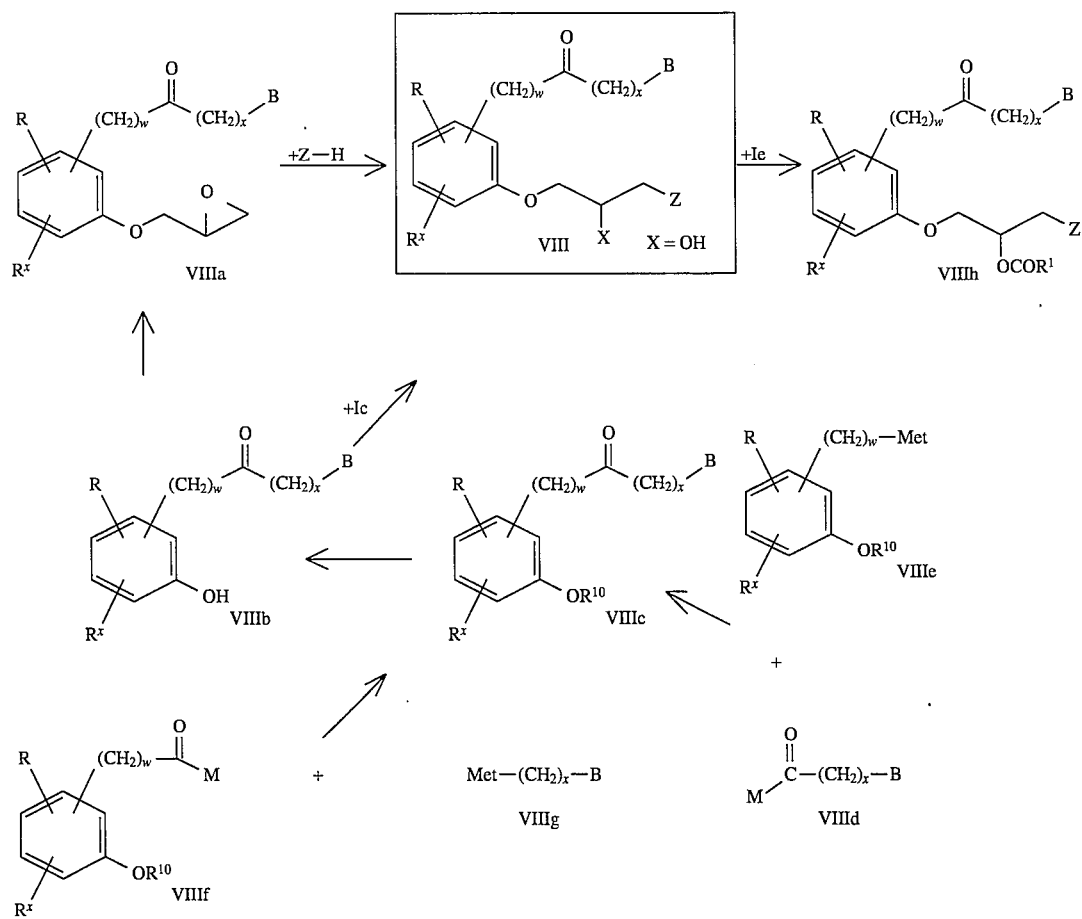

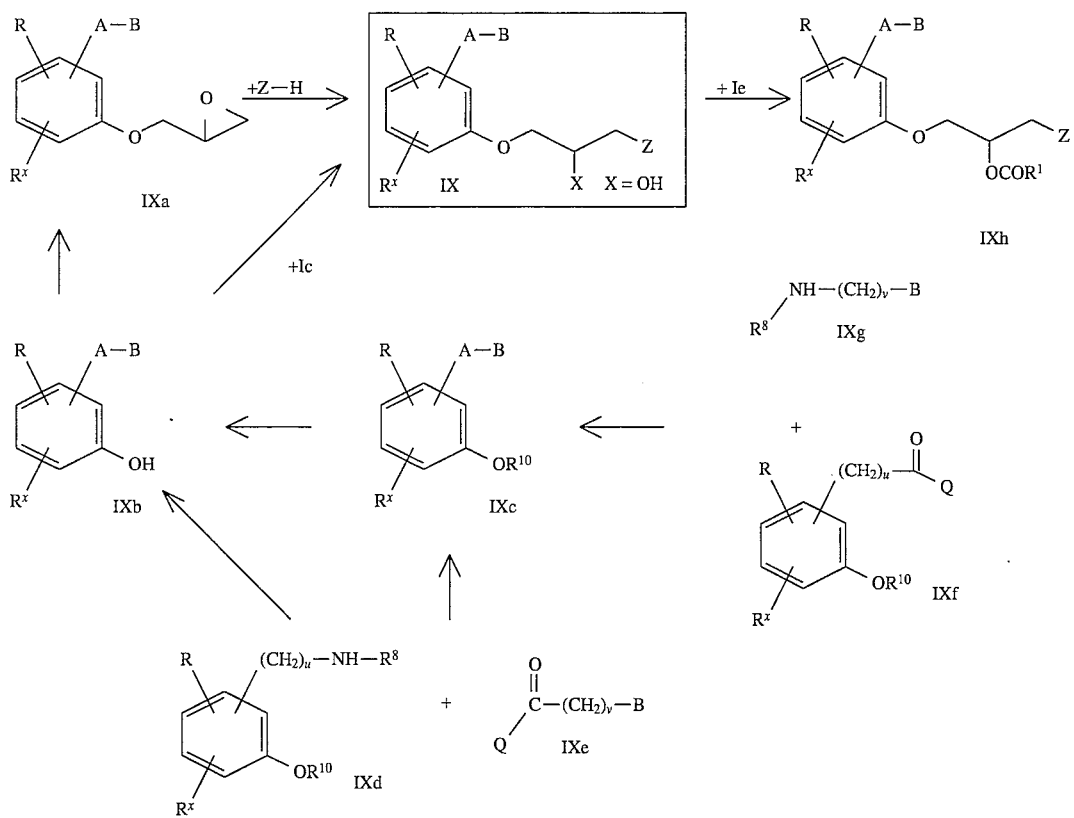

Scheme IX

The present invention is further illustrated by the following examples:

III-1 (E)-1-[10,11-Dihydro-5H-dibenzo[a,d]cyclohepten-5-yl]-piperazin-1-yl]-3-{2-[2-(3-methoxymethyl-isoxazol-5-yl)-ethenyl]-phenoxy}-propan-2-ol 1 g of (E)-5-{2-[2-(2,3-epoxypropoxy)-phenyl]-ethenyl}-3-(methoxymethyl)-isoxazole (precursor IIIa-1) and 0.97 g of (10,11-dihydro-5H-dibenzo[a,d]cyclohepten-5-yl)-piperazine were refluxed in 10 ml ethanol. After completion of the reaction the mixture was stirred at room temperature until a white solid precipitated. Recristallisation of the precipitate from ethanol afforded 1.36 g of the title compound as a white solid.

Mp.:118°–121° C. $^{13}$C-NMR [CDCl$_3$; δ (ppm)]: 31.8, 51.8, 58.8, 60.7, 65.4, 71.0, 79.0, 100.2, 112.6, 113.9, 121.3, 124.8, 125.5, 127.7, 127.8, 130.3, 130.8, 139.2, 139.7, 156.9, 161.7, 169.9

III-2 (E)-1-[4-{Bis(4-methoxphenyl)}-methyl]-piperazin-1-yl]-3-{2-[2-(3-methoxymethyl-isoxazol-5-yl)-ethenyl]-phenoxy}-propan-2-ol The reaction was carried out according to the synthesis of III-1 using bis(4-methoxy-phenyl)-methyl-piperazine and precursor IIIa-1.

Mp.: 123°–126° C. $^1$H-NMR [DMSO, δ (ppm)]: 2.10–2.80 (m, 10H), 3.28 (s, 3H), 3.65 (s, 6H), 3.92–4.20 (m, 4H), 4.45 (s, 2H), 4.80–5.10 (s, 1H), 6.63 (s, 1H), 6.85 (m, 4H), 6.95–7.15 (m, 2H), 7.20–7.40 (m, 6H), 7.55–7.70 (m, 2H)

III-3 (E)-1-[4-(Diphenyl-methyl)-piperazin-1-yl]-3-{4-[2-(3-methoxymethyl-isoxazol-5-yl)-ethenyl]-phenoxy}-propan-2-ol The reaction was carried out as described for III-1 using 4-(diphenyl-methyl)-piperazine and (E)-5-{2-[4-(2,3-epoxypropoxy)-phenyl]-ethenyl}-3-(methoxymethyl)-isoxazole (precursor IIIa-3).

Mp.: 139°–141° C. $^{13}$C-NMR [CDCl$_3$; δ (ppm)]: 52.0, 53.7, 58.5, 60.4, 65.5, 65.9, 70.5, 76.2, 99.9, 111.1, 115.0, 127.0, 128.0, 128.5, 128.6, 134.6, 142.7, 159.7, 161.7, 169.2

III-4 (E)-1-[10,11-Dihydro-5H-dibenzo[a,d]cyclohepten-5-yl]-piperazin-1-yl]-3-{4-[2-(3-methoxymethyl-isoxazol-5-yl)-ethenyl]-phenoxy}-propan-2-ol The reaction was run according to example III-1 using 10,11-dihydro-5H-dibenzo[a,d]-cyclohepten-5-yl-piperazine and precursor IIIa-3.

Mp.: 146°–147° C. $^{13}$C-NMR [CDCl$_3$; δ (ppm)]: 31.8, 52.0, 53.8, 58.5, 60.4, 65.5, 65.9, 70.5, 79.1, 99.9, 111.1, 115.0, 126.5, 127.8, 128.6, 130.8, 134.6, 139.2, 139.7, 159.8, 161.7, 169.2

III-5 (E)-1-[10,11-Dihydro-5H-dibenzo[a,d]cyclohepten-5-yl]-piperazin-1-yl]-3-{2-[2-(3-methyl-isoxazol-5-yl)-ethenyl]-phenoxy}-propan-2-ol The reaction was carried out following the same procedure described for example III-1 using 10,11-dihydro-5H-dibenzo[a,d]cyclohepten-5-yl-piperazine and (E)-5-{2-[2-(2,3-epoxypropoxy)-phenyl]-ethenyl}-3-(methyl)-isoxazole.

Mp.: 167°–168° C. $^{13}$C-NMR [CDCl$_3$; δ (ppm)]: 11.4, 31.8, 51.9, 53.7, 60.7, 65.5, 79.1, 101.8, 112.6, 114.1, 121.2, 125.1, 125.5, 127.8, 129.9, 130.1, 130.8, 139.2, 139.7, 156.9, 160.0, 168.9

III-6 (E)-1-[4-(Diphenyl-methyl)-piperazin-1-yl]-3-{2-[2-(3-methyl-isoxazol-5-yl)-ethenyl]-phenoxy}-propan-2-ol The reaction was carried out following the same procedure described for example III-1 using 4-(diphenyl-methyl)-piperazine and (E)-5-{2-[2-(2,3-epoxypropoxy)-phenyl]-ethenyl}-3-(methyl)-isoxazole.

Mp.: 128°–130° C. $^{13}$C-NMR [CDCl$_3$; δ (ppm)]: 11.5, 52.0, 53.6, 60.7, 65.4, 71.0, 76.2, 101.8, 112.5, 114.1, 121.3, 125.0, 127.0, 127.8, 128.5, 129.8, 130.1, 142.7, 156.9, 160.0, 168.9

III-7 (E)-1-[10,11-Dihydro-5H-dibenzo[a,d]cyclohepten-5-yl]-piperazin-1-yl]-3-{2-[2-(3-carbethoxy-isoxazol-5-yl)-ethenyl]-phenoxy}-propan-2-ol The reaction was carried out according to example III-1 using 10,11-dihydro-5H-dibenzo[a,d]cyclohepten-5-yl-piperazine and (E)-3-(carbethoxy)-5-{2-[2-(2,3-epoxypropoxy)-phenyl]-ethenyl}-isoxazole.

Mp.: 142°–144° C. $^{13}$C-NMR [CDCl$_3$; δ (ppm)]: 14.2, 31.8, 52.0, 53.7, 60.5, 62.1, 71.0, 79.1, 101.1, 112.6, 113.3, 121.3, 124.5, 125.5, 127.7, 129.1, 130.7, 130.8, 131.6, 139.2, 139.7, 156.7, 157.1, 160.1, 171.1

III-8 (E)-1-[4-(Diphenyl-methyl)-piperazin-1-yl]-3-{2-[2-(3-carbethoy-isoxazol-5-yl)-ethenyl]-phenoxy}-propan-2-ol The reaction was carried out following the same procedure described for example III-1 using 4-(diphenyl-methyl)-piperazine and (E)-3-(carbethoxy)-5-{2-[2-(2,3-epoxypropoxy)-phenyl]-ethenyl}-isoxazole.

Mp.: 122°–123° C. $^{13}$C-NMR [CDCl$_3$; δ (ppm)]: 14.2, 52.0, 53.6, 60.7, 62.1, 65.3, 71.0, 76.2, 101.1, 112.5, 121.2, 124.5, 127.0, 128.0, 128.1, 128.5, 130.6, 131.7, 142.7, 156.7, 160.1, 171.1

III-9 (E)-1-[10,11-Dihydro-5H-dibenzo[a,d]cyclohepten-5-yl]-piperazin-1-yl]-3-{3-[2-(3-methoxymethyl-isoxazol-5-yl)-ethenyl]-phenoxy}-propan-2-ol The reaction was carried out following the same procedure described for example III-1 using 10,11-dihydro-5H-dibenzo[a,d]cyclohepten-5-yl-piperazine and epoxide IIIa-2.

Mp.: 109°–110° C. $^{13}$C-NMR [CDCl$_3$; δ (ppm)]: 31.8, 51.9, 58.5, 60.4, 65.5, 65.8, 70.5, 79.1, 100.7, 113.1, 113.5, 120.2, 125.5, 127.8, 129.9, 130.8, 134.8, 137.0, 139.2, 139.7, 159.3, 161.8, 168.8

III-10 (E)-1-[4-(Diphenyl-methyl)-piperazin-1-yl]-3-{3-[2-(3-methoxymethyl-isoxazol-5-yl)-ethenyl]-phenoxy}-propan-2-ol The reaction was carried out following the same procedure described for example III1 using 4-(diphenyl-methyl)-piperazine and epoxide IIIa-2.

$^{13}$C-NMR [CDCl$_3$; δ (ppm)]: 45.8, 48.7, 53.4, 58.6, 60.3, 64.4, 65.8, 70.0, 73.2, 75.2, 101.0, 112.9, 113.6, 115.4, 120.5, 127.5, 127.7, 128.9, 130.0, 134.5, 137.1, 141.4, 158.6, 161.8, 168.7, 174.4, 179.3.

III-11 (E)-1-[10,11-Dihydro-5H-dibenzo[a,d]cyclohepten-5-yl]-piperazin-1-yl]-3-{2-[2-(3-isopropyl-isoxazol-5-yl)-ethenyl]phenoxy}-propan-2-ol The reaction was carried out following the same procedure described for example III-1 using 10,11-dihydro-5H-dibenzo[a,d]cyclohepten-5-yl-piperazine and (E)-5-{2-[3-(2,3-epoxypropoxy)-phenyl]-ethenyl}-3-(isopropyl)-isoxazole.

Mp.: 160°–162° C. $^{13}$C-NMR [CDCl$_3$; δ (ppm)]: 21.8, 26.5, 31.8, 52.0, 53.7, 60.6, 65.4, 71.0, 79.1, 99.2, 112.5, 114.3, 121.2, 125.1, 125.5, 127.7, 129.7, 130.0, 130.7, 130.8, 139.2, 139.7, 156.9, 168.7, 169.6

III-12 (E)-1-[4-(Diphenyl-methyl)-piperazin-1-yl]-3-{2-[2-(3-phenyl-isoxazol-5yl)-ethenyl]-phenoxy}-propan-2-ol The reaction was carried out following the same procedure described for example III-1 using 4-(diphenyl-methyl)-piperazine and (E)-5-{2-[3-(2,3-epoxypropoxy)-phenyl]-ethenyl}-3-(phenyl)-isoxazole.

Mp.: 129°–132° C. $^{13}$C-NMR [CDCl$_3$; δ (ppm)]: 52.0, 53.6, 60.7, 65.5, 71.0, 76.2, 99.0, 112.6, 114.0, 121.2, 124.9, 126.8, 127.0, 127.9, 128.5, 128.9, 129.3, 129.9, 130.3, 142.7, 157.0, 162.7, 169.7

III-13 (E)-1-[10,11-Dihydro-5H-dibenzo[a,d]cyclohepten-5-yl]-piperazin-1-yl]-3-{2-[2-(3-phenyl-isoxazol-5-yl)-ethenyl]-phenoxy}-propan-2-ol The reaction was carried out according to example III-1 using 10,11-dihydro-5H-dibenzo[a,d]cyclohepten-5-yl-piperazine and (E)-5-{2-[3-(2,3-epoxypropoxy)-phenyl]-ethenyl}-3-(phenyl)-isoxazole.

Mp.: 148°–150° C. $^{13}$C-NMR [CDCl$_3$, δ (ppm)]: 31.8, 52.0, 53.7, 60.6, 65.4, 71.0, 79.1, 99.0, 112.6, 114.0, 121.2, 125.5, 126.8, 127.7, 127.8, 128.9, 129.3, 130.3, 130.8, 139.2, 139.7, 157.0, 162.7, 169.7

III-14 (E)-1-[4-{Bis(4-fluorphenyl)-methyl}-piperazin-1-yl]-3-{2-[2-(3methoxymethyl-isoxazol-5-yl)-ethenyl]-phenoxy}-propan-2-ol The reaction was carried out following the same procedure described for example III-1 using epoxide IIIa-1 and bis(4-fluorophenyl)-methyl-piperazine.

Mp.: 110°–112° C. $^{13}$C-NMR [CDCl$_3$; δ 0(ppm)]: 51.8, 53.6, 58.5, 60.7, 65.5, 65.9, 71.0, 100.2, 112.5, 113.9, 115.3, 115.6, 123.3, 124.9, 127.8, 129.2, 129.3, 130.3, 138.2, 156.9, 160.6, 161.7, 163.1, 169.9

III-15 (Z)-1-[4-(Cyclohexyl-phenyl)-methyl]-piperazin-1-yl]-3-{2-[2-( 3-isopropyl-isoxazol-5-yl)-ethenyl]-phenoxy}-propan-2-ol The reaction was carried out following the same procedure described for example III-1 using 4-(cyclohexyl-phenyl)-methyl-piperazine and (Z)-5-{2-[3-(2,3-epoxypropoxy)-phenyl]-ethenyl}-3-(isopropyl)-isoxazole.

$^{13}$C-NMR [DMSO; δ (ppm)] (citrate): 21.4, 25.4, 25.5, 26.3, 29.6, 29.6, 30.4, 36.3, 38.8, 43.5, 47.0, 52.9, 59.5, 63.0, 64.6, 70.8, 71.7, 73.4, 100.1, 112.7, 113.9, 121.0, 124.0, 126.9, 127.4, 127.7, 128.70, 129.0, 130.3, 136.2, 136.2, 156.3, 168.1, 169.2, 171.2, 175.8

III-16 (Z)-1-[4-(2-Hydroxy-3-{2-[2-(3-isopropyl-isoxazol-5-yl)-ethenyl]-phenoxy}-propyl)-piperazin-1-yl]-2,2-diphenyl-ethanone The reaction was carded out following the same procedure described for example III-1 using (Z)-5-{2-[3-(2,3-epoxypropoxy)-phenyl]-ethenyl}-3-(isopropyl)-isoxazole and 2,2-diphenyl-acetyl-piperazine.

$^{13}$C-NMR [DMSO;.δ (ppm)] (citrate): 23.6, 28.0, 43.2, 45.0, 47.0, 54.6, 54.9, 55.2, 62.4, 68.0, 73.3, 74.2, 102.1, 114.8, 116.0, 122.9, 126.0, 128.6, 129.7, 130.2, 130.3, 130.9, 132.4, 142.1, 158.6, 170.2, 171.4, 171.5, 173.3, 177.1.

III-18 (Z)-1-[10,11-Dihydro-5H-dibenzo[a,d]cyclohepten-5-yl]-piperazin-1-yl]-3-{2-[2-(3-methoxymethyl-isoxazol-5-yl)-ethenyl]-phenoxy-}-propan-2-ol The reaction was carried out following the same procedure described for example III-1 using 10,11-dihydro-5H-dibenzo[a,d]cyclohepten-5-yl-piperazine and the crude epoxide III-15a.

$^{13}$C-NMR [DMSO; δ (ppm)] (citrate): 30.9, 43.5, 49.7, 52.7, 57.8, 59.3, 64.7, 64.8, 70.7, 71.7, 77.2, 102.4, 112.1, 114.6, 120.2, 124.5, 125.5, 127.7, 129.3, 130.1, 130.4, 131.7, 138.7, 161.0, 167.4, 171.2, 175.8

III-19 (Z)-1-[4-(Diphenyl-methyl)-piperazin-1-yl]-3-{2-[2-(3-methoxymethyl-isoxazol-5-yl)-ethenyl]-phenoxy}-propan-2-ol The reaction was run according to example III-1 using 4-(diphenyl-methyl)-piperazine and the crude epoxide III-15a.

$^{13}$C-NMR [CDCl$_3$; δ (ppm)] (citrate): 44.5, 48.5, 58.6, 64.2, 65.7, 70.1, 73.1, 75.2, 101.9, 112.1, 115.9, 121.2, 124.9, 127.6, 127.8, 129.8, 130.3, 132.1, 141.1, 155.2, 161.4, 168.3, 173:9, 179.0

III-20 (E)-1-[5H-Dibenzo[a,b]cyclohepten-5-yl]-3-{2-[2-(3-methoxymethyl-isoxazol-5-yl)-ethenyl]-phenoxy}-propan-2-ol The reaction was carried according to example III-1 using 5H-dibenzo[a,d]cyclohepten-5-yl-piperazine and epoxide IIIa-1.

Mp.: 115°–116° C. $^{13}$C-NMR [DMSO; δ (ppm)]: 51.1, 57.8, 60.8, 64.8, 66.2, 71.5, 100.9, 112.5, 113.6, 120.6, 123.8, 126.9, 127.6, 127.9, 129.3, 129.6, 129.8, 130.2, 130.4, 133.9, 137.8, 156.7, 161.5, 168.8

III-21 (E)-1-[4-(2-Hydroxy-3-{3-[2-(3-methoxymethyl-isoxazol-5-yl)-ethenyl]-phenoxy}-propyl)-piperazin-1-yl]-cyclohexyl-phenyl-ethanone The reaction was carried according to example III-1 using 4-(cyclohexyl-phenyl)-methyl-piperazine and epoxide IIIa-2.

$^{13}$C-NMR [DMSO; δ (ppm)] (citrate): 25.5, 25.6, 26.0, 29.8, 31.6, 40.6, 42.9, 44.4, 52.4, 52.8, 53.4, 60.1, 64.8, 65.7, 70.7, 72.1, 101.3, 112.7, 113.6, 115.6, 119.9, 126.5, 128.2, 128.3, 129.8, 134.3, 136.7, 138.8, 158.9, 161.6, 168.3, 170.7, 171.2, 174.9

Ill-22 (E)-1-[4-(Cyclohexyl-phenyl)-methyl-piperazin-1-yl]-3-{2-[2-(3-methoxymethyl-isoxazol-5-yl)-ethenyl]-phenoxy}-propan-2-ol The reaction was carried according to example III-1 using 4-(cyclohexyl-phenyl)-methyl-piperazine and epoxide IIIa-1.

$^{13}$C-NMR [DMSO; δ (ppm)] (citrate; mixture of E- and Z-Isomers 7.3): 25.4, 25.5, 26.3, 29.6, 30.4, 36.4, 43.7, 47.1, 52.9, 53.1, 57.9, 59.4, 59.7, 64.7, 64.9, 65.0, 70.6, 71.0, 71.6, 73.5, 101.0, 102.4, 112.2, 112.7, 113.7, 114.6, 120.3, 120.9, 123.9, 124.5, 126.8, 127.6, 129.0, 129.4, 130.1, 130.5, 131.7, 136.4, 155.9, 156.4, 161.0, 161.6, 167.4, 168.8, 171.2, 176.1

III-23 (E)-1-[4-(Cyclohexyl-phenyl)-methyl-piperazin-1-yl]-3-{2-[2-(3-phenyl-isoxazol-5yl)-ethenyl]-phenoxy}-propan-2-ol The reaction was carried according to example III-1 using 4-(cyclohexyl-phenyl)-methyl-piperazine and (E)-5-{2-[3-(2,3-epoxypropoxy)-phenyl]-ethenyl}-3-(phenyl)isoxazole.

$^{13}$C-NMR [CDCl$_3$; δ (ppm)] (citrate; mixture of E- and Z-lsomers 1:1): 26.3, 26.5, 26.9, 29.7, 29.7, 31.2, 37.7, 49.6, 53.9, 60.9, 65.5, 71.1, 99.0, 112.6, 114.1, 121.2, 125.0, 125.3, 126.8, 127.2, 127.7, 128.0, 128.3, 128.9, 129.1, 129.3, 129.4, 129.9, 130.3, 130.4, 137.8, 157.0, 162.7, 169.8

III-24 (E)-1-[4-(Diphenyl-methyl)-piperazin-1-yl]-3-{2-[2-(3-methoxymethyl-isoxazol-5-yl)-ethenyl]-phenoxy}-propan-2-ol The reaction was carried out following the same procedure described for example III-1 using 4-(diphenyl-methyl)-piperazine and epoxide IIIa-1.

$^{13}$C-NMR [DMSO, δ (ppm)](citrate): 43.5, 49.8, 52.7, 57.8, 59.6, 64.8, 71.0, 71.7, 74.4, 101.0, 112.7, 113.6, 120.9, 123.8, 126.9, 127.4, 127.5, 128.5, 129.3, 130.5, 142.3, 156.4, 161.5, 168.8, 171.2, 175.7

III-25 (E)-1-[4-(Diphenyl-methyl)-piperazin-1-yl]-3-{2-[2-(3-methoxymethyl-isoxazol-5-yl)-ethenyl]-4,5-dimethoxy-phenoxy}-propan-2-ol The reaction was carried out following the same procedure described for example III-1 using 4-(diphenyl-methyl)-piperazine and IIIa-12.

Mp.: 114°–115.5° .C $^{13}$C-NMR [CDCl$_3$; δ (ppm)]: 52.0, 53.6, 56.1, 58.5, 60.6, 65.5, 65.9, 72.6, 76.2, 99.4, 99.5, 109.9, 111.5, 126.99, 128.0, 128.5, 129.8, 142.5, 144.0, 151.1, 152.2, 161.7, 169.9

III-26 (E)-1-[4-(Diphenyl-methyl)-piperazin-1-yl]-3-{2-[2-(3-methoxymethyl-isoxazol-5-yl)-ethenyl]-5-N,N-diethylamino]-phenoxy}-propan-2-ol The reaction was carried out following the same procedure described for example III-1 using 4-(diphenyl-methyl)-piperazine and epoxide IIIa-13.

$^{13}$C-NMR [DMSO; δ (ppm)] (citrate): 12.5, 43.5, 43.7, 49.9, 52.8, 57.8, 59.9, 64.8, 64.9, 65.2, 70.8, 71.7, 74.4, 95.3, 98.7, 104.5, 107.6, 111.2, 126.9, 127.5, 128.5, 129.0, 130.2, 142.3, 149.5, 158.3, 161.3, 170.1, 171.2, 175.7

III-27 (E)-1-[10,11-Dihydro-5H-dibenzo[a,d]cyclohepten-5-yl]-piperazin-1-yl]-ethenyl]-4,5-dimethoxy-phenoxy}-propan-2-ol The reaction was carried out following the same procedure described for example III-1 using 10,11-dihydro-5H-dibenzo[a,d]cyclohepten-5-yl-piperazine and epoxide IIIa-12.

Mp.: 130°–132.5° C. $^{13}$C-NMR [CDCl$_3$; δ (ppm)]: 31.8, 52.0, 56.1, 56.3, 58.2, 60.5, 65.6, 65.9, 72.6, 89.1, 99.4, 99.5, 109.9, 111.5, 117.0, 125.5, 127.7, 129.8, 130.9, 139.4, 139.7, 144.0, 151.1, 152.2, 161.7, 169.9

III-28 (E)-1-[10,11-Dihydro-5H-dibenzo[a,d]cyclohepten-5-yl]-piperazin-1-yl]-3-{2-[2-(3-methoxymethyl-isoxazol-5-yl)-ethenyl]-5-N,N-diethylamino]-phenoxy}-propan-2-ol The reaction was carried out following the same procedure described for example III-1 using 10,11-dihydro-5H-dibenzo[a,d]cyclohepten-5-yl-piperazine and epoxide IIIa-13.

$^{13}$C-NMR [DMSO; δ (ppm)] (citrate): 12.5, 30.9, 43.5, 43.7, 44.6, 50.0, 52.9, 57.8, 64.9, 65.3, 70.9, 71.7, 77.3, 95.3, 98.7, 104.5, 107.6, 111.2, 115.4, 127.7, 129.0, 130.2, 130.4, 130.6, 138.8, 149.5, 161.3, 170.1, 171.1, 175.8

III-29 (E)-1-[4-(Cyclohexyl-phenyl)-methyl-piperazin-1-yl]-3-{2-[2-(3-methoxymethyl-isoxazol-5-yl)-ethenyl]-4,5-dimethoxy-phenoxy}-propan-2-ol The reaction was carried out following the same procedure described for example III-1 using 4-(cyclohexyl-phenyl)-methyl-piperazine and epoxide IIIa-12.

$^{13}$C-NMR [DMSO; δ (ppm)] (citrate) : 25.4, 25.5, 26.3, 29.6, 30.4, 36.4, 43.6, 46.6, 53.0, 55.7, 56.0, 57.8, 59.5, 64.9, 71.6, 72.0, 73.4, 99.2, 100.0, 110.0, 111.0, 115.6, 126.8, 127.6, 129.0, 136.3, 143.3, 150.9, 151.6, 161.4, 169.3, 171.2, 176.0

III-30 ( E)-1-[4-(Cyclohexyl-phenyl)-methyl-piperazin-1-yl]-3-{2-[2-(3-methyl-isoxazol-5-yl)-ethenyl]-5-N,N-diethylamino-phenoxy}-propan-2-ol The reaction was carried out following the same procedure described for example III-1 using 4-(cyclohexyl-phenyl)-methyl-piperazine and epoxide IIIa-13.

Mp.: 56°–80° C.

Ill-31 (E)-1-[4-(2-Hydroxy-3-{2-[2-(3-methoxymethyl-isoxazol-5-yl)-ethenyl]-4,5-dimethoxy-phenoxy}-propyl)-piperazin-1-yl]-2,2-diphenyl-ethanone The reaction was carried out following the same procedure described for example III-1 using 2,2-diphenyl-acetyl-piperazine and epoxide IIIa-12.

Mp.: 55°–71° C.

III-32 (E)-1-[4-(2-Hydroxy-3-{2-[2-(3-methoxymethyl-isoxazol-5-yl)-ethenyl]-phenoxy}-propyl)-piperazin-1-yl]-2,2-diphenyl-ethanone The reaction was carried out following the same procedure described for example III-1 using 2,2-diphenyl-acetyl-piperazine and epoxide IIIa-1.

$^{13}$C-NMR [DMSO; δ (ppm)] (citrate): 41.1, 42.9, 44.9, 52.5, 52.8, 53.1, 57.8, 53.1, 57.8, 60.4, 64.7, 64.8, 65.9, 71.2, 72.1, 101.0, 112.7; 113.6, 120.7, 123.8, 126.5, 127.6, 128.1, 128.2, 128.8, 129.4, 130.5, 140.0, 156.6, 161.6, 168.8, 169.4, 171.2, 175.0

III-35 (E)-1-[4-(Diphenyl-methyl)-piperazin-1-yl]-3-{2-[2-(3-isopropyl-isoxazol-5-yl)-ethenyl]-phenoxy}-propan-2-ol The reaction was carried out according to example III-1 using 4-(diphenyl-methyl)piperazine and (E)-5-{2-[2-(2,3-epoxypropoxy)-phenyl]-ethenyl}-3-(isopropyl)-isoxazole.

Mp.: 145°–146° C. $^{13}$C-NMR [CDCl$_3$; δ (ppm)]: 21.8, 26.5, 52.0, 53.6, 60.7, 71.0, 76.2, 99.2, 112.5, 114.3, 121.2, 125.1, 126.9, 127.7, 127.9, 128.5, 129.7, 130.1, 142.7, 156.9, 168.7, 169.6

III-36 (E)-1-[4-(Diphenyl-methyl)-piperazin-1-yl]-3-{2-[2-(3-methyl-isoxazol-5l)-ethenyl]-phenoxy}-propan-2-ol The reaction was carried out following the same procedure described for example III-1 using 4-(diphenyl-methyl)-piperazine and (E)-5-{2-[2-(2,3-epoxypropoxy)-phenyl]-ethenyl}-3-(methyl)-isoxazole.

Mp.: 174°–175° C. (hydrochloride)

III-37 (E)-1-[4-(Diphenyl-methyl)-piperazin-1-yl]-3-{2-[2-(2-(4-methoxyphenyl)-1,3-oxazol-4-yl)-ethenyl]-phenoxy}-propan-2-ol The reaction was carried out following the same procedure described for example III-1 using 4-(diphenyl-methyl)-piperazine and epoxide IIIa-10.

$^{13}$C-NMR [CDCl$_3$; δ (ppm)]: 52.0, 53.7, 55.3, 60.8, 65.7, 71.1, 76.2, 112.6, 114.2, 117.6, 120.3, 121.2, 125.7, 126.5, 126.9, 127.2, 127.9, 128.3, 128.5, 128.7, 134.6, 140.9, 142.7, 156.4, 161.5, 161.8

III-38 (E)-1-[4-(10,11-Dihydro-5H-dibenzo[a,d]cyclohepten-5-yl)-piperazin-1-yl]-3-{2-[2-(2-(4-methoxyphenyl)-1,3-oxazol-4-yl)-ethenyl]-phenoxy}-propan-2-ol The reaction was carried out following the same procedure described for example III-1 using 10,11-dihydro-5H-dibenzo[a,d]cyclohepten-5-yl-piperazine and epoxide IIIa-10.

$^{13}$C-NMR [CDCl$_3$; δ (ppm)]: 31.7, 52.0, 53.8, 55.4, 60.7, 65.7, 71.1, 79.1, 112.6, 114.1, 117.7, 120.3, 121.2, 125.5, 125.7, 126.5, 127.3, 127.7, 128.3, 128.7, 130.8, 134.6, 139.3, 139.6, 140.9, 156.5, 161.5, 161.8

III-39 (E)-1-[4-(10,11-Dihydro-5H-dibenzo[a,d]cyclohepten-5-yl)-piperazin-1-yl]-3-{2-[2-(5-(4-methyl-phenyl)-1,3,4-oxadiazol-2-yl)-ethenyl]-phenoxy-}-propan-2-ol The reaction was carried out following the same procedure described for example III-I using 10,11-dihydro-5H-dibenzo[a,d]cyclohepten-5-yl-piperazine and epoxide IIIa-9.

$^{13}$C-NMR [CDCl$_3$; δ (ppm)]: 21.7, 31.7, 52.0, 53.7, 60.6, 65.4, 71.0, 79.1, 110.9, 112.6, 121.3, 124.2, 125.5, 126.9, 127.7, 128.5, 129.7, 130.7, 130.8, 131.0, 134.2, 139.2, 139.6, 142.1, 157.3, 164.0, 164.6 III-40 (E)-1-[4-(Diphenyl-methyl)-piperazin-1-yl]-3-{2-[2-(5-(4-methyl-phenyl)-1,3,4-oxadiazol-2-yl)-ethenyl]-phenoxy}-propan-2-ol The reaction was carried out following the same procedure described for example III-1 using 4-(diphenyl-methyl)-piperazine and epoxide IIIa-9.

$^{13}$C-NMR [CDCl$_3$; δ (ppm)]: 21.7, 52.0, 53.7, 60.8, 65.4, 70.9, 76.2, 110.9, 112.5, 121.3, 124.2, 126.9, 127.0, 127.9, 128.4, 128.5, 129.7, 131.0, 134.2, 142.2, 142.7, 157.2, 164.0, 164.6

III-42 (E)-1-[4-(Diphenyl-methyl-piperazin-1-yl]-3-{2-[2-(3,5-dimethyl-isoxazol-4-yl)-ethenyl]-phenoxy}-propan-2-ol The reaction was carded out following the same procedure described for example III-1 using 4-(diphenyl-methyl)-piperazine and (E)-4-{2-[2-(2,3-epoxypropoxy)-phenyl]-ethenyl}-3,5-dimethyl-isoxazole.

$^{13}$C-NMR [CDCl$_3$; δ (ppm)]: 11.7, 11.9, 52.0, 53.7, 60.8, 65.5, 70.8, 76.2, 112.4, 113.6, 117.0, 121.2, 125.0, 126.2, 126.7, 127.0, 127.9, 128.5, 128.8, 142.6, 155.9, 158.3, 165.5

III-43 (E)-1-[4-(10,11-Dihydro-5H-dibenzo[a,d]cyclohepten-5-yl)-piperazin-1-yl]-3-{2-[2-(3,5-dimethyl-isoxazol-4-yl)-ethenyl]-phenoxy}-propan-2-ol The reaction was carried out following the same procedure described for example III-1 using 10, 11-dihydro-5H-dibenzo[a,d]cyclohepten-5-yl-piperazine and (E)-4-{2-[2-(2,3-epoxypropoxy)-phenyl]-ethenyl}-3,5-dimethyl-isoxazole.

$^{13}$C-NMR [CDCl$_3$; δ (ppm)]: 11.7, 11.9, 31.7, 52.0, 53.7, 60.7, 65.5, 70.8, 79.1, 112.4, 113.6, 116.9, 121.2, 125.0, 125.5, 126.1, 126.6, 127.8, 128.8, 130.8, 139.1, 139.7, 155.9, 158.3, 165.4

III-44 (E)-1-[4-{Bis(4-fluorophenyl)-methyl}-piperazin-1-yl]-3-{2-[2-(3,5-dimethyl-isoxazol-4-yl)-ethenyl]-phenoxy}-propan-2-ol The reaction was carried out following the same procedure described for example III-1 using bis(4-fluorophenyl)-methyl-piperazine and (E)-5-{2-[2-(2,3-epoxypropoxy)-phenyl]-ethenyl}-3,5-dimethyl-isoxazole.

$^{13}$C-NMR [CDCl$_3$; δ (ppm)]: 11.7, 11.9, 51.8, 53.6, 60.8, 65.4, 70.9, 74.5, 112.4, 113.6, 115.5 (d, J=21 Hz), 116.9, 121.3, 125.0, 126.2, 126.7, 128.8, 129.2 (d, J=8 Hz), 138.1, 155.9, 158.3, 161.9 (d, J=245 Hz), 165.5

III-45 (E)-1-[4-(Diphenyl-methyl)-piperazin-1-yl]-3-{2-[2-(2-methoxymethyl-1,3-thiazol-4-yl)-ethenyl]-phenoxy}-propan-2-ol The reaction was carried out following the same procedure described for example III-1 using 4-(diphenyl-methyl)-piperazine and epoxide IIIa-8.

$^{13}$C-NMR [CDCl$_3$, δ (ppm)]: 52.0, 53.7, 59.0, 60.8, 65.7, 71.1, 71.7, 76.3, 112.6, 115.0, 121.2, 122.3, 126.4, 126.6, 127.0, 127.4, 128.5, 128.8, 142.7, 154.8, 156.5, 168.6 III-46 (E)-1-[4-(10,11-Dihydro-5H-dibenzo[a,d]cyclohepten-5-yl)-piperazin-1-yl]-3-{2-[2-(2-methoxymethyl-1,3-thiazol-4-yl)-ethenyl]-phenoxy}-propan-2-ol The reaction was carried out following the same procedure described for example III-1 using 10,11-dihydro-5H-dibenzo[a,d]cyclohepten-5-yl-piperazine and epoxide IIIa-8.

$^{13}$C-NMR [CDCl$_3$, δ (ppm)]: 31.7, 52.0, 53.7, 59.0, 60.7, 65.7, 71.1, 71.6, 79.1, 112.6, 115.0, 121.2, 122.3, 125.5, 126.4, 126.5, 127.3, 127.7, 128.8, 130.7, 139.2, 139.6, 154.8, 156.5, 168.6

III-47 (E)-1-[Bis-(4-fluorophenyl-methyl)-piperazin-1-yl]-3-{2-[2-(2-methoxy-methyl-1,3-thiazol-4-yl)-ethenyl]-phenoxy}-propan-2-ol The reaction was carried out following the same procedure described for example III-1 using bis(4-fluorophenyl-methyl)-piperazine and epoxide IIIa-8.

$^{13}$C-NMR [CDCl$_3$; δ (ppm)]: 51.9, 53.7, 59.0, 60.8, 65.8, 71.1, 71.7, 74.5, 112.6, 115.0, 115.4 (d, J=21 Hz), 121.2, 122.3, 126.4, 126.6, 127.4, 128.8, 129.2 (d, J=8 Hz), 138.2, 154.8, 156.5, 161.8 (d, J=246 Hz), 168.6

III-48 (E)-1-[4-(Diphenyl-methyl)-piperazin-1-yl]-3-{2-[2-(thiophen-2-yl)-ethenyl]-phenoxy}-propan-2-ol The reaction was carried out following the same procedure described for example III-1 using 4-(diphenyl-methyl)-piperazine and (E)-2-{2-[2-(2,3-epoxypropoxy)-phenyl]-ethenyl}-thiophen.

Mp: 131°–132° C. (hydrochloride)

III-49 (E)-1-[4-(Diphenyl-methyl)-piperazin-1-yl]-3-{2-[2-(thiophen-3-yl)-ethenyl]phenoxy}-propan-2-ol The reaction was carried out following the same procedure described for example III-1 using 4-(diphenyl-methyl)-piperazine and (E)-3-{2-[2-(2,3-epoxypropoxy)-phenyl]-ethenyl }-thiophen.

Mp: 188°–189° C. (hydrochloride)

III-50 (E)--1-[4-Diphenyl-methyl)-piperazin-1-yl]-3-{2-(5-methyl-thia-3,4-diazol-2-yl)-ethenyl]-phenoxy}-propan-2-ol The reaction was carried out following the same procedure described for example III-1 using 4-(diphenyl-methyl)-piperazine and (E)-2-{2-[2-(2,3-epoxypropoxy)-phenyl]-ethenyl}-5-methyl-thia-3,4-diazol.

Mp: 223°–234° C. (hydrochloride)

III-51 (E)-1-[2-(3,4-Dimethoxyphenyl)-ethyl]-piperazin-1-yl]-3-{2-[2-(3-methoxymethyl-isoxazol-5-yl)-ethenyl]-phenoxy}-propan-2-ol The reaction was carried out following the same procedure described for example III-1 using 1-[2-(3,4-dimethoxyphenyl)-ethyl]-piperazine and epoxide IIIa-1.

Mp.: 197°–199° C. $^{13}$C-NMR [DMSO; δ (ppm)] (oxalate): 29.9, 50.5, 55.4, 57.1, 57.8, 59.4, 64.9, 65.8, 71.1, 101.1, 112.0, 112.5, 112.7, 113.7, 120.5, 120.9, 123.9, 127.6, 129.4, 130.2, 130.5, 147.5, 148.7, 156.6, 161.6, 162.6, 168.9.

III-52 (E)-1-[10,11-Dihydro-5H-dibenzo[a,d]cyclohepten-5-yl]-piperazin-1-yl]-3-{2-[2-(3-methoxymethyl-isoxazol-5-yl)-ethenyl]-4-nitro-phenoxy}propan-2-ol The reaction was carded out according to example III-1 using 10,11-dihydro-5H-dibenzo[a,d]cyclohepten-5-yl-piperazine and epoxide IIIa-16.

$^{13}$C-NMR [CDCl$_3$; δ (ppm)]: 31.7, 51.9, 53.5, 58.6, 60.1, 65.1, 65.8, 71.7, 79.1, 101.7, 112.1, 116.3, 123.0, 125.5, 125.6, 127.7, 127.8, 130.8, 130.8, 139.1, 139.7, 141.8, 161.2, 161.8, 168.3

III-53 (E)-1-[4-(Diphenyl-methyl)-piperazin-1-yl]-piperazin-1-yl]-3-{2-[2-(3-methoxymethyl-isoxazol-5-yl)-ethenyl]-4-nitro-phenoxy}-propan-2-ol The reaction was carried out according to example III-1 using 4-(diphenyl-methyl)piperazine and epoxide IIIa-16.

$^{13}$C-NMR [CDCl$_3$; δ (ppm)]: 51.9, 53.6, 58.6, 60.3, 65.2, 65.8, 71.7, 76.2, 101.7, 112.1, 125.0, 125.6, 127.0, 127.7, 127.9, 128.5, 141.7, 161.2, 161.9, 168.3.

III-54 (E)-1-[4-(Diphenyl-methyl)-piperazin-1-yl]-3-{2-[2-(5-methoxymethyl-3-isoxazolyl)-ethenyl]-phenoxy}-propan-2-ol The reaction was carded out according to example III-1 using 4-(diphenyl-methyl)piperazine and epoxide IIIa-7.

$^{13}$C-NMR [CDCl$_3$; δ (ppm)]: 51.9, 53.6, 58.8, 60.6, 65.3, 65.5, 71.2, 76.2, 99.9, 112.6, 116.5, 121.3, 125.2, 127.0, 127.4, 127.9, 128.5, 130.0, 131.1, 142.6, 156.6, 162.3, 168.9

III-55 (E)-1-[4-(10,11-Dihydro-5H-dibenzo[a,d]cyclohepten-5-yl)-piperazin-1-yl]piperazin-1-yl]-3-{2-[2-(5-methoxymethyl-isoxazol-3-yl)-ethenyl]-phenoxy}-propan-2-ol The reaction was carded out according to example III-1 using 10,11-dihydro-5H-dibenzo[a,d]cyclohepten-5-yl-piperazine and epoxide IIIa-7.

$^{13}$C-NMR [CDCl$_3$; δ (ppm)]: 31.7, 52.0, 53.7, 58.8, 60.6, 65.4, 65.5, 71.2, 79.0, 99.9, 112.7, 116.5, 121.3, 125.2, 125.5, 127.4, 127.7, 130.0, 130.7, 130.8, 131.1, 139.2, 139.6, 156.6, 162.3, 168.9

III-56 (E)-1-[Bis(4-methoxyphenyl)-methyl-piperazin-1-yl]-3-{2-[2-(2-methoxymethyl-1,3-thiazol-4-yl)-ethenyl]-phenoxy}-propan-2-ol The reaction was carded out following the same procedure described for example III-1 using bis(4-methoxyphenyl)-methyl-piperazine and epoxide IIIa-8.

$^{13}$C-NMR [CDCl$_3$; δ (ppm)] (fumarate): 50.0, 52.9, 54.9, 58.3, 60.2, 65.3, 70.7, 71.0, 73.2, 112.6, 113.8, 116.5, 120.8, 122.1, 125.3, 125.3, 126.6, 128.4, 128.9, 134.4, 134.6, 153.8, 156.0, 158.0, 166.7, 168.4

III-57 (E)-1-[4-(Cyclohexyl-phenyl)-methyl-piperazin-1-yl]-3-{2-[2-(pyridin-3-yl)-ethenyl]-phenoxy}-propan-2-ol The reaction was carried out according to example III-58 using precursor IIIh-1, 3-pyridine aldehyde and potassium tert.butylate as base.

$^{13}$C-NMR [DMSO; δ (ppm)] (citrate) : 25.4, 25.5, 26.2, 29.5, 30.4, 36.3, 43.5, 52.7, 59.2, 64.5, 70.9, 71.7, 73.3, 112.5, 112.6, 121.0, 123.2, 123.7, 125.0, 125.3, 126.3, 126.6, 126.9, 127.7, 128.0, 129.0, 129.3, 132.7, 133.1, 135.2, 136.1, 148.1, 148.2, 149.3, 155.7, 171.3, 175.8

III-58 (E)-1-[4-(Cyclohexyl-phenyl)-methyl-piperazin-1-yl]-3-{2-[2-(pyridin-2-yl)-ethenyl]-phenoxy}-propan-2-ol A suspension of 12.5 mmol sodium hydride in 20 ml absolute dimethylformamide was prepared under inert gas. A solution of 5 mmol of diethyl 2-{3-[4-(cyclohexyl-phenylmethyl]-piperazin-1-yl]-2-hydroxy-propoxy}-benzyl phosphonate (precursor IIIh-1) in 30 ml absolute dimethylformamide was added dropwise at room temperature. The reaction mixture was stirred at room temperature for 2 hours. Then a solution of 7 mmol 2-pyridine aldehyde in 10 ml absolute dimethylformamide was added dropwise. The reaction mixture was stirred at room temperature for another 12 hours. For work-up the reaction mixture was poured into 500 ml of water and extracted with ether. The ether phase was washed once with water, dried over sodium sulfate and filtered. The ether was removed under reduced pressure. The desired product was isolated as an oil (1.6 g). The citrate of the product was prepared for analytical purposes by addition of 2 aliquot of citric acid dissolved in ether.

$^{13}$C-NMR [DMSO; δ (ppm)] (citrate): 25.4, 25.5, 26.2, 29.6, 30.4, 36.3, 43.4, 52.8, 64.5, 70.7, 71.7, 73.3, 112.7, .121.0, 122.1, 122.3, 125.1, 126.7, 126.9, 127.0, 127.7, 128.5, 129.0, 129.5, 136.1, 136.7, 149.4, 155.3, 156.1, 171.2, 175.7

III-106 (E)-1-[4-(Cyclohexyl-phenyl)-methyl-piperazin-1-yl]-3-{2-[2-(pyridin-4yl)-ethenyl]-phenoxy}-propan-2-ol Prepared according to the procedure given for compound III-58 and 4-pyridine aldehyde.

$^{13}$C-NMR [DMSO; δ (ppm)] (citrate) : 25.4, 25.5, 26.2, 29.6, 30.4, 36.3, 43.4, 52.8, 59.3, 64.6, 64.8, 70.5, 70.8, 71.8, 73.3, 112.5, 112.7, 120.4, 120.8, 121.0, 123.0, 124.7, 126.3, 126.9, 127.0, 127.3, 127.7, 129.0, 129.3, 129.5, 129.9, 136.2, 144.3, 144.7, 149.5, 149.9, 155.9, 156.0, 171.2, 175.7

III-107 (E)-1-[4-(Cyclohexyl-phenyl)-methyl-piperazin-1-yl]-3-{2-[2-(N-methyl-pyrrol-2-yl)-ethenyl]-phenoxy}-propan-2-ol The reaction was carried out according to example III-58 using precursor IIIh-1 and 2-(N-methyl)-pyrrol aldehyde.

Mp: 148°–156° C.

III-108 (E)-1-[4-(Diphenyl-methyl)-piperazin-1-yl]-3-{2-[2-(N-methyl-pyrrol-2-yl)-ethenyl]-phenoxy}-propan-2-ol The reaction was carried out according to example III-58 using diethyl 2-{3-[4-(diphenyl-methyl]-piperazin-1-yl]-2-hydroxy-propoxy}-benzyl phosphonate and 2-(N-methyl)-pyrrol aldehyde.

$^{13}$C-NMR [DMSO; δ (ppm)] (citrate): 33.6, 43.4, 52.6, 59.6, 64.8, 65.0, 70.9, 71.7, 74.3, 106.1, 107.7, 112.4, 118.0, 119.4, 120.8, 123.6, 125.9, 126.4, 126.9, 127.4, 127.8, 128.5, 131.8, 142.2, 151.8, 155.2, 171.2, 175.6

III-109 (E)-1-[4-(Diphenyl-methyl)-piperazin-1-yl]-3-{2-[2-(pyridin-4-yl)-ethenyl]-phenoxy}-propan-2-ol The reaction was carried out according to example III-58 using diethyl 2-{3-[4-(diphenyl-methyl]-piperazin-1-yl]-2-hydroxy-propoxy}-benzyl phosphonate and 4-pyridine aldehyde.

$^{13}$C-NMR [DMSO; δ (ppm)] (citrate) : 43.3, 49.2, 52.5, 59.2, 63.0, 64.3, 64.6, 70.9, 71.9, 74.2, 112.5, 112.7, 120.4, 120.7, 121.0, 123.0, 124.7, 126.3, 127.0, 127.3, 127.4, 127.6, 128.5, 129.3, 129.6, 130.0, 142.1, 144.3, 144.7, 149.5, 149.8, 155.9, 156.1, 171.2, 175.5

III-110 1-[4-(Diphenyl-methyl)-piperazin-1-yl]-3-{2-[2-(pyridin-3-yl)-ethenyl]-phenoxy}-propan-2-ol The reaction was carried out according to example III-58 using diethyl 2-{3-[4-(diphenyl-methyl]-piperazin-1-yl]-2-hydroxy-propoxy}-benzyl phosphonate and 3-pyridine aldehyde.

$^{13}$C-NMR [DMSO; δ (ppm)] (citrate): 43.4, 49.6, 52.6, 64.9, 71.1, 71.7, 74.3, 112.6, 120.9, 123.6, 125.1, 125.3, 126.3, 126.6, 126.9, 127.4, 128.5, 129.3, 132.6, 133.1, 142.2, 148.1, 148.2, 155.8, 171.2, 175.6

III-111 1-[4-(Diphenyl-methyl)-piperazin-1-yl]-3-{2-[2-(pyridin-2-yl)-ethenyl]-phenoxy}-propan-2-ol The reaction was carried out according to example III-58 using diethyl 2-{3-[4-(diphenyl-methyl]-piperazin-1-yl]-2-hydroxy-propoxy}-benzyl phosphonate and 2-pyridine aldehyde.

$^{13}$C-NMR [DMSO; δ(ppm)] (citrate): 43.4, 49.6, 52.7, 59.7, 64.9, 71.0, 71.8, 74.3, 112.3, 112.7, 120.2, 120.9, 121.9, 122.1, 122.8, 123.1, 125.1, 125.2, 126.8, 126.9, 127.0, 127.4, 128.4, 128.5, 129.2, 129.5, 130.1, 135.8, 136.7, 142.2, 149.1, 149.3, 155.3, 155.6, 155.9, 156.2, 171.2, 175.6

III-112 (E)-[4-(2-Hydroxy-3-{2-[2-(3-methoxymethyl-isoxazol-5-yl)-ethenyl]-phenoxy}propyl)-piperazin-1-yl]-(9H-xanthen-9-yl)-methanone The reaction was carded out according to example III-1 using precursor IIIa-1 and piperazin-1-yl-(9H-xanthen-9-yl)-methanone.

Mp: 120°–123° C.

III-113 (E)-1-[4-(2-Hydroxy-3-{2-[2-(3-methoxymethyl-isoxazol-5-yl)-ethenyl]-phenoxy}-propyl)-piperazin-1-yl]-cyclohexyl-phenyl-ethanone The reaction was carded out according to example III-1 using precursor IIIa-1 and piperazin-1-yl-(9H-xanthen-9-yl)-methanone.

$^{13}$C-NMR [DMSO; δ (ppm)] (citrate) : 25.5, 29.8, 31.6, 40.6, 40.8, 42.9, 44.5, 52.4, 52.8, 53.0, 53.4, 53.5, 57.8, 60.2, 60.4, 64.7, 64.8, 71.2, 72.1, 101.0, 112.1, 112.6, 113.6, 120.8, 123.8, 126.5, 126.5, 127.6, 128.2, 129.4, 130.5, 138.8, 156.6, 161.0, 168.8, 170.6, 1 71.2, 175.0.

III-114 (E)-1-[10,11,Dihydro-5H-dibenzo[a,d]cyclohepten-5-yl]-piperazin-1-yl]-3-{2-[2-(3-methoxymethyl-isoxazol-5-yl)-ethenyl]-6-fluoro-phenoxy}-propan-2-ol The reaction was carried out according to example III-1 using 10,11-dihydro-5H-dibenzo[a,d]cyclohepten-5-yl-piperazine and epoxide IIIa-14.

Mp: 140°–142° C.

III-115 (E)-1-[4-(Diphenyl-methyl)-piperazin-1-yl]-3-{2-[2-(3-methoxymethyl-isoxazol-5-yl)-ethenyl]-6-fluoro-phenoxy}-propan-2-ol The reaction was carried out according to example III-1 using 4-(diphenyl-methyl)piperazine and epoxide IIIa-14.

$^{13}$C-NMR [DMSO; δ (ppm)] (citrate) : 43.4, 49.9, 52.7, 57.8, 59.3, 64.8, 65.7, 71.7, 74.4, 76.7, 101.7, 115.3, 117.1 (d, J=19.2 Hz), 122.3, 124.2 (d, J=11.5 Hz), 126.9, 127.4, 127.8, 128.5, 130.3, 142.3, 144.3 (d, J=11.5 Hz), 153.9 and 156.4 (d, J=245.1 Hz), 161.6, 168.3, 171.2, 175.7.

III-116 (E)-1-[4-(10,11-Dihydro-5H-dibenzo[a,d]cyclohepten-5-yl)-piperazin-yl]-3-{2-[2-(4-dimethyl-1,3-oxazolin-2-yl)-ethenyl]-phenoxy}-propan-2-ol The reaction was carried out according to example III-1 using 10,11-dihydro-5H-dibenzo[a,d]cyclohepten-5-yl-piperazine and epoxide IIIa-11.

$^{13}$C-NMR [CDCl$_3$; δ (ppm)] (citrate): 27.8, 27.9, 31.9, 44.7, 48.5, 54.8, 61.2, 64.2, 66.3, 70.1, 72.5, 77.9, 79.2, 112.1, 115.9, 121.4, 123.5, 128.3, 130.9, 131.2, 131.3, 132.4, 137.5, 139.3, 139.6, 157.4, 164.2, 173.4, 180.0

III-117 (E)-1-[4-(Diphenyl-methyl)-piperazin-1-yl]-3-{2-[2-(4-dimethyl)-1,3-oxazolin-2-yl)-ethenyl]-phenoxy}-propan-2-ol The reaction was carried out according to example III-I using 4-(diphenyl-methyl)piperazine and epoxide IIIa-11.

$^{13}$C-NMR [CDCl$_3$; δ (ppm)]: 28.4, 52.0, 53.0, 60.6, 65.6, 67.2, 71.1, 76.3, 78.7, 112.5, 116.2, 121.2, 124.7, 127.0, 127.9, 128.5, 130.5, 134.7, 142.7, 156.9, 162.3

III-118 (E)-1-[4-(Diphenyl-methyliden)-piperidin-1-yl]-3-{2-[2-(3-methoxymethyl-isoxazol-5-yl)-ethenyl]-phenoxy}-propan-2-ol 1 g of (E)-5-{2-[3-(2,3-epoxypropoxy)-phenyl]-ethenyl}-3-(methoxymethyl)-isoxazole (precursor IIIa-1), 1 g of 4-(diphenyl-methyliden)-piperidine hydrochloride and 0.4 ml of N-methylmorpholin were refluxed in 10 ml ethanol. After the reaction was completed the solvent was evaporated and the crude residue purified by chromatography on silica gel. The obtained oily residue was treated with diethylether for crystallisation.

Mp.: 132°–133° C. $^{13}$C-NMR [DMSO; δ (ppm)]: 31.2, 38.8, 39.0, 39.2, 39.9, 40.2, 55.4, 57.8, 60.9, 64.8, 66.5, 71.6, 100.9, 112.7, 113.6, 120.7, 123.8, 126.3, 127.7, 128.1, 129.3, 129.6, 130.5, 135.0, 135.2, 142.0, 156.8, 161.5, 168.9

III-119 (E)-1-[4-(Diphenyl-methyliden)-piperidin-1-yl]-3-{2-[4-(3-methoxymethy-isoxazol-5-yl)-ethenyl]-phenoxy}-propan-2-ol The reaction was carried out following the same procedure described for example III-118 using epoxide IIIa-3.

Mp.: 120°–122° C. $^{13}$C-NMR [CDCl$_3$; δ (ppm)]: 31.7, 55.6, 58.4, 60.4, 65.7, 65.9, 70.6, 99.9, 111.1, 115.0, 126.5, 128.1, 128.6, 129.8, 134.6, 134.7, 136.6, 142.4, 159.8, 161.8, 169.2

III-120 (E)-1-[4-(Diphenyl-methyliden)-piperidin-1-yl]-3-{2-[2-(3-methyl-isoxazol-5yl)-ethenyl]-phenoxy}-propan-2-ol The reaction was carried out following the same procedure described for example III-118 using (E)-5-{2-[2-(2,3-epoxypropoxy)-phenyl]-ethenyl}-3-(methyl)-isoxazole.

Mp.: 155°–157° C. $^{13}$C-NMR [CDCl$_3$; δ (ppm)]: 11.5, 18.5, 31.8, 55.5, 60.7, 65.6, 71.1, 101.9, 112.5, 114.1, 121.2, 124.1, 126.4, 127.7, 128.0, 129.8, 130.1, 134.8, 136.5, 142.4, 156.9, 160.0, 168.9

III-121 (E)-1-[4-(Diphenyl-methyliden)-piperidin-1-yl]-3-{2-[2-(3-carbethoxy-isoxazol-5yl)-ethenyl]-phenoxy}-propan-2-ol The reaction was carried out following the same procedure described for example III-118 using (E)-3-(carbethoxy)-5-{2-[2-(2,3-epoxypropoxy)-phenyl]-ethenyl}-isoxazole.

Mp.: 124°–125° C. $^{13}$C-NMR [CDCl$_3$; δ (ppm)]: 14.2, 31.8, 55.5, 60.6, 62.1, 65.5, 71.0, 101.1, 112.6, 113.3, 121.3, 124.5, 126.4, 128.1, 129.8, 130.7, 131.6, 134.7, 136.5, 142.4, 156.7, 157.1, 160.1, 171.1

III-122 (E)-1-[4-(Diphenyl-methyliden)-piperidin-1-yl]-3-{2-[3-(3-methoxymethyl-isoxazol-5-yl)-ethenyl]-phenoxy}-propan-2-ol The reaction was carried out following the same procedure described for example III-118 using epoxide IIIa-2.

$^{13}$C-NMR [CDCl$_3$; δ (ppm)] (citrate): 28.2, 44.3, 55.0, 58.5, 60.1, 64.5, 65.8, 69.8, 73.2, 101.1, 112.9, 113.6, 115.5, 120.6, 127.2, 128.3, 128.4, 129.3, 130.0, 134.6, 137.0, 139.8, 141.0, 158.6, 161.8, 168.7, 174.0, 178.9

III-123 (E)-1-[4-(Diphenyl-methyliden)-piperidin-1-yl]-3-{2-[2-(3-isopropyl-isoxazol-5-yl)-ethenyl]-phenoxy}-propan-2-ol The reaction was carried out following the same procedure described for example III-118 using (E)-5-{2-[2-(2,3-epoxypropoxy)-phenyl]-ethenyl}-3-(isopropyl)-isoxazole.

Mp.: 156°–157° C.

$^{13}$C-NMR [CDCl$_3$; δ (ppm)]: 21.8, 26.5, 31.8, 55.6, 60.7, 65.2, 71.1, 99.3, 112.6, 114.3, 121.2, 125.1, 126.4, 127.7, 128.1, 129.7, 129.8, 130.1, 134.8, 136.5, 142.1, 156.9, 168.8, 169.7

III-124 (E)-1-[4-(Diphenyl-methyliden)-piperidin-1-yl]-3-{2-[2-(3-phenyl-isoxazol-5-yl)-ethenyl]-phenoxy}-propan-2-ol The reaction was carried out following the same procedure described for example III-118 using (E)-5-{2-[3-(2,3-epoxypropoxy)-phenyl]-ethenyl}-3-(phenyl)-isoxazole.
Mp.: 155°–157° C.
$^{13}$C-NMR [CDCl$_3$; δ (ppm)]: 31.6, 55.6, 60.8, 66.3, 71.5, 99.1, 112.6, 113.7, 121.0, 124.5, 126.4, 126.6, 127.8, 127.9, 128.8, 129.1, 129.6, 129.9, 130.3, 135.1, 135.9, 142.3, 157.0, 162.5, 169.7

III-125 (Z)-1-[4-(Diphenyl-methyliden)-piperidin-1-yl]-3-{2-[2-(3-methoxymethyl-isoxazol-5-yl)-ethenyl]-phenoxy}-propan-2-ol The reaction was carried out following the same procedure described for example III-118 using the epoxy compound IIIa-15.
$^{13}$C-NMR [CDCl$_3$; δ (ppm)] (citrate): 31.8, 55.5, 60.5, 65.6, 65.8, 101.6, 112.1, 115.5, 120.8, 125.2, 126.4, 128.0, 129.8, 130.1, 131.9, 134.8, 136.4, 142.4, 156.2, 161.2, 168.3

III-127 (E)-1-[4-(Diphenyl-methyliden)-piperidin-1-yl]-3-{2-[2-(3-methoxymethyl-isoxazol-5-yl)-ethenyl]-5-N,N-diethyl-amino]-phenoxy}-propan-2-ol The reaction was carried out following the same procedure described for example III-118 using epoxide IIIa-13.
$^{13}$C-NMR [DMSO; δ (ppm)] (citrate): 12.4, 29.1, 43.6, 43.7, 54.0, 57.4, 59.3, 64.9, 70.6, 71.6, 95.2, 98.7, 104.6, 107.6, 111.1, 126.6, 128.2, 129.0, 129.2, 130.1, 136.6, 141.4, 149.5, 158.2, 161.3, 170.0, 171.2, 175.9

III-128 (E)-1-[4-(Diphenyl-methyliden)-piperidin-1-yl]-3-{2-[2-(3-methoxymethyl-isoxazol-5-yl)-ethenyl]-4,5-dimethoxy-phenoxy}-propan-2-ol The reaction was carried out following the same procedure described for example III-118 using epoxide IIIa-12.
Mp.: 149°–151° C.
$^{13}$C-NMR [CDCl$_3$; δ (ppm)]: 31.7, 55.5, 56.1, 56.5, 58.5, 60.6, 65.7, 65.9, 72.7, 99.3, 99.6, 109.9, 111.5, 117.0, 126.4, 128.1, 128.2, 129.5, 128.8, 134.6, 136.6, 142.4, 144.0, 151.1, 152.2, 161.7, 169.9

III-130 (E)-1-[4-(Diphenyl-methyliden)-piperidin-1-yl]-3-{2-[2-(3-methoxymethyl-isoxazol-5-yl)-ethenyl]-4-nitro-phenoxy}-propan-2-ol The reaction was carried out following the same procedure described for example III-118 using epoxide IIIa-16.
Mp.: 142°–144° C. $^{13}$C-NMR [CDCl$_3$, δ (ppm)]: 31.7, 55.5, 58.6, 60.2, 65.4, 71.8, 101.8, 112.1, 116.3, 123.0, 125.6, 126.5, 127.7, 128.1, 129.8, 134.5, 136.7, 141.7, 142.3, 161.3, 161.9, 168.3.

III-131 (E)-1-[4-(Diphenyl-methyliden)-piperidin-1-yl]-3-{2-[2-(3-methoxymethyl-isoxazol-5-yl)-ethenyl]-6-fluoro-phenoxy}-propan-2-ol The reaction was carried out following the same procedure described for example III-118 using epoxide IIIa-14.
Mp.: 102°–103° C.

III-132 (E)-3-{2-[2-(4-Dimethyl-1,3-oxazolin-2-yl)-1-[4-diphenylmethylidene-piperidin-1-yl]-ethenyl]-phenoxy}-propan-2-ol The reaction was carried out following the same procedure described for example III-118 using epoxide IIIa-11.
$^{13}$C-NMR [CDCl$_3$; δ (ppm)] (citrate): 27.8, 27.9, 28.4, 44.8, 55.9, 61.2, 64.4, 66.4, 70.2, 72.8, 79.1, 112.2, 115.9, 121.4, 123.6, 127.2, 128.4, 128.6, 129.4, 131.2, 131.6, 138.6, 139.6, 141.0, 157.2, 163.9, 173.9, 180.0

III-133 (E)-1-[10,11-Dihydro-5H-dibenzo[a,d]cyclohepten-5-yl]-piperazin-1-yl]-3-{2-[2-(3-methoxymethyl-isoxazol-5-yl)-1-methyl-ethenyl]-6-fluorophenoxy}propan-2-ol The reaction was carried according to example III-1 using 10,11-dihydro-5H-dibenzo[a,d]cyclohepten-5-yl-piperazine and epoxide IIIa-17.
$^{13}$C-NMR [DMSO; δ (ppm)] (citrate): 20.3, 30.9, 43.3, 49.6, 52.6, 57.8, 64.8, 64.9, 70.8, 71.7, 77.1, 102.5, 112.6, 114.4, 120.7, 125.5, 127.7, 128.8, 129.4, 130.4, 130.6, 132.4, 138.6, 138.9, 143.6, 151.7, 155.4, 161.1, 168.1, 171.2, 175.7.

III-134 (Z)-1-[10,11-Dihydro-5H-dibenzo[a,d]cyclohepten-5-yl]-piperazin-1-yl]-3-{2-[2-(3-methoxymethyl-isoxazol-5-yl)-1-methyl-ethenyl]-6-fluorophenoxy}-propan-2-ol The reaction was carried according to example III-1 using 10,11-dihydro-5H-dibenzo[a,d]cyclohepten-5-yl-piperazine and epoxide IIIa-17.
$^{13}$C-NMR [CDCl$_3$; δ (ppm)]: 26.2, 31.8, 51.9, 53.6, 58.2, 60.4, 65.4, 65.7, 65.9, 70.7, 79.1, 101.8, 112.7, 114.0, 121.5, 125.5, 127.7, 128.7, 129.1, 129.4, 130.1, 130.7, 139.2, 139.7, 144.2, 154.8, 160.8, 168.9.

III-135 (E)-1-[4-(Diphenyl-methyl)-piperazin-1-yl]-3-{2-[2-(3-methoxymethyl-isoxazol-5-yl)-1-methyl-ethenyl]-phenoxy}-propan-2-ol The reaction was carried according to example III-1 using 4-(diphenyl-methyl)-piperazine and epoxide IIIa-17. $^{13}$C-NMR [DMSO; δ (ppm)] (citrate): 20.3, 43.4, 49.8, 52.7, 57.8, 59.7, 64.8, 64.9, 70.8, 71.7, 74.4, 102.5, 112.6, 114.4, 120.7, 126.9, 127.4, 128.5, 128.8, 129.4, 132.4, 142.3, 143.7, 155..4, 161.2, 168.1, 171.2, 175.7.

III-137 (E)-1-[4-(Diphenyl-methyliden)-piperidin-1-yl]-3-{2-[2-(3-methoxymethyl-isoxazol-5-yl)-1-methyl-ethenyl]-phenoxy}-propan-2-ol The reaction was carried according to example III-118 using 4-(diphenyl-methyliden)-piperidin and epoxide IIIa-17.
$^{13}$C-NMR [DMSO; δ (ppm)] (citrate): 20.3, 29.4, 43.6, 54.2, 57.8, 59.6, 64.8, 65.1, 70.9, 71.7, 102.6, 112.7, 114.5, 120.8, 126.6, 128.2, 128.9, 129.2, 129.5, 132.6, 136.4, 141.6, 143.7, 155.5, 161.2, 168.2, 171.2, 175.9

III-139 (E)-1-[exo-6,7-Diphenyl-3-azabicyclo[3.2.0]hept-3-yl]-3-{2-[2-(3-methoxymethyl-isoxazol-5-yl)-ethenyl]-phenoxy}-propan-2-ol The reaction was carried according to example III-1 using exo-6,7-diphenyl-3-azabicyclo[3.2.0]heptane and epoxide IIIa-1.
$^{13}$C-NMR [DMSO; δ (ppm)] (citrate; mixture of E- and Z-Isomers 7:3): 43.5, 46.2, 46.3, 57.4, 57.6, 57.8, 59.8, 60.0, 60.1, 64.7, 64.8, 66.4, 66.6, 70.8, 71.2, 71.8, 101.1, 102.4, 112.3, 112.9, 113.7, 114.6, 120.3, 120.9, 124.0, 124.6, 125.3, 126.4. 127.5, 127.6, 127.9, 128.3, 129.4, 130.2, 130.5, 131.8, 140.6, 140.7, 156.0, 161.0, 161.6, 167.5, 168.8, 171.3, 175.9

III-140 (E)-1-[exo-6-(4-Fluor-phenyl)-3-azabicyclo[3.2.0]hept-3-yl]-3-{2-[2-(3-methoxy-methyl-isoxazol-5-yl)-ethenyl]-phenoxy}-propan-2-ol The reaction was carried according to example III-1 using exo-6-(4-fluor-phenyl)-3-azabicyclo[3.2.0]heptane and epoxide IIIa-1.
$^{13}$C-NMR [CDCl$_3$; δ (ppm)] (mixture of E- and lsomers 7:3): 34.1, 34.2, 37.0, 41.9, 42.2, 45.7, 46.2, 46.3, 57.6, 57.7, 57.8, 57.9, 58.4, 58.5, 59.4, 59.5, 61.3, 61.4, 61.5, 65.8, 65.9, 67.3, 70.9, 71.1, 100.2, 101.6, 112.2, 112.6, 13.9, 115.0, 115.2, 115.5, 120.8, 121.2, 124.9, 125.2, 127.7, 128., 129.8, 130.1, 130.3, 130.4, 132.0, 142.4, 156.3, 157.0, 160.0, 161.2, 161.7, 162.4, 168.3, 169.6

III-141 (E)-1-[exo-6-(4-Fluor-phenyl)-3-azabicyclo[3.2.0]hept-3-yl]-3-{4-[2-(quinolin-2-yl)-ethyl]-phenoxy}-propan-2-ol The reaction was carried according to example III-1 using exo-6-(4-fluor-phenyl)-3-azabicyclo[3.2.0]heptane and epoxide IIIa-3.

Mp.: 91°–104° C.

III-143 (E)-1-[4-Diphenyl-methyl)-piperazin-1-yl]-3-{2-[2-(3-trifluoromethyl-isoxazol-5-yl)-ethenyl]-phenoxy}-propan-2-ol The reaction was carried according to example III-1 using 4-(diphenyl-methyl)piperazine and epoxide IIIa-4.

$^{13}$C-NMR [CDCl$_3$; δ (ppm)]: 52.0, 53.6, 60.6, 65.3, 71.1, 76.2, 97.8, 112.6, 112.8, 119.8 (q, J=271 Hz), 121.3, 124.2, 126.7, 127.9, 128.3, 128.5, 131.0, 132.6, 142.6, 155.7 (q, J=38 Hz), 157.2, 171.7

III-144 (E)-1-[4-(10,11-Dihydro-5H-dibenzo[a,d]cyclohepten-5-yl)-piperazin-1-yl]-3-{2-[2-(3-trifluoromethyl-isoxazol-5-yl)-ethenyl]-phenoxy}-propan-2-ol The reaction was carried according to example III-1 using 10,11-dihydro-5H-dibenzo[a,d]cyclohepten-5-yl-piperazine and epoxide IIIa-4.

$^{13}$C-NMR [CDCl$_3$, δ (ppm)] (citrate): 31.7, 51.9, 53.2, 60.5, 65.3, 71.0, 79.0, 97.8, 112.6, 112.8, 119.8 (q, J =276 Hz), 121.3, 124.2, 125.5, 127.5, 128.3, 130.8, 131.0, 132.6, 139.1, 139.7, 156.0 (q, J=52 Hz), 157.2, 171.7

III-145 (E)-1-[Bis(4-fluorophenyl)-methyl-piperazin-1-yl]-3-{2-[2-(3-isopropyl-isoxazol-5-yl )-ethenyl]-phenoxy}-propan-2-ol The reaction was carried out according to example III-1 using bis(4-fluoro-phenyl)-methyl-piperazine and (E)-5-{2-[2-(2,3-epoxypropoxy)-phenyl]-ethenyl}-3-(isopropyl)isoxazole.

$^{13}$C-NMR [CDCl$_3$; δ (ppm)](citrate): 21.7, 26.5, 44.2, 48.2, 60.8, 65.8, 71.0, 73.4, 100.1, 112.7, 113.6, 115.7, 115.9, 124.5, 126.9, 128.5, 129.0, 129.3, 156.0, 160.6, 161.9 168.2 (J=244 Hz), 169.8, 173.9, 178.6

III-146 (E)-1-[4-(2-Hydroxy-3-{2-[2-(3-isopropyl-isoxazol-5-yl)-ethenyl]-phenoxy}-propyl)-piperazin-1-yl]-2,2-diphenyl-ethanone The reaction was carried out according to example III-1 using 2,2-diphenyl-acetylpiperazine and (E)-5-{2-[2-(2,3-epoxypropoxy)-phenyl]-ethenyl}-3-(isopropyl)-isoxazole.

$^{13}$C-NMR [DMSO; δ (ppm)] (citrate): 21.4, 25.8, 41.6, 45.4, 52.6, 53.1, 53.4, 60.8, 66.4, 71.3, 99.9, 112.6, 113.9, 120.6, 123.9, 126.5, 127.6, 128.1, 128.8, 128.9, 130.3, 140.1, 156.6, 168.1, 169.2, 169.3

III-147 (E)-1-[4-(10,11-Dihydro-5H-dibenzo[a,d]cyclohepten-5-yl)-piperazin-1-yl]-3-{2-[2-(3-methoxy-isoxazol-5-yl)-ethenyl]-phenoxy}-propan-2-ol The reaction was carried out according to example III-1 using 10,11-dihydro-5H-dibenzo[a,d]cyclohepten-5-yl)-piperazine and epoxide IIIa-5.

$^{13}$C-NMR [CDCl$_3$, δ (ppm)]: 31.7, 51.9, 53.8, 56.9, 60.5, 65.3, 71.0, 79.1, 91.8, 112.5, 114.3, 121.2, 124.8, 125.5, 127.7, 127.8, 130.0, 130.2, 130.7, 130.8, 139.2, 139.7, 156.9, 169.8, 172.6

III-148 (Z)-1-[4-(10,11-Dihydro-5H-dibenzo[a,d]cyclohepten-5-yl)-piperazin-1-yl]-{2-[2-(3-methoxy-isoxazol-5-yl)-ethenyl]-phenoxy}-propan-2-ol $^{13}$C-NMR [CDCl$_3$; δ (ppm)]: 31.8, 51.9, 53.8, 56.9, 60.4, 65.3, 70.8, 79.1, 93.2, 112.1, 116.1, 120.8, 125.1, 125.5, 127.7, 127.8, 129.7, 130.7, 130.8, 132.0, 139.2, 139.7, 156.1, 168.5, 172.2

III-149 (E)-1-[(4-Diphenyl-methyl)-piperazin-1-yl)]-3-{2-[2-(3-methoxy-isoxazol-5-yl)-ethenyl]-phenoxy}-propan-2-ol The reaction was carried out according to example III-1 using 4-(diphenyl-methyl)-piperazine and epoxide IIIa-5.

$^{13}$C-NMR [CDCl$_3$, δ (ppm)]: 52.0, 5.6, 56.9, 60.7, 65.4, 71.0, 76.2, 91.8, 112.5, 114.3, 121.2, 124.8, 127.0, 127.8, 127.9, 128.5, 130.1, 130.3, 142.7, 156.9, 169.8, 172.6

III-150 (Z)-1-[(4-Diphenyl-methyl)-piperazin-1-yl)-3-{2-[2-(3-methoxy-isoxazol-5-yl)-ethenyl]-phenoxy}-propan-2-ol $^{13}$C-NMR [CDCl$_3$; δ (ppm)]: 52.0, 53.6, 56.9, 60.5, 65.4, 70.8, 76.2, 93.2, 112.1, 116.1, 120.8, 125.2, 127.0, 127.8, 127.9, 128.5, 129.7, 132.0, 142.7, 156.1, 168.5, 172.2

III-151 (E)-1-[4-(Diphenyl-methylidene)-piperidin-1-yl]-3-{2-[2-(5-methoxymethyl-isoxazol-3-yl)-ethenyl]-phenoxy}-propan-2-ol The reaction was carried out according to example III-118 using epoxide IIIa-5.

$^{13}$C-NMR [CDCl$_3$; δ (ppm)]: 31.7, 55.4, 58.9, 60.6, 65.4, 65.7, 71.2, 99.9, 112.6, 116.6, 121.3, 125.2, 126.4, 127.5, 128.0, 129.8, 130.0, 131..1, 134.8, 136.4, 142.4, 156.6, 162.3, 168.9

III-152 (E)-3-{2-[2-(3,5-Dimethyl-isoxazol-4-yl)-ethenyl]-phenoxy}-1-[4diphenylmethylidene-piperidin-1-yl]-propan-2-ol The reaction was carried out according to example III-118 using (E)-4-{2-[2-(2,3-epoxypropoxy)-phenyl]-ethenyl}-3,5-dimethyl-isoxazole.

$^{13}$C-NMR [CDCl$_3$; δ (ppm)]: 11.7, 11.9, 31.7, 55.6, 60.8, 65.7, 70.9, 112.4, 113.6, 116.9, 121.2, 125.0, 126.2, 126.5, 126.6, 128.1, 128.8, 129.7, 134.6, 136.6, 142.3, 155.9, 158.3, 165.4

III-153 (E)-1-[exo-6,7-Diphenyl-3-azabicyclo[3.2.0]hept-3-yl]-3-{2-[2-(3-isopropyl-isoxazol-5-yl)-ethenyl]-phenoxy}-propan-2-ol The reaction was carried out according to example III-1 using exo-6,7-diphenyl-3-azabicyclo[3.2.0]heptane and (E)-5-{2-[2-(2,3-epoxypropoxy)-phenyl]-ethenyl}-3-(isopropyl)-isoxazole.

$^{13}$C-NMR [DMSO; δ (ppm)] (citrate): 21.4, 25.8, 39.3, 39.7, 43.3, 46.0, 46.1, 57.5, 59.8, 60.1, 66.2, 68.5, 71.9, 100.1, 112.8, 114.0, 121.0, 124.0, 125.4, 127.5, 127.9, 128.3, 128.6, 128.7, 130.4, 140.4, 140.5, 156.4, 168.1, 169.2, 171.3, 175.6.

III-154 (E)-1-[exo-(6-tert.Butyl-phenyl)-3-azabicyclo[3.2.0]hept-3-yl]-3-{2-[2-(5-methoxymethyl-isoxazol-3-yl)-ethenyl]-phenoxy}-propan-2-ol The reaction was carried out according to example III-1 using exo-(6-tert.butyl-phenyl)-3-azabicyclo[3.2.0]heptane and epoxide IIIa-7.

$^{13}$C-NMR [CDCl$_3$; δ (ppm)] (citrate): 31.4, 34.4, 44.5, 58.7, 58.9, 65.7, 65.9, 70.5, 73.1, 100.3, 112.7, 117.0, 121.5, 124.7, 125.5, 126.1, 128.5, 130.3, 131.9, 140.8, 149.4, 156.3, 162.2, 169.1, 174.1, 179.3.

III-155 (E)-1-[4-(2,2-Diphenyl-acetyl)-piperazin-1-yl]-3-{2-[2-(3-trifluoromethyl-isoxazol-5-yl)-ethenyl]-phenoxy}-propan-2ol The reaction was carried out according to example III-1 using 2,2-diphenyl-acetylpiperazine and epoxide IIIa-7.

$^{13}$C-NMR [CDCl$_3$; δ (ppm)]: 42.2, 46.0, 53.2, 54.9, 60.5, 65.7, 70.9, 97.9, 112.6, 119.8 (q, J=270 Hz), 121.4, 124.2, 127.1, 128.1, 128.6, 129.0, 131.0, 132.4, 139.3, 155.6 (q, J=31 Hz), 157.1, 170.3, 171.6.

III-156 ( E)-1-[Bis(4-fluorophenyl)-methyl-piperazin-1-yl]-3-{2-[2-(3trifluoromethyl-isoxazol-5-yl)-ethenyl]-phenoxy}-propan-2ol The reaction was carried out according to example III-1 using bis(4-fluorophenyl)-methyl-piperazine and epoxide IIIa-7.

Mp.: 65°–6 7° C.

III-157 (E)-1-[4-(2,2-Diphenyl-acetyl)-piperazin-1-yl]-3-{2-[2-(2-methylmethoxy-1,3-thiazol-4-yl)-ethenyl]-phenoxy}-propan-2ol The reaction was carried out according to example III-1 using 2,2-diphenyl-acetyl-piperazine and epoxide IIIa-8.

Mp.: 89°–90° C. (citrate)

III-158 (E)-1-[10,11-Dihydro-5H-dibenzo[a,d]cyclohepten-5-yl)-piperazin-1-yl]-3-{2-[(2-methoxymethyl-1,3,4-thiadiazol-5-yl)-ethenyl]-phenoxy}-propan-2-ol The reaction was carried out following the same procedure as described for example III-1 using 10,11-dihydro-5H-dibenzo[a,d]cyclohepten-5-yl)-piperazine and epoxide IIIa-18.

Mp.: 100°–102° C. (the compound starts sintering from 80° C. on)

III-159 (E)-1-[4-(Diphenyl-methyl)-piperazin-1-yl]-3-{2-[(2-methoxymethyl-1,3,4-thiadiazol-5-yl)-ethenyl]-phenoxy}-propan-2-ol The reaction was carried out following the same procedure as described for example III-1 using 4-(diphenyl-methyl)-piperazine and epoxide IIIa-18.

$^{13}$C-NMR (DMSO; δ (ppm)] (citrate): 43.6, 50.2, 53.0, 58.2, 60.0, 65.3, 67.8, 71.2, 71.6, 74.5, 112.7, 118.2, 120.9, 123.5, 126.9, 127.1, 127.4, 127.5, 128.0, 128.5, 128.6, 131.0, 133.9, 141.7, 142.4, 151.7, 156.6, 166.7, 168.7, 171.2; 175.9.

III-160 (E)-1-[4-(2,2-Diphenyl-acetyl)-piperazin-1-yl]-3-{2-[(2-methoxymethyl-1,3,4-thiadiazol-5-yl)-ethenyl]-phenoxy}-propan-2-ol The reaction was carried out following the same procedure as described for example III-1 using 2,2-diphenyl-acetyl-piperazine and epoxide IIIa-18.

$^{13}$C-NMR (CDCl$_3$: δ (ppm)] (citrate): 42.2, 46.0, 53.1, 53.2, 54.9, 59.0, 60.6, 69.0, 70.8, 112.6, 119.0, 121.8, 124.5, 127.1, 128.2, 128.6, 129.0, 130.8, 134.6, 139.4, 156.8, 166.7, 169.8, 170.3.

III-161 (Z)-1-[10,11-Dihydro-5H-dibenzo[a,d]cyclohepten-5-yl)-piperazin-1-yl]-3-{2-[(2-methoxymethyl-1,3,4-thiadiazol-5-yl)-ethenyl]-phenoxy}-propan-2-ol The reaction was carried out following the same procedure as described for example III-1 using 10,11-dihydro-5H-dibenzo[a,d]cyclohepten-5-yl)-piperazine and epoxide IIIa-18.

$^{13}$C-NMR (DMSO; δ (ppm)] (citrate): 30.9, 43.4, 49.5, 52.5, 58.2, 64.6, 67.6, 70.6, 71.8, 77.1, 112.7, 120.9, 123.9, 125.5, 127.8, 129.7, 130.4, 130.6, 135.1, 138.6, 139.0, 155.7, 164.6, 167.1, 171.3, 175.7.

III-162 (E)-1-[4-(Diphenyl-methylidene)-piperidine-1-yl]-3-{2-[2-(3-trifluoromethyl-isoxazol-5-yl)-ethenyl]-phenoxy}-propan-2-ol The reaction was carried out following the same procedure as described for example III-118 using epoxide IIIa-4.

$^{13}$C-NMR (CDCl$_3$; δ (ppm)]: 31.7, 55.6, 60.6, 65.5, 71.1, 97.8, 112.7, 119.8 (q, J=270 Hz), 121.3, 126.5, 128.2, 128.3, 129.4, 129.8, 131.0, 132.6, 134.5, 136.6, 142.3, 155.5 (q, J=36 Hz), 157.2, 171.7.

III-164 (E)-1-[4-(Diphenyl-methylidene)-piperidine-1-yl]-3-{2-[(2-methoxymethyl-1,3,4-thiadiazol-5-yl)-ethenyl]-phenoxy}-propan-2-ol The reaction was carried out following the same procedure as described for example III-118 using and epoxide IIIa-18.

Mp.: 130°–132° C.

III-165 (E)-1-[4-(Diphenyl-methylidene)-piperidin-1-yl]-3-{2-[(3-methoxymethyl-isoxazol-5-yl)-ethenyl]-phenoxy}-propan-2-ol The reaction was carried out following the same procedure as described for example III-118 using epoxide IIIa-1.

Mp.: 90°–91° C.

III-166 (Z)-1-[4-(Diphenyl-methylidene)-piperidin-1-yl-3-{2-[(3-methoxymethyl-isoxazol-5-yl)-ethenyl]-phenoxy}-propan-2-ol The reaction was carried out following the same procedure as described for example III-118 using and the crude epoxide IIIa-15.

$^{13}$C-NMR (DMSO; δ (ppm)] (citrate): 33.3, 43.5, 45.4, 51.0, 58.5, 60.7, 64.2, 65.6, 70.3, 73.4, 101.8, 112.1, 115.6, 121.0, 124.9, 126.7, 129.0, 129.7, 130.2, 131.9, 155.4, 161.2, 168.2, 175.6, 179.9.

III-171 (E)-1-[4-(10,11-Dihydro-dibenzo[a,d]cyclohepten-5-yliden)-piperidin-1-yl]-3-{2-[2-(3-methylmethoxy-isoxazol-5-yl)-ethenyl]-phenoxy}-propan-2-ol The reaction was carried out following the same procedure as described for example III-1 using 4-(10,11-dihydro-dibenzo[a,d]cyclohepten-5-yliden)-piperazine and epoxide IIIa-1.

$^{13}$C-NMR (CDCl$_3$; δ (ppm)]: 31.0, 31.1, 32.5, 54.8, 55.9, 58.5, 60.6, 65.6, 65.9, 71.0, 100.2, 112.5, 113.9, 121.2, 124.9, 125.5, 126.9, 127.9, 128.8, 129.3, 130.3, 130.4, 133.6, 135.1, 138.0, 140.7, 157.0, 161.7, 169.6.

III-179 (E)-1-[4-(10,11-Dihydro-dibenzo[a,d]cyclohepten-5-yliden)-piperidin-1-yl]-3-{2-[2-(2-methoxymethyl-1,3-thiazol-4-yl)-ethenyl]-phenoxy}-propan-2-ol The reaction was carried out following the same procedure as described for example III-1 using 4-(10,11-dihydro-dibenzo[a,d]cyclohepten-5-yliden)-piperazine and epoxide IIIa-8.

$^{13}$C-NMR (CDCl$_3$; δ (ppm)]: 30.9, 31.0, 32.5, 54.9, 56.0, 59.0, 60.6, 65.9, 71.1, 71.6, 112.5, 115.0, 121.1, 122.1, 125.5, 126.9, 127.2, 128.1, 128.8, 129.3, 133.7, 134.9, 137.9, 140.6, 154.7, 156.4, 168.7.

IV-1 (E)-1-[4-(Diphenyl-methyl)-piperazin-1-yl]-3-{2-[2-(3-methoxymethyl-isoxazol-5-yl)-ethenyl]-phenoxy}-propan a) 1.13 g of sodium hydride (60% in mineral oil) were washed with pentane to remove the mineral oil, and dry dimethylformamide (30 ml) was added. 4 g of (E)-5-[{2-hydroxy-phenyl}-ethenyl]-3-(methoxymethyl)-isoxazole —dissolved in 20 ml of dimethylformamide— were added slowly through a dropping funnel, and after gas evolution had ceased the mixture was stirred for another 15 min. at 40° C. After cooling to 4° C. 6.95 g of 1,3-dibromopropane were added slowly. The mixture was stirred at room temperature until the reaction was finished. Afterwards the reaction mixture was diluted with cold water, extracted with ethyl acetate, the organic phase washed with saturated sodium chloride solution and then dried with magnesium sulfate. Evaporation of the solvent and chromatography on silica gel afforded 4.3 g of (E)-3-{2-[2-(3-methoxymethyl-isoxazol-5-yl)-ethenyl]-phenoxy}-propanylbromide as oil.

b) 1.2 g of 4-(diphenyl)-methyl-piperazine, 1 g of the above mentioned bromide and 0.3 ml N-methylmorpholine were refluxed in 10 ml ethanol. After the reaction was finished the solvent was evaporated and the crude product purified by chromatography on silica gel. The pure product was obtained as an oily residue which was precipitated as corresponding citrate.

$^{13}$C-NMR [DMSO; δ (ppm)] (citrate): 24.7, 43.5, 49.7, 52.0, 53.7, 57.8, 64.8, 65.8, 71.7, 74.2, 101.1, 112.6, 113.6, 120.8, 123.7, 126.9, 127.5, 127.6, 128.5, 129.1, 130.5, 142.2, 156.3, 161.5, 168.4, 171.2, 175.7

IV-2 (E)-I-[10,11-Dihydro-5H-dibenzo[a,d]cyclohepten-5-yl]-piperazin-1-yl]-3-{2-[2-(3-methoxymethyl-isoxazol-5-yl)-ethenyl]-phenoxy}-propan The reaction was carried out following the same procedure described for example IV-1 using 10,11-dihydro-5H-dibenzo[a,d]cyclohepten-5-yl-piperazine and (E)-3-{2-[2-(3-methoxymethyl-isoxazol-5-yl)-ethenyl]-phenoxy}-propanylbromide.

¹³C-NMR [DMSO; δ (ppm)] (citrate): 24.7, 30.9, 38.8, 43.5, 49.7, 52.0, 53.5, 57.8, 64.8, 71.7, 101.2, 112.6, 113.6, 120.1, 123.7, 125, 5, 127.6, 127.8, 129.1, 130.4, 130.5, 130.6, 138.6, 139.0, 156.3, 161.5, 168.6, 171.2, 175.7

IV-3 (E)-1-[4-(Diphenyl-methyliden)-piperidin-1-yl]-3-{2-[2-(3-methoxymethyl-isoxazol-5-yl)-ethenyl]-phenoxy}-propan The reaction was carried out following the same procedure described for example IV-1 using 4-(diphenyl-methyliden)-piperidine-hydrochloride, (E)-3-{2-[2-(3-methoxymethyl-isoxazol-5-yl)-ethenyl]-phenoxy}-propanylbromide.

Mp.: 205°–207° C. (hydrochloride) ¹³C-NMR [DMSO; δ (ppm)] (hydrochloride): 23.5, 27.8, 52.3, 52.9, 57.8, 64.8, 65.4, 101.3, 112.6, 113.8, 123.7, 126.9, 127.6, 128.3, 129.1, 130.5, 137.8, 141.1, 156.1, 161.5, 168.6

V-1 1-[10,11-Dihydro-5H-dibenzo[a,d]cyclohepten-5-yl]-piperazin-1-yl]-3-{2-[(3-methoxymethyl-isoxazol-5-yl)-methoxy]-phenoxy}-propan-2-ol The reaction was carried out following the same procedure described for example III-1 using 10,11-dihydro-5H-dibenzo[a,d]cyclohepten-5-yl-piperazine and 5-{[2-(2,3-epoxy-propoxy)-phenyl]-methoxy}-3-(methoxymethyl)-isoxazole.

Mp.: 99.5°–102° C. ¹³C-NMR [CDCl₃; δ (ppm)]: 31.8, 52.0, 53.7, 58.5, 60.4, 63.2, 65.7, 72.0, 79.1, 102.6, 115.0, .116.6, 121.7, 123.2, 125.5, 127.7, 130.7, 139.2, 139.7, 147.8, 149.7, 161.4, 168.7

V-2 1-[10,11-Dihydro-5H-dibenzo[a,d]cyclohepten-5-yl]-piperazin-1-yl]-3-{2-[(3-methoxymethyl-isoxazol-5-yl)-methoxymethyl]-phenoxy}-propan-2-ol The reaction was carded out following the same procedure described for example III-1 using 10,11-dihydro-5H-dibenzo[a,d]cyclohepten-5-yl-piperazine and 5-{[2-(2,3-epoxypropoxy )-phenyl]-methoxymethyl}-3-(methoxymethyl)-isoxazol (precursor Va-1).

Mp.: 145°–146° C. (hydrochloride) ¹H-NMR [CDCl₃; δ (ppm)] (hydrochloride): 2.20–2.63 (m, 10H), 2.72–2.88 (m, 3H), 3.39 (s, 3H), 3.45–3.60 (m, 2H), 3.78–4.08 (m, 4–5H), 4.55 (s, 2H), 4.65 (s, 2H), 5.17 (s, 2H), 6.38 (s, 1H), 6.88–7.45 (m, 12H)

V-3 1-[4-(Diphenyl-methyl)-piperazin-1-yl]-3-{2-[(3-methoxymethyl-isoxazol-5-yl)-methoxymethyl)]-phenoxy}-propan-2-ol The reaction was carded out according to example III-1 using 4-(diphenyl-methyl)-piperazine and precursor Va-1.

Mp.: 123°–125° C. (oxalate) ¹H-NMR [DMSO; δ (ppm)] (oxalate): 2.40–2.75 (m, 8H), 3.05–3.35 (m, 7H), 3.35–3.55 (m, 2H), 4.10 (m, 1H), 4.44 (s, 1H), 4.49 (s, 2H), 4.52 (s, 2H), 5.35 (s, 2H), 6.65 (s, 1H), 7.0 (m, 1H), 7.10–7.48 (m, 13H)

V-4 1-[4-(Diphenyl-methyl)-piperazin-1-yl]-3-{2-[(3-methoxymethyl-isoxazol-5-yl)-methoxy]-phenoxy}-propan-2-ol The reaction was carded out following the same procedure described for example III-1 using 4-(diphenyl-methyl)-piperazine and 5-{[2-(2,3-epoxypropoxy)-phenyl]-methoxy}-3-(methoxymethyl)-isoxazole.

Mp.: 117.5°–119° C. ¹³C-NMR [CDCl₃; δ (ppm)]: 52.0, 53.6, 58.5, 60.5, 63.2, 65.7, 72.0, 76.2, 102.6, 115.0, 116.6, 121.7, 123.2, 127.0, 128.0, 142.7, 147.9, 149.7, 161.4, 168.7

V-5 1-[4-(Cyclohexyl-phenyl)-methyl-piperazin-1-yl]-3-{2-[(3-methoxymethyl-isoxazol-5-yl)-methoxy]-phenoxy}-propan-2-ol The reaction was carded out following the same procedure described for example III-1 using 4-(cyclohexyl-phenyl)-methyl-piperazine and 5-{[2-(2,3-epoxypropoxy)-phenyl]methoxy}-3-(methoxymethyl)-isoxazole.

¹³C-NMR [DMSO; δ (ppm)] (citrate) : 25.4, 25.5, 26.3, 29.5, 29.6, 30.4, 36.4, 43.7, 46.6, 52.9, 57.9, 59.5, 61.4, 64.6, 64.7, 71.4, 71.5, 73.4, 103.5, 114.5, 115.5, 121.2, 122.4, 126.8, 127.7, 129.0, 136.3, 147.1, 148.6, 151.8, 161.1, 168.2, 171.2, 176.2

V-6 1-[4-Diphenyl-methyl-piperazin-1-yl]-3-{2-[(3-methyl-isoxazol-5-yl)-methoxy]-phenoxy}-propan-2-ol The reaction was carried out following the same procedure described for example III-1 using 4-(diphenyl)-methyl-piperazine and 5-{[2-(2,3-epoxypropoxy)-phenyl]-methoxy}-3-(methoxymethyl)-isoxazole.

Mp: 102°–105° C. (hydrochloride)

V-53 1-[4-(Diphenyl-methyliden)-piperidin-1-yl]-3-{2-[(3-methoxymethyl-isoxazol-5-yl)-methoxymethyl]-phenoxy}-propan-2-ol The reaction was carried out following the same procedure described for example III-118 using 10,11-dihydro-5H-dibenzo[a,d]cyclohepten-5-yl-piperazine and precursor Va-1.

¹³C-NMR [CDCl₃; δ (ppm)] (citrate): 31.7, 55.5, 58.6, 60.6, 61.7, 65.7, 66.4, 68.2, 73.2, 102.5, 111.7, 121.9, 126.4, 127.5, 128.0, 128.8, 129.4, 129.8, 135.1, 136.2, 142.5, 155.4, 161.5, 168.4

V-54 1-[4-(Diphenyl-methyliden)-piperidin-1-yl]-3-{2-[3-methoxymethyl-isoxazole-5-yl-methoxy]-phenoxy}-propan-2-ol The reaction was carried out following the same procedure described for example III-118 using 5-{[2-(2,3-epoxypropoxy)-phenyl]-methoxy}-3-(methoxmethyl)-isoxazole.

¹³C-NMR [CDCl₃; δ (ppm)] (citrate): 31.7, 55.5, 58.6, 60.6, 61.7, 65.7, 66.4, 68.2, 73.2, 102.5, 111.7, 121.9, 126.4, 127.5, 128.0, 128.8, 129.4, 129.8, 135.1, 136.2, 142.5, 155.4, 161.5, 168.4

VI-1 (3-{2-[2-(4,5-Dimethyl-1,3-oxazol-2-yl)-ethyl]-phenoxy}-1-(4-diphenylmethyl-piperazin-1-yl)-propan-2-ol 3 ml of a 1 N solution of tetrabutylammonium fluoride in tetrahydrofuran were added to a solution of 1 g of 2-[2-(2-tert.butyldimethylsiloxy-phenyl)-ethyl]-4,5-dimethyl-oxazole in 20 ml tetrahydrofuran. After stirring for 3 h the reaction mixture was given into 20 ml 0.1 N HCl and the solution extracted with ether. After drying over sodium sulfate the solvent was removed in vacuo. The residue was dissolved in 20 ml butanol. 0.4 g potassium carbonate and 0.92 g 4-diphenylmethyl-1-(2,3-epoxypropyl)-piperazine were added and the mixture refluxed for 2 hours. The solvent was removed in vacuo, the residue dissolved in saturated ammonium chloride and extracted with ethyl acetate. After drying of the organic phase over sodium sulfate the solvent was removed in vacuo and the residue purified by flash chromatography to give 0.66 g of (3-{2-[2-(4,5-dimethyl-1,3-oxazol-2-yl)-ethyl]-phenoxy}-1-(4-diphenylmethyl-piperazin-1-yl)-propan-2-ol. The corresponding citrate was obtained by treatment of a solution of the alcohol with citric acid.

¹³C-NMR [CDCl₃; δ (ppm)] (citrate): 9.8, 10.4, 28.1, 28.6, 44.5, 48.6, 53.4, 60.3, 64.5, 69.8, 72.9, 75.2, 111.5, 121.2, 127.6, 127.8, 128.0, 128.5, 128.9, 129.2, 130.0, 141.1, 143.0, 156.1, 162.3, 173.6, 179.2

VII-6 1-[(4-Diphenyl-methyl-piperazin-1-yl]-3-{2-[(3-methyl-isoxazol-5-yl)-ethinyl]-phenoxy]-propan-2-ol 3.9 ml of a 1 N tetrabutylammonium fluoride in tetrahydrofuran were added to a solution of 1.1 g of 2-(3-methyl-isoxazol-5-yl-ethinyl)-phenyl-tert.butyldimethylsilyl-ether (precursor VIIc) in 10 ml of tetrahydrofuran. After stirring at room temperature overnight the solution was poured into 1 N HCl, then extracted with ethylacetate. After drying the organic phase and evaporation of the solvent the residue was dissolved in acetonitrile. Then 0.6 g of potassium carbonate and 0.6 g of epibromohydrine were added and the reaction mixture refluxed for 2 h. After cooling the salts were filtered off, the filtrate evaporated, the obtained residue dissolved in ethylacetate and washed with water. The organic phase was dried over magnesium sulfate. After evaporation of the solvent the residue was dissolved in anhydrous ethanol, 1.1 g of diphenylmethyl-piperazine added and refluxed for 2 h. After cooling and evaporation of the solvent the residue was purified by chromatography on silica gel to give 0.36 g of the product.

$^{13}$C-NMR [CDCl$_3$; δ (ppm)] 11.4, 51.9, 53.6, 60.4, 65.5, 71.0, 76.2, 79.7, 94.8, 108.2, 110.9, 112.5, 121.0, 126.9, 127.9, 128.5, 131.4, 133.4, 142.7, 153.5, 159.8.

VIII-1  1-[10,11-Dihydro-5H-dibenzo[a,d]cyclohepten-5-yl)-piperazin-1-yl]-3-{2-[(3-methoxymethyl-isoxazol-5-yl)-carbonyl]-phenoxy}-propan-2-ol The reaction was carried out following the same procedure as described for example III-1 using 10,11-dihydro-5H-dibenzo[a,d]cyclohepten-5-yl)-piperazine and epoxide VIIIa-1.

$^{13}$C-NMR (DMSO; δ (ppm)] (citrate): 30.9, 43.0, 48.9, 58.0, 63.9, 64.5, 70.6, 79.0, 109.1, 113.2, 120.9, 125.5, 126.4, 127.8, 129.7, 130.4, 130.6, 134.0, 138.4, 140.0, 156.7, 162.0, 166.2, 171.2, 175.0, 182.3.

VIII-2  1-[4-(Diphenyl-methyl)-piperazin-1-yl]-3-{[2-(3-methoxymethyl-isoxazol-5-yl)-carbonyl]-phenoxy}-propan-2-ol The reaction was carried out following the same procedure as described for example III-1 using 4-(diphenylmethyl)-methyl-piperazine and epoxide VIIIa-1.

$^{13}$C-NMR (DMSO; δ (ppm)] (citrate): 43.4, 49.8, 52.6, 58.0, 59.3, 64.5, 64.6, 70.8, 71.7, 74.4, 109.0, 113.2, 120.8, 126.4, 126.9, 127.4, 128.5, 129.6, 134.0, 142.3, 156.8, 161.9, 166.2, 171.2, 175.6, 182.4.

VIII-3  1-[(2,2-Diphenyl-acetyl)-piperazin-1-yl]-3-{2-[(3-methoxymethyl-isoxazol-5-yl)-carbonyl]-phenoxy}-propan-2-ol The reaction was carried out following the same procedure as described for example III-1 using 2,2-diphenyl-acetyl-piperazine and epoxide VIIIa-1.

$^{13}$C-NMR (DMSO; δ (ppm)] (citrate): 41.0, 42.8, 44.8, 52.5, 52.6, 52.9, 58.0, 59.9, 64.5, 65.5, 71.0, 72.1, 108.9, 113.1, 120.7, 126.5, 128.0, 128.8, 129.6, 134.0, 140.0, 157.0, 161.9, 166.3, 169.4, 171.2, 174.9, 182.5.

VIII-5  1-[4-(Diphenyl-methyliden)-piperidin-1-yl]-3-{[2-(3-methoxymethyl-isoxazol-5-yl)-carbonyl]-phenoxy}-propan-2-ol The reaction was carried out following the same procedure as described for example III-1 using 4-(diphenyl-methyliden)-piperidine and epoxide VIIIa-1.

$^{13}$C-NMR (DMSO; δ (ppm)] (citrate): 29.1, 43.4, 53.9, 58.0, 59.0, 64.4, 64.5, 70.7, 71.7, 109.1, 113.2, 120.8, 126.4, 126.6, 128.2, 129.2, 129.7, 134.0, 136.5, 141.4, 151.8, 156.7, 162.0, 166.2, 171.2, 175.7, 182.3.

VIII-25  1-[2-{3-[4-(10,11-Dihydro-dibenzo[a,d]cyclohepten-5-yl)-piperazin-1-yl]-2-hydroxy-propoxy}-phenyl]-3-phenyl-propan-1-one The reaction was carried out according to example III-i using 10,11-dihydro-dibenzo[a,d]cyclohepten-5-yl)-piperazine and 1-[2-(2,3-epoxypropoxy)-phenyl]-propan-1-one.

$^{13}$C-NMR (CDCl$_3$; δ (ppm)]: 30.2, 31.8, 51.9, 60.8, 65.1, 70.8, 79.0, 112.6, 121.0, 125.9, 127.0, 128.2, 128.4, 130.5, 130.7, 133.4, 139.1, 139.2, 139.6, 141.6, 157.8, 201.1.

VIII-26  1-[2-{3-[4-(Diphenyl-methyl)-piperazin-1-yl]-2-hydroxy-propoxy}phenyl]-3-phenyl-propan-1-one The reaction was carried out according to example III-1 using 4-(diphenyl-methyl)-piperazine and 1-[2-(2,3-epoxypropoxy)-phenyl]-propan-1-one.

$^{13}$C-NMR (CDCl$_3$; δ (ppm)]: 30.3, 45.7, 52.9, 53.4, 60.8, 65.2, 70.9, 76.1, 112.6, 121.0, 125.9, 127.0, 127.9, 128.3, 128.4, 128.5, 130.5, 133.5, 141.7, 142.6, 142.7, 157.8, VIII-27  1-[2-{3-[4-Bis(4-fluorophenyl-methyl)-piperazin-1-yl]-2-hydroxy--propoxy}-phenyl]-3-phenyl-propan-1-one The reaction was carried out according to example III-1 using bis(4-fluorophenyl)-methyl-piperazine and 1-[2-(2,3-epoxypropoxy)-phenyl]-propan-1-one.

$^{13}$C-NMR (CDCl$_3$; δ (ppm)]: 30.3, 45.6, 51.8, 53.4, 60.7, 65.3, 70.9, 74.4, 112.7, 115.4 (d, J=20Hz), 121.1, 125.9, 128.4, 129.3, 130.4, 133.4, 138.1, 141.7, 157.8, 161.8 (d, J=245 Hz), 201.2.

VIII-68  1-[2-{3-[4-(2,3,4-Trimethoxyphenyl)-methyl)-piperazin-1-yl]-2-hydroxy-propoxy}-4,5-dimethoxy-phenyl]-3-phenyl-propan-1-one 5.2 g of 2-[(2,3-epoxypropoxy)-4,5-dimethoxy-3-phenyl-propanone (epoxide VIIIa-2) and 6.7 g of 4-(2,3,4-trimethoxyphenyl)-methyl)-piperazine were refluxed in 60 ml of isopropanol. After the reaction was completed the solvent was evaporated and the obtained residue purified by cromatography on silica gel yielding 8.8 g of pure product.

Mp.: 217°–218° C.

$^{13}$C-NMR [CDCl$_3$; δ (ppm)]: 30.5, 45.8, 53.0, 56.0, 56.5, 60.8, 61.2, 65.3, 71.8, 97.7, 107.0, 112.6, 119.8, 124.1, 125.8, 128.4, 128.5, 142.1, 143.3, 152.7, 153.0, 153.8, 154.4, 198.6.

According to the preparation of compound VIII-68 the following compounds were prepared.

VIII-69  1-[2-{3-[4-(Diphenyl-methyl)-piperazin-1-yl]-2-hydroxy-propoxy}-4,5-dimethoxy-phenyl]-3-phenyl-propan-1-one Mp.: 149°–150° C.

VIII-70 1-[2-{3-[4-(2,2-Diphenyl-acetyl)-piperazin-1-yl]-2-hydroxy-propoxy}-4,5-dimethoxy-phenyl]-3-phenyl-propan-1-one Mp.: 128°–129° C.

VIII-73  1-[2-{3-[4-Bis(4-fluorophenyl}-methyl)-piperazin-1-yl]-2-hydroxy-propoxy}-4,5-dimethoxy-phenyl]-3-phenyl-propan-1-one Mp.: 152°–153° C.

VIII-81 1-[2-{3-[4-(4-Trifluoromethyl-phenyl)-piperazin-1-yl]-2-hydroxy-propoxy}-4,5-dimethoxy-phenyl]-3-phenyl-propan-1-one Mp.: 140°–142° C. VIII-86 1-[2-{3-[4-(3,4,5-Trimethoxy-phenyl)-piperazin-1-yl]-2-hydroxy-propoxy}-4,5-dimethoxy-phenyl]-3-phenyl-propan-1-one Mp.: 148°–149° C.

VIII-97 1-[2-{3-[4-(4-tert.Butylphenyl)-methyl)-piperazin-1-yl]-2-hydroxy-propoxy}-4,5-dimethoxy-phenyl]-3-phenyl-propan-1-one Mp.: 120°–121° C.

VIII-98  1-[2-{3-[4-(3,4-Methylendioxy-phenyl)-methyl]-piperazin-1-yl]-2-hydroxy-propoxy}-4,5-dimethoxy-phenyl]-3-phenyl-propan-1-one Mp.: 129°–130° C.

VIII-99 1-[2-{3-[10,11-Dihydro-5H-dibenzo[a,d]-cyclohepten-5-yl)-piperazin-1-yl]-2-hydroxy-propoxy}-4,5-dimethoxy-phenyl]-3-phenyl-propan-1-one $^{13}$C-NMR [DMSO; δ (ppm)] (citrate): 197.6, 175.6, 171.2, 154.1, 153.7, 142.6, 141.6, 139.0, 138.6, 130.4, 128.2, 128.0, 127.8, 125.5, 125.4, 118.0, 112.0, 98.4, 77.1, 71.8, 64.8, 59.8, 55.9, 52.3, 49.7, 44.9, 43.4, 30.9, 29.9.

VIII-100  1-[2-{3-[4-(3,4,5-Trimethoxyphenyl)-methyl]-piperazin-1-yl]-2-hydroxy-propoxy}-4,5-dimethoxy-phenyl]-3-phenyl-propan-1-one Mp.: 126°–127° C.

VIII-109 1-[2-{3-[2-(2,3-Dimethoxy-phenyl)-ethyl]-piperazin-1y-l]-2-hydroxy-propoxy}-4,5-dimethoxy-phenyl]-3-phenyl-propan-1-one
Mp.: 104°–105° C.

VIII-117 1-[2-{3-[4-(Diphenyl-methyliden)-piperazin-1-yl]-2-hydroxy-propoxy}-4,5-dimethoxy-phenyl]-3-phenyl-propan-1-one
Mp.: 142°–143° C. VIII-118 1-[2-{3-(Exo-6,7-diphenyl-3-aza-bicyclo[3.2.0]-heptan-3-yl)-2-hydroxy-propoxy}-4,5-dimethoxy-phenyl]-3-phenyl-propan-1-one
Mp.: 134°–135° C.

VIII-119 1-[2-{3-(Exo-6-phenyl-3-aza-bicyclo[3.2.0]-heptan-3-yl)-2-hydroxy-propoxy}-4,5-dimethoxy-phenyl]-3-phenyl-propan-1-one
Mp.: 134°–135° C. (HCl-salt)

VIII-133 1-[2-{3-(4,4-Diphenyl-piperidin-1-yl)-2-hydroxy-propoxy}4,5-dimethoxy-phenyl]-3-phenyl-propan-1-one
Mp.: 152°–154° C.

VIII-141 1-[2-{3-[10,11-Dihydro-dibenzo[a,d]-cyclohepten-5-yliden]-piperidin-1-yl]-2-hydroxy-propoxy}-4,5-dimethoxy-phenyl]-3-phenyl-propan-1-one
$^{13}$C-NMR [DMSO; δ (ppm)] (citrate): 28.6, 29.9, 31.6, 43.5, 44.9, 53..6, 54.1, 55.7, 55.9, 59.7, 64.8, 71.7, 98.4, 112.0, 118.0, 125.4, 127.1, 128.0, 128.2, 128.3, 129.4, 135.0, 137.6, 139.8, 141.6, 142.7, 153.7, 154.1, 171.2, 175.9, 197.7.

VIII-142 1-[2-{3-[4-(Phenyl-methyl)-piperazin-1-yl]-2-hydroxy-propoxy}4,5-dimethoxy-phenyl]-3-phenyl-propan-1-one
Mp.: 103°–104° C.

IX-9 1-[10,11-Dihydro-5H-dibenzo[a,d]cyclohepten-5-yl)-piperazin-1-yl]-3-{2-(2-[3-methoxymethyl-isoxazol-5-yl]-aminocarbonyl)-phenoxy}-propan-2-ol
The reaction was carried out following the same procedure described for example III-1 using 10,11-dihydro-5H-dibenzo[a,d]cyclohepten-5-yl-piperazine and epoxide IXa-2.
Mp.: 122°–124° C.

IX-10 1-[4-(Diphenyl-methyl)-piperazin-1-yl]-3-{2-(2-[3-methoxymethyl-isoxazol-5-yl]-aminocarbonyl)-phenoxy}-propan-2-ol
The reaction was carried out following the same procedure described for example III-1 using 4-(diphenyl-methyl)-piperazine and epoxide IXa-2.
Mp: 160°–161° C.

IX-13 1-[10,11-Dihydro-5H-dibenzo[a,d]cyclohepten-5-yl)-piperazin-1-yl]-3-{2-[2-(3-methoxymethyl-isoxazol-5-yl)-2-N-methyl-aminocarbonyl]-phenoxy}-propan-2-ol
The reaction was carried out following the same procedure as described for example III-1 using 10,11-dihydro-5H-dibenzo[a,d]cyclohepten-5-yl-piperazine and epoxide IXa-3.
$^{13}$C-NMR (DMSO; δ (ppm)] (citrate; mixture of rotameres): 30.9, 36.6, 43.4, 49.7, 52.6, 57.6, 59.0, 64.3, 64.6, 65.0, 70.4, 70.8, 71.8, 77.1, 105.5, 105.6, 113.3, 113.5, 121.1, 125.5, 127.7, 128.8, 130.0, 130.4, 130.6, 130.9, 138.6, 139.0, 153.7, 153.8, 157.5, 160.7, 162.9, 171.2, 175.7.

IX-14 1-[4-(Diphenyl-methyl)-piperazin-1-yl]-3-{2-(2-[3-methoxymethyl-isoxazol-5-yl)-2-N-methyl-aminocarbonyl]-phenoxy}-propan-2-ol
The reaction was carried out following the same procedure as described for example III1 using 4-(diphenyl-methyl)-piperazine and epoxide IXa-3.
$^{13}$C-NMR (DMSO; δ (ppm)] (citrate; mixture of rotameres): 36.6, 43.4, 49.7, 52.7, 57.6, 59.3, 64.3, 64.6, 65.0, 70.4, 70.8, 71.8, 74.4, 105.5, 105.6, 113.3, 113.5, 121.6, 126.9, 127.4, 128.5, 128.8, 130.0, 130.8, 130.9, 142.3, 153.7, 153.8, 157.5, 160.7, 162.9, 171.2, 175.7.

IX-15 1-[4-(2,2-Diphenyl-acetyl)-piperazin-1-yl]-3-{2-(2-[3-methoxymethyl-isoxazol-5-yl)-2-N-methyl-aminocarbonyl]-phenoxy}-propan-2-ol
The reaction was carried out following the same procedure as described for example III-1 using 2,2-diphenyl-acetyl-piperazine and epoxide IXa-3.
$^{13}$C-NMR (DMSO; δ (ppm)] (citrate; mixture of rotameres): 36.6, 42.8, 44.7, 52.5, 53.0, 57.6, 60.0, 64.2, 65.4, 65.8, 70.4, 70.9, 72.1, 105.4, 113.3, 113.5, 121.0, 126.5, 128.1, 128.9, 130.0, 130.9, 140.0, 153.0, 157.5, 160.6, 162.9, 169.4, 171.2, 174.8.

IX-17 N-(5-Methyl-isoxazol-3-yl)-2-[3-{(4-diphenyl-methyl)-piperazin-1-yl}-2-hydroxy-propoxy]-benzamide
The reaction was carried out following the same procedure described for example III-1 using 4-(diphenyl)-methyl-piperazine and epoxide IXa-1.
$^{13}$C-NMR [DMSO; δ (ppm)]: 12.0, 51.5, 53.4, 60.6, 65.9, 71.9, 75.1, 96.7, 113.7, 120.9, 122.0, 126.7, 127.4, 128.4, 130.7, 133.4, 142.8, 156.5, 157.8, 163.5, 169.4

IX-18 N-(5-Methyl-isoxazol-3-yl)-2-{3-[4-(10,11-dihydro-5H-dibenzo-[a,d]cyclohepten-5-yl)-piperazin-1-yl]-2-hydroxy-propoxy}-benzamide
The reaction was carried out following the same procedure described for example III-1 using 10,11-dihydro-5H-dibenzo[a,d]cyclohepten-5-yl-piperazine and epoxide IXa-1.
$^{13}$C-NMR [DMSO; δ (ppm)]: 12.6, 31.7, 51.9, 54.0, 59.9, 65.1, 71.2, 79.0, 97.1, 113.3, 121.3, 121.9, 125.5, 127.7, 130.7, 130.8, 132.5, 133.8, 139.3, 139.6, 157.1, 158.5, 163.3, 169.4

IX-19 N-(5-Methyl-isoxazol-3-yl)-2-{3-[4-(bis(4-fluorophenyl-methyl)-piperazin-1-yl]-2-hydroxy-propoxy}-benzamide
The reaction was carried out following the same procedure described for example III-1 using bis(4-fluoro-phenyl)-methyl-piperazine and epoxide IXa-1.
$^{13}$C-NMR [CDCl$_3$; δ (ppm)]: 12.6, 51.8, 53.4, 60.0, 65.2, 71.1, 74.5, 97.1, 113.3, 115.4 (J=21 Hz), 121.3, 121.9, 129.2 (J=8 Hz), 132.5, 133.8, 138.3, 157.1, 158.5, 161.8 (J=246 Hz), 163.3, 169.4

IX-22 1-[4-(Diphenyl-methyliden)-piperidin-1-yl]-3-{2-[3-methoxymethyl-isoxazol-5-yl]-aminocarbonyl}-propan-2-ol
The reaction was carried out following the same procedure described for example III-118 using epoxide IXa-2.
Mp.: 126.5°–127.5° C.

IX-23 1-[4-(Diphenyl-methyliden)-piperidin-1-yl]-3-{2-(2-[3-methoxymethyl-isoxazol-5-yl)-2-N-methyl-aminocarbonyl]-phenoxy}-propan-2-ol
The reaction was carried out following the same procedure as described for example III-1 using 4-(diphenyl)-methyliden-piperidine and epoxide IXa-3.
$^{13}$C-NMR (DMSO; δ (ppm)] (citrate; mixture of rotameres): 29.3, 36.6, 43.4, 54.0, 57.6, 59.0, 59.2, 64.3, 64.5, 64.9, 70.4, 70.8, 71.6, 105.6, 113.4, 113.5, 121.2, 126.6, 128.1, 128.8, 129.2, 130.0, 130.9, 136.4, 141.5, 153.6, 153.8, 157.5, 160.7, 162.9, 171.2, 175.9.

Preparation of the Starting Compounds

Epoxides of Type III-a

IIIa-1 (E)-5-{2-[2-(2,3-Epoxypropoxy)-phenyl]-ethenyl}-3-(methoxymethyl)-isoxazole 4.6 g of sodium hydride (60% in mineral oil) were washed with pentane to remove the mineral oil, then 200 ml of dry dimethylformamide added. 28.7 g of diethyl (3-methoxymethyl-5-isoxazolyl)-methyl phosphonate—dissolved in 50 ml of dimethylformamide—were added dropwise, after gas evolution had ceased the mixture was stirred at 40° C. for another 15 min. At 4° C. 18.6 g of 2-(2,3-epoxypropoxy)-benzaldehyde—dissolved in 40 ml dimethylformamide—were added slowly, then the mixture was stirred at room temperature. After the reaction was completed the liquid was diluted with cold water and extracted with ethylacetate. The organic phase was washed with saturated sodium chloride-solution and dried with magnesium sulfate. After evaporation of the solvent the crude product was purified by chromatography on silica gel affording 19.26 g of the title compound as an oil.

$^1$H-NMR [CDCl$_3$; δ (ppm)]: 2.8 (dd, 1H), 2.9 (dd, 1H), 3.4 (m 4H), 4.1 (dd, 1H), 4.30 (dd, 1H), 4.5 (s, 2H), 6.30 (s, 1H), 6.8–7.1 (m, 3H), 7.3 (m, 1H), 7.5 (m, 1H), 7.7 (d, (1H)

The following compounds were prepared in analogous manner.

IIIa-2 (E)-5-{2-[3-(2,3-Epoxypropoxy)-phenyl]-ethenyl}-3-(methoxymethyl)-isoxazole $^1$H-NMR [CDCl$_3$; δ (ppm)]: 2.8 (dd, 1H), 2.9 (dd,1H), 3.25–3.40 (m, 4H), 3.9 (dd, 1H), 4.3 (dd, 1H), 4.6 (s, 2H), 6.3 (s, 1H), 6.85–7.4 (m, 6H)

IIIa-3 (E)-5-{2-[4-(2,3-Epoxypropoxy)-phenyl]-ethenyl}-3-(methoxymethyl)-isoxazole $^1$H-NMR [CDCl$_3$; δ (ppm)]: 2.75 (dd, 1H), 2.90 (dd, 1H), 3.4–3.5 (m, 4H), 4.0 (dd, 1H), 4.30, (dd,1H), 4.6 (s, 2H), 6.3 (s, 1H), 6.90 (d, 1H), 6.95 (d, 2H), 7.4 (d, 1H), 7.6 (d, 2H).

IIIa-4 (E)-5-{2-[2-(2,3-Epoxypropoxy)-phenyl]-ethenyl}-3-trifluoromethyl-isoxazole $^1$H-NMR [CDCl$_3$; δ (ppm)]: 2.8 (dd, 1 H), 3.0 (dd, 1 H), 3.4–3.5 (m, 1 H), 4.1 (dd, 1 H), 4.3 (dd, 1 H), 6.5 (s, 1 H), 6.9–7.2 (m, 2 H), 7.1(d, 1 H), 7.3–7.4 (m, 1 H), 7.5 (d, 1 H), 7.7 (d, 1 H)

III-a-5 (E)-5-{2-[2-(2,3-Epoxypropoxy)-phenyl]-ethenyl}-3-methoxy-isoxazole $^1$H-NMR [CDCl$_3$; δ (ppm)]: 2.8 (dd, 1 H), 3.0 (dd, 1 H), 3.4–3.5 (m, 1 H), 4.0 (s, 3 H), 4.1 (dd, 1 H), 4.3 (dd, 1 H), 5.9 (s, 1 H), 6.9–7.1 (m, 3 H), 7.3–7.4 (m, 1 H), 7.5 (d, 1 H), 7.6 (d, 1 H)

IIIa-6 (Z)-5-{2-[2-(2,3-Epoxypropoxy)-phenyl]-ethenyl}-3-methoxy-isoxazole $^1$H-NMR [CDCl$_3$; δ (ppm)]: 2.8 (dd, 1 H), 2.9 (dd, 1 H), 3.3–3.4 (m, 1 H), 4.0 (s, 3 H), 4.1 (dd, 1 H), 4.3 (dd, 1 H), 5.6 (s, 1 H), 6.4 (d, 1 H), 6.9–7.1 (m, 2 H), 7.3–7.4 (m, 2 H), 7.4 (d, 1 H), IIIa-7 (E)-3-{2-[2-(2,3-Epoxypropoxy)-phenyl]-ethenyl}-5-methoxymethyl-isoxazole $^1$H-NMR [CDCl$_3$; δ(ppm)]: 2.8 (dd, 1 H), 2.9 (dd, 1 H), 3.4 (s, 3 H), 3.7–3.8 (m, 1 H), 4.0 (dd, 1 H), 4.3 (dd, 1 H), 4.6 (s, 2 H), 6.5 (s, 1 H), 6.9 (d, 1 H), 7.0 (dd, 1 H), 7.2 (d, 1 H), 7.2–7.3 (m, 1 H), 7.5 (d, 1 H), 7.6 (d, 1 H)

IIIa-8 (E)-4-{2-[2-(2,3-Epoxypropoxy)-phenyl]-ethenyl}-2-methoxymethyl-1,3-thiazole $^1$H-NMR [CDCl$_3$; δ (ppm)]: 2.8 (dd, 1 H), 2.9 (dd, 1 H), 3.4–3.5 (m, 1 H), 3.5 (s, 3 H), 3.9–4.1 (m, 1 H), 4.3 (dd, 1 H), 4.8 (s, 2 H), 6.0 (s, 1 H), 6.9 –7.3 (m, 4 H), 7.6 (d, 1H), 7.7 (d, 1 H)

IIIa-9 (E)-2-{2-[2-(2,3-Epoxypropoxy)-phenyl]-ethenyl}-5-(4-methyl-phenyl)-1,3,4-oxadiazole $^1$H-NMR [CDCl$_3$; δ(ppm)]: 2.4 (s, 3 H), 2.8 (dd, 1 H), 3.0 (dd, 1 H), 3.4–3.5 (m, 1 H), 4.1 (dd, 1 H), 4.6 (dd, 1 H), 7.0 (d, 1 H), 7.0 (d, 1 H), 7.2 (d, 1 H), 7.3 (2 H, 7.3 (dd, 1 H), 7.6 (d, 1 H), 7.9 (d, 1 H), 8.0 (d, 2 H)

IIIa-10 (E)-4-{2-[2-(2,3-Epoxypropoxy)-phenyl]-ethenyl}-2-(4-methoxy-phenyl)-1,3-oxazole $^1$H-NMR [CDCl$_3$; δ(ppm)]: 2.8 (dd, 1 H), 3.0 (dd, 1 H), 3.4–3.5 (m, 1 H), 3.9 (s, 3 H), 4.1 (dd, 1 H), 4.3 (dd, 1 H), 6.8–7.0 (m, 4 H), 7.0 (d, 1 H), 7.2 (d, 1 H), 7.6 (d, 1 H), 7.7 (m, 2 H), 7.9 (d, 1 H), 8.0 (d, 1 H)

IIIa-11 (E)-2-{2-[2-(2,3-Epoxypropoxy)-phenyl]-ethenyl}-4-dimethyl-1,3-oxazoline $^1$H-NMR [CDCl$_3$; δ(ppm)]: 1.4 (s, 6 H), 2.8 (dd, 1 H), 3.0 (dd, 1 H), 3.4 (m, 1 H), 4.1 (dd, 1 H), 4.1 (s, 2 H), 4.3 (dd, 1 H), 6.7 (d, 1 H), 6.9 (dd, 1 H), 7.0 (dd, 1 H), 7.3 (dd, 1 H), 7.5 (dd, 1 H), 7.7 (dd, 1 H)

IIIa-12 (E)-5-{2-[2-(2,3-Epoxypropoxy)-4,5-dimethoxyphenyl]-ethenyl}-3-(methoxymethyl)-isoxazole Mp.: 75°–77° C. $^1$H-NMR [CDCl$_3$; δ (ppm)]: 2.8 (dd, 1H), 2.9 (dd, 1H), 3.40 (s, 3H), 3.9 (s, 6H), 4.0 (dd, 1H), 4.4 (dd, 1H), 4.5 (s, 2H), 6.30 (s, 1H), 6.6 (s, 1H), 6.9 (d, 1H), 7.1 (s, 1H), 7.6 (d, 1H).

IIIa-13 (E)-5-{2-[2-(2,3-Epoxypropoxy)-5-N,N-diethylamino-phenyl]-ethenyl}-3-(methoxymethyl)-isoxazole $^1$H-NMR [CDCl$_3$; δ(ppm)]: 1.2 (t, 6H), 2.8 (dd, 1H), 2.9 (dd, 1H), 3.4 (m, 5H), 4.1 (dd, 1H), 4.3 (dd, 1H), 4.6 (s, 2H), 6.15 (d, 1H), 6.2 (s, 1H), 6.8 (d, 1H), 7.35 (d, 1H), 7.55 (d, 1H).

IIIa-14 (E)-5-{2-[2-(2,3-Epoxypropoxy)-6-fluoro-phenyl]-ethenyl}-3-(methoxymethyl)-isoxazole The compound was prepared following the same procedure as described for the synthesis of intermediate IIIa-1. The obtained E/Z-mixture was refluxed in heptane with a catalytic amount of iodine. Then the liquid was diluted with ethyl acetate, washed with Na$_2$S$_2$O$_3$-solution and dried with magnesium sulfate. Filtration through a silica gel column afforded the pure E-isomere.

$^1$H-NMR [CDCl$_3$; δ(ppm)]: 2.70 (dd, 1H), 2.8 (dd, 1H), 3.4 (m, 4H), 4.1 (dd, 1H), 4.35 (dd, 1H), 4.55 (s, 2H), 6.40 (s, 1H), 7.0–7.15 (m, 3H), 7.35 (d, 1H), 7.65 (d, 1H).

IIIa-15 (Z/E)-5-{2-[2-(2,3-Epoxypropoxy)-phenyl]-ethenyl}-3(methoxymethyl)-isoxazole 12 g of 3-(Methoxymethyl-isoxazol-5-yl)-methyl-triphenylphosphonium-bromide and 5.6 g of 2-(2,3-epoxypropoxy)-benzaldehyde were dissolved in 90 ml tetrahydrofuran.. At −10° C. 3.2 g of potassium tert.butylate were added, and the mixture stirred at the same temperature for 15 min. Then the reaction mixture was diluted with cold water, extracted with ethyl acetate, the organic phase washed with saturated sodium chloride-solution and dried with magnesium sulfate. After evaporation of the solvent the crude product was purified by chromatography on silica gel affording 6.4 g of a yellow oil which according to $^1$H-NMR consisted of a mixture of the Z-and the E-isomere. This mixture was used for the further reactions.

IIIa-16 (E)-5-{3-[2-(2,3-Epoxypropoxy)-4-nitro-phenyl]-ethenyl}-3-(methoxymethyl)-isoxazole Mp.: 116°–117.5° C.

$^1$H-NMR [(CDCl$_3$; δ(ppm)]: 2.8 (dd, 1H), 3.0 (dd, 1H), 3.4 (s, 3H), 3.45 (m, 1H), 4.1 (dd, 1H), 4.5 (dd, 1H), 4.55 (s, 2H), 6.4 (s, 1H), 7.0 (d, 1H), 7.15 (d, 1H), 7.6 (d, 1H), 8.1 (dd, 1H), 8.45 (d, 1H).

IIIa-17 (E)-5-{2-[2-(2,3-Epoxypropoxy)-phenyl]-1-methylethenyl}-3-(methoxymethyl)-isoxazole The reaction was carried out analogous to the synthesis of IIIa-1.The obtained E/Z-mixture was separated by chromatography.

$^{13}$C-NMR [(CDCl$_3$; δ(ppm)]: 20.4, 44.6, 50.1, 58.5, 65.9, 69.0, 101.8, 112.9, 115.2, 121.4, 128.2, 129.2, 133.7, 144.5, 155.5, 161.4, 169.1.

IIIa-18 (Z)-5-{2-[2-(2,3-Epoxypropoxy)-phenyl]-1-methylethenyl}-3-(methoxymethyl)-isoxazole $^{13}$C-NMR [(CDCl$_3$; δ(ppm)]: 26.0, 44.5, 50.1, 58.2, 65.7, 65.9, 99.7, 112.5, 114.1, 121.8, 128.1, 129.4, 130.2, 144.2, 154.6, 160.8, 168.9.

IIIa-18 (Z/E)-5-{2-[2-(2,3-Epoxypropoxy)-phenyl]-ethenyl}-2-(methoxymethyl)1,3,4-thiadiazole The compound was prepared following the same procedure as described for the synthesis of intermediate IIIa-1. The obtained E/Z-mixture (ratio 5:1) was separated by cristallisation from diethylether.

Precursor of Type III-b

IIIb-1  2-(2,3-Epoxypropoxy)-4,5-dimethoxy-benzaldehyde 8 g of 4,5-dimethoxy-2-hydroxy-benzaldehyde and 9.1 g of potassium carbonate were dissolved in 150 ml dimethylformamide, and then 7.2 g of epibromohydrine were slowly added thereto. The mixture was heated with stirring at 50° C. During addition of water at room temperature a yellow precipitate occured, which was filtered off, washed with water and dried in order to obtain 8.8 g of the pure compound.

Mp.: 121°–123° C.

$^1$H-NMR [CDCl$_3$; δ (ppm)]: 2.8 (dd, 1H), 2.95 (dd, 1H), 3.35 (m 1H), 3.9 (s, 3H) 4.0 (s, 3H), 4.05 (dd, 1H), 4.45 (dd, 1H), 6.55 (s, 1H), 7.30 (s, 1H), 10.4 (s, 1H).

The following compounds were prepared in an analogous manner.

IIIb-2  5-N,N-Diethylamino-2-(2,3-epoxypropoxy)-benzaldehyde $^1$H-NMR [CDCl$_3$; δ(ppm)]: 1.2 (t, 6H), 2.8 (dd, 1H), 3.0 (dd, 1H), 3.4 (m, 5H), 4.1 (dd, 1H), 4.35 (dd, 1H), 6.1 (d, 1H), 6.35 (dd, 1H), 7.75 (d, 1H), 10.2 (s, 1H).

IIIb-3  2-(2,3-Epoxypropoxy)-3-fluoro-benzaldehyde $^1$H-NMR [CDCl$_3$; δ (ppm)]: 2.75 (dd, 1H), 2.95 (dd, 1H), 3.38 (m, 1H), 4.18 (dd, 1H), 4.55 (dd, 1H), 7.08–7.40 (m, 2H), 7.65 (m 1H), 10.45 (s, 1H).

IIIb-4  2-(2,3-Epoxypropoxy)-4-nitro-benzaldehyde

In 150 ml dimethylformamide were dissolved 15 g of 2-hydroxy-5-nitro-benzaldehyde, and 9.87 g of potassium tert.butylate were added. With stirring, 13.2 g of epibromohydrin were added dropwise, and then the mixture was stirred at 50° C. After the reaction was completed the solvent was evaporated and the obtained residue chromatographed on silica gel, which afforded 5 g of pure product.

$^1$H-NMR [CDCl$_3$; δ (ppm)]: 2.85 (dd, 2H), 3.05 (dd,2H), 3.5 (m, 1H), 4.15 (dd, 2H), 4.6 (dd, 2H), 7.2 (d, 1H), 8.45 (dd, 1H), 8.7 (d, 1H), 10.5 (s, 1H)

Phosphonates IIIc

Preparation of diethyl (3-methoxy-isoxazol-5-yl)-methyl phosphonate (IIIc-2)

3.8 g 5-chloromethyl-3-methoxy-isoxazole and 6.0 g of triethylphosphite were stirred at 150° C. until complete conversion of the chloromethyl isoxazole (2–8 h). Kugelrohr destillation gave 3.6 g of diethyl (3-methoxy-isoxazol-5-yl)-methane phosphonate. Bp. 160°–165° C./0.3 mm Hg.

$^1$H-NMR CDCl$_3$; δ(ppm)]: 1.3 (t, 6 H), 3.2 (d, 2 H), 3.9 (s, 3 H), 4.2 (dq, 4 H), 5.9 (d, 1 H)

The following compounds were prepared using the same procedure:

IIIc-1  Diethyl (3-trifluoromethyl-isoxazol-5-yl)-methyl phosphonate $^1$H-NMR [CDCl$_3$; δ(ppm)]: 1.3 (t, 6 H), 3.4 (d, 2 H), 4.1 (dq, 4 H), 6.5 (d, 1 H)

IIIc-3  Diethyl (5-methoxymethyl-isoxazol-3-yl)-methyl phosphonate
Bp=145° C./0.4 mm Hg IIIc-4  Diethyl (2-methoxymethyl-1,3-thiazol-4-yl)-methyl phosphonate
Bp=150° C./0.1 mm Hg IIIc-5  Diethyl [5-(4-methyl-phenyl)-1,3,4-oxadiazol-2-yl]-methyl phosphonate $^1$H-NMR [CDCl$_3$, δ(ppm)]: 1.3 (t, 6 H), 2.4 (s, 3 H), 3.5 (d, 2 H), 4.1 (dq, 4 H), 7.3 (d, 2 H), 7.9 (d, 2 H)

IIIc-6  Diethyl 2-(4-methoxy-phenyl)-1,3-oxazol-4-yl]-methyl phosphonate $^1$H-NMR [CDCl$_3$; δ(ppm)]: 1.3 (t, 6 H). 3.1 (d, 2 H), 3.8 (s, 3 H), 4.0–4.2 (m, 4 H), 6.9–7.0 (m, 2 H), 7.6 (d, 2 H), 7.9–8.0 (m, 2 H).

IIIc-7  Diethyl (2-methoxymethyl-1,3,4-thiadiazol-5-yl)-methyl phosphonate $^1$H-NMR (CDCl$_3$; δ (ppm)]: 1.35 (t, 6H), 3.5 (s, 3H), 3.7 (d, 2H), 4.15 (q, 4H), 4.85 (s, 2H).

IIIc'  3-(Methoxymethyl-isoxazol-5-yl)-methyl-triphenylphosphonium-bromide

In 150 ml toluene/acetone 2:1 were dissolved 30 g of 5-bromomethyl-3-(methoxy-methyl)-isoxazole and 30.5 g of triphenylphosphine. The mixture was refluxed and, after the reaction was completed, the precipitate was filtered off, dried and recristallized from acetone/diethylether affording 48.8 g of the title compound.

Mp: >200° C.

$^1$H-NMR [CDCl$_3$; δ (ppm)]: 2.3 (s, 3H), 4.4 (s, 2H), 5.95 (d, 2H), 6.8 (d, 1H), 7.6–7.9 (m, 15H).

Precursor of Type V

Va-1  5-{[2-(2,3-Epoxypropoxy)-phenoxy]-methoxymethyl}-3-(methoxymethyl)-isoxazole 0.73 g of sodium hydride (60% in mineral oil) were washed with pentane to remove the mineral oil and 30 ml of dry dimethylformamide added. 3.8 g of 3-(methoxymethyl)-5-{2-[2-(hydroxy)-phenoxy}-methoymethyl}-isoxazole—dissolved in 30 ml of dimethylformamide—were added slowly and, after gas evolution had ceased, the mixture was stirred for another 15 min. at 40° C. At room temperature 2.0 ml of epibromohydrine were added dropwise, maintaining a temperature of about 40° C., afterwards the mixture was stirred at 40° C. After the reaction was finished the mixture was diluted with ice water, extracted with ethylacetate, the organic phase washed with sodium chloride solution and dried with magnesium sulfate. Evaporation of the solvent and purification by chromatography on silica gel afforded 3.1 g of the pure compound as oil.

$^1$H-NMR [CDCl$_3$; δ (ppm)]: 2.65 (dd, 1H), 2.83 (dd, 1H), 3.20 (m, 1H), 3.38 (s, 3H), 3.50 (dd, 1H), 3.80 (dd, 1H), 4.53 (s, 2H), 4.65 (d, 1H), 5.18 (s, 2H), 6.40 (s, 1H), 6.92 (d, 1H), 7.05 (m, 1H), 7.28 (m, 1H), 7.43 (m, 1H).

Vb-I  3-(Methoxymethyl)-5-{2-[2-(hydroxy)-methoxymethyl]}-isoxazole a) 2.9 g of sodium hydride (60% in mineral oil) were washed with pentane to remove the mineral oil and 100 ml of dry dimethylformamide added. 15 g of 2-(tert.-butyldimethylsilyloxy)-benzylalcohol—dissolved in 40 ml of dimethylformamide—were added slowly through a dropping funnel and after gas evolution had ceased the mixture was stirred for another 15 min. at 40° C. After cooling to 10° C. 5-(chloromethyl)-3-(methoxymethyl)isoxazole —dissolved in 40 ml dimethylformamide—was added dropwise, maintaining a reaction temperature of about 10° C., then the mixture was stirred at room temperature. After the reaction was completed the mixture was diluted with cold water and extracted with ethylacetate. The organic phase was washed with saturated sodium chloride solution and then dried over magnesium sulfate. After evaporation of the solvent the crude .product was purified by chromatography on silica gel, which afforded 10.6 g of the pure compound.

b) In 90 ml tetrahydrofuran were dissolved 10.6 g of the above mentioned silylether, and 58.3 ml tetrabutylammoniumfluoride (1 m solution in tetrahydrofuran) were added slowly at 4° C. The mixture was stirred for 15 min. at 4° C. and then allowed to warm up to room temperature. After 1 h the mixture was diluted with cold water and extracted with methyl-tert.butylether. Then the organic phase was washed with sature sodium chloride solution and dried with magnesium sulfate. After evaporation of the solvent the obtained oily residue was purified by chromatography on silica gel, which afforded 4.5 g of the title compound as a yellow oil.

$^1$H-NMR [CDCl$_3$; δ (ppm)]: 2.30 (s, 1H), 3.38 (s, 3H), 4.53 (s, 2H), 4.72 (s, 2H), 5.24 (s, 2H), 6.42 (s, 1H), 6.93 (d, 1H), 7.03 (m, 1H), 7.25–7.40 (m, 2H).

Precursor of Type VI

VIb-1 [2-(2-tert. Butyldimethylsiloxy-phenyl)-ethyl]-4,5-dimethyl-oxazòle (VIb)

To a solution of 5 g freshly destilled diisopropylamine in 90 ml tetrahydrofuran was added 33 ml of a 1.5in solution of n-butyllithium in hexane at 0° C. After stirring for 30 min the solution was cooled to −78° C. 5 g of 2,4,5-trimethyloxazole, dissolved in tetrahydrofuran, were added to the lithiumdiisopropylamide solution, after 20 min. 15.06 g of 2-bromomethyl-phenyl-tert.butyldimethylsilyl ether were added. The reaction mixture was allowed to warm up to room temperature and was then poured into a saturated ammonium chloride solution. After extraction with diethyl ether, drying of the ether layer over sodium sulfate and evaporation of the solvent the residue was purified by chromatography on silica gel with heptane/ethyl acetate (5:1) to give 4.6 g product.

$^1$H-NMR [CDCl$_3$; δ(ppm)]: 0.3 (s, 6 H), 1.0 (s, 9 H), 2.1 (s, 3 H), 2.2 (s, 3 H), 2.9–3.1 (m, 2 H), 6.7–6.9 (m, 2 H), 7.0–7.2 (m, 2 H)

Precursor of Type VIII

VIIIa-1 5-[{2-(2,3-Epoxypropoxy)-phenyl}-carbonyl]-3-(methoxymethyl)-isoxazole

The reaction was carried out according to the preparation of of epoxy compounds type IIIa using 5-{[2-hydroxy)-phenyl]-carbonyl}-3-(methoxymethyl)-isoxazole (precursor VIIIb-1).

$^1$H-NMR (CDCl$_3$: δ (ppm)]: 2.6 (m, 1H), 2.8 (m 1H), 3.05 (m, 2H), 3.25 (s, 3H), 4.05 (dd, 1H), 4.25 (dd, 1H), 4.6 (s, 2H), 6.95 (s, 1H), 7.0–7.2 (m, 2H), 7.5–7.6 (m, 2H).

VIIIb-1 5-[{2-(Hydroxy)-phenyl}-carbonyl]-3-(methoxymethyl)-isoxazole a) 5-[2-(Methoxymethyl)-phenoxy}-carbonyl]-3-(methoxymethyl)-isoxazole 22.8 g of methoxymethyl-phenol and 23 ml of N,N,N',N'-tetraethylenediamine were dissolved in 150 ml of tetrahydrofuran. At −78° C. 100 ml of n-butyllithium (15% solution in n-hexane) were added slowly, then the reaction was stirred for 30 min. at the same temperature. Afterwards this mixture was added to a precooled (−78° C.) solution of 27.4 g 3-(methoxymethyl)-5-(carboxymethyl)-isoxazole in a mixture of 100 ml of tetrahydrofuran and 75 ml of 1,3-dimethyl-tetrahydro-2[1H]-pyrimidinon. The mixture was stirred for another 3 h at this temperature, then allowed to warm up to −20° C. and diluted with an acidic buffer solution (citric acid/sodium hydroxide; pH 5–6). After extraction with dichloromethane the organic phase was washed with saturated sodium chloride-solution, dried over magnesium sulfate and the solvent was evaporated. Purification by chromatography on silica gel afforded 5.6 g of the product as an oil.

b) 5-[{2-(Hydroxy)-phenyl}-carbonyl]-3-(methoxymethyl)-isoxazole

To a solution of 5.3 g of 5-[2-(methoxymethyl)-phenoxy}-carbonyl]-3-(methoxy-methyl)-isoxazole in 40 ml of tetrahydrofuran 16 ml of a 2 m hydrochloric acid-solution were added at room temperature, the reaction mixture was then refluxed for 3 h. After the reaction was completed the liquid was extracted with ethylacetate, washed with saturated sodium chloride-solution and dried over magnesium sulfate. Evaporation of the solvent afforded 4.8 g of the pure compound.

$^1$H-NMR (CDCl$_3$; δ (ppm)]: 3.45 (s, 3H), 4.6 (s, 2H), 6.9 (s, 1H), 7.15 (m, 1H), 7.25 (m, 1H), 7.5 (m, 2H).

VIIIa-2 2-[(2,3-Epoxypropoxy)-4,5-dimethoxy]-3-phenylpropanone 8.4 g of sodium hydride (60% in mineral oil) were washed with pentane to remove the mineral oil, then 50 g of 1-(2-hydroxy-4,5-dimethoxy)-3-phenyl-propanone—dissolved in 400 ml of dry dimethylformamide—were added dropwise and after gas evolution had ceased the mixture was stirred for another 15 min. Then 35.8 g of epibromohydrine were added slowly and the mixture was stirred at 50° C. After the reaction was completed the mixture was diluted with ice water and extracted with ethylacetate. The organic phase was washed with saturated sodium chloride-solution and then dried with magnesium sulfate. Evaporation of the solvent and treatment of the residue with diethylether afforded 48.8 g of the pure product.

Mp.: 120°–121° C. $^1$H-NMR [CDCl$_3$; δ (ppm)]: 2.75 (dd, 1H), 2.9 (dd, 1H), 3.1 (t, 1H), 3.3–3.4 (m, 3H), 3.9 (s, 3H), 3.95 (s, 3H), 4.0 (m, 1H), 4.4 (dd, 1H), 6.55 (s, 1H), 7.15–7.35 (m, 5H), 7.4 (s, 1H).

VIIIb-2 1-(2-Hydroxy-4,5-dimethoxy)-3-phenyl-propanone a) [1-(3,4-Dimethoxy)-phenyl]-3-phenyl-propionat To 48 g of 3,4-dimethoxy-phenol in 700 ml of tetrahydrofuran were added 44 ml of triethylamine and a spatula of 4,4-dimethylaminopyridine. At 0° C. 52.5 g of 3-phenylpropionylchloride—dissolved in 100 ml of tetrahydrofuran—were added dropwise, then the mixture was stirred at room temperature. After the reaction was completed the precipitate was filtered off, the filtrate diluted with water and extracted several times with ethylacetate. The combined organic phases were washed with saturated sodium bicarbonate and sodium chloride solution and dried over magnesium sulfate. After evaporation of the solvent 87.6 g of the pure ester were obtained.

$^1$H-NMR [CDCl$_3$, δ (ppm)]: 2.9 (t, 2H), 3.1 (t, 2H), 3.8 (s, 3H), 3.85 (s, 3H), 6.5–6.6 (m, 2H), 6.8 (d, 1H), 7.15–7.4 (m, 5H).

b) 1-(2-Hydroxy-4,5-dimethoxy)-3-phenyl-propanone

At 0° C. 56.3 g of titanium tetrachloride were added slowly to a solution of 85 g of [1-(3,4-dimethoxy)-phenyl]-3-phenyl-propionat in 500 ml of dry nitromethane, the reaction mixture was then stirred for about 5 h at room temperature. Afterwards the liquid was diluted with ice water, extracted several times with ethylacetate and the combined organic phases were washed with saturated sodium chloride solution and then dried over magnesium sulfate. After evaporation of the solvent the crude product obtained was purified by chromatography on silica gel. Crystallization from isopropanole afforded 3.4 g of the pure product.

Mp.: 81°–82° C. $^1$H-NMR [CDCl$_3$; δ (ppm)]: 3.1 (m, 1H), 3.2 (m 1H), 3.85 (s, 3H), 3.9 (s, 3H), 6.4 (s, 1H), 7.0 (s, 1H), 7.1–7.2 (m, 5H), 12.85 (s, 1H).

Precursor of Type IX

IXa-1 N-(5-Methyl-isoxazol-3-yl)-2-(2,3-epoxy-propoxy)-benzamide

The reaction was carried out according to the preparation of epoxy compounds type IIIa using N-(5-methyl-isoxazol-3-yl)-2-hydroxy-benzamide (precursor IXb-1) and sodium hydride as base.

$^1$H-NMR [CDCl$_3$; δ(ppm)]: 2.4 (s, 3 H), 2.9 (dd, 1 H), 3.0 (dd, 1 H), 3.5–3.6 (m, 1 H), 4.2 (dd, 1 H), 4.5 (dd, 1 H), 6.8 (s, 1 H), 7.0(d, 1 H), 7.1 (dd, 1 H), 7.5 (dd, 1 H), 8.2 (d, 1 H), 10.3 (s, 1 H)

IXb-1 N-(5-Methyl-isoxazol-3-yl)-2-hydroxy-benzamide

To a solution of 1 g 2-acetoxy-N-(5-methyl-isoxazol-3-yl)-benzamide, in 20 ml of methanol was added 0.58 g potassium carbonate. After stirring overnight the mixture was poured into saturated ammonium chloride solution, and extracted with ethyl acetate. The organic layer was dried over sodium sulfate. Evaporation of the solvent gave 0.63 g amide.

$^1$H-NMR [CDCl$_3$; δ(ppm)]: 2.5 (s, 3 H), 6.9 (s, 1 H), 7.0 (d, 1 H), 7.0 (dd, 1 H), 7.5 (dd, 1 H), 7.8 (d, 1 H), 10.2 (s, 1 H), 11.5 (br s, 1 H)

IXc-1 N-(5-Methyl-isoxazol-3-yl)-2-acetoxy-benzamide

To a solution 4.57 g 3-amino-5-methyl-isoxazole and 4.7 g triethylamine in tetrahydrofuran 10 g 2-acetoxy-benzoyl chloride were added dropwise at 0° C. and the reaction mixture was stirred at room temperature for 3 h. The mixture was given on saturated ammonium chloride solution and extracted with ethyl acetate. The organic phase was dried over magnesium sulfate. After concentration the residue was purified by flash chromatography on silica gel with heptane/ethyl acetate giving 7.12 g amide.

$^1$H-NMR [CDCl$_3$; δ(ppm)]: 2.3 (s, 3 H), 2.4 (s, 3 H), 6.8 (s, 1 H), 7.2 (d, 1 H), 7.3 (dd, 1 H), 7.5 (dd, 1 H), 7.9 (d, 1 H), 9.7 (s, 1 H)

IXa-2 5-{2-N-[2-(2,3-Epoxypropoxy)-phenyl]-aminocarbonyl}-3-(methoxymethyl)-isoxazole The reaction was carried out according to the preparation of epoxy compounds type IIIa using 5-{2-N-[2-(hydroxy)-phenyl]-aminocarbonyl}-3-(methoxymethyl)-isoxazole (precursor IXb-2) and sodium hydride as base.

$^1$H-NMR [(CDCl$_3$; δ (ppm)]: 2.85 (dd, 1H), 2.95 (dd, 1H), 3.47 (s, 4H), 4.14 (dd, 1H), 4.40 (dd, 1H), 4.63 (s, 2H), 6.95–7.18 (m, 4H), 8.45 (dd, 1H), 8.95 (s, 1H).

IXb-2 5-{2-N-[2-(Hydroxy)-phenyl]-aminocarbonyl}-3-(methoxymethyl)-isoxazole

The reaction was carried out according to the preparation of precursor IXb-1 using 2-amino-phenol and (3-methoxymethyl)-isoxazol-5yl-carbonylchloride.

$^{13}$C-NMR [(CDCl$_3$; δ (ppm)]: 58.7, 65.5, 106.8, 115.9, 120.1, 121.0, 125.4, 125.7, 147.0, 162.6, 163.8

IXa-3 5-{2-N-[2-(2,3,-Epoxypropoxy)-phenyl]-2-N-methyl-aminocarbonyl}-3-methoxymethyl)-isoxazole The reaction was carried out according to the preparation of epoxy compounds type IIIa using 5-{2-N-[2-hydroxy)-phenyl]-2-N-methyl-aminocarbonyl}-3-(methoxymethyl)-isoxazole (precursor IXb-3) and sodium hydride as base.

IXb-3 5-{2-N-[2-Hydroxy)-phenyl]-2-N-methyl-aminocarbonyl}-3-(methoxymethyl)-isoxazole The reaction was carried out according to the synthesis of precursor IXc-1 using 2-(N-methyl)-aminophenol and (3-methoxymethyl)-isoxazol-5-yl-carbonylchloride.

$^1$H-NMR (CDCl$_3$; δ (ppm)]: 3.25 (s, 3H), 3.4 (s, 3H), 4.35 (s, 2H), 5.85 (s, 1H), 6.9 (m, 1H), 7.05 (m, 1H), 7.1 (m, 1H), 7.25 (m, 1H), 7.7–7.9 (broad, 1H).

Various Types of Precursors:

ZH

Amino compounds of type ZH are either commercially available (e.g.: 1-diphenyl-methyl-piperazine) or can be easily prepared according to known procedures by those skilled in art (e.g.: mono-N-acyl-piperazines by debenzylation of 1-acyl-4-benzyl-piperazines as described in Th. Greene "Protective Groups in Organic Synthesis" Wiley & Sons, 1981, page 272; mono-alkyl-piperazines according to Organc Synthesis Coll. Vol.5, 1973, page 88).

Compounds of the formula H-Z-3 can be prepared from amines of the formula:

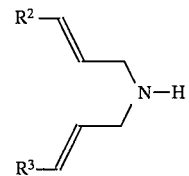

by subjecting them photochemically to a 2+2-cycloaddition. This reaction can be performed in a solvent such as aacetone at a temperature between 20° C. and 80° C. A mercury high pressure lamp is particularly suitable as light source. It may be advantageous to carry out the photo cycloaddition under nitrogen in a quartz apparatus, possibly with the addition of about 1 mole of hydrochloric acid per mole of amine (see DE 42 19 975).

IIId-1 Diethyl 2-(2,3-epoxypropoxy)-benzyl phosphonate

To a solution of 0.2 mol sodium hydride in 100 ml absolute dimethylformamide under inert gas a solution of 0.2 mol of diethyl 2-hydroxy-benzyl phosphonate in 200 ml absolute dimethylformamide was added dropwise at room temperature. The mixture was warmed to 50° C. for 30 min, then cooled to room temperature, At this temperature 0.35 mole of epibromohydrine were added dropwise. The reaction mixture was stirred at 50° C. for 30 min. The reaction was quenched by dropwise addition of 200 ml water to the reaction mixture under permanent cooling with ice. The reaction mixture was then poured into 3l water and extracted five times with dichloromethane. The organic phase was washed with water, dried over sodium sulfate, filtered and the solvent evaporated under reduced pressure. The remaining residue was chromatographed over silica gel. The product was isolated as viscous oil (28.0 g).

$^1$H-NMR [CDCl$_3$; δ (ppm)]: 1.25 (t,6H), 2.8 (t, 1H), 2.9 (t, 1H), 3.2 (d,2H), 3.4 (m,1H) 4.0 (dxd,1H), 4.1 (q,4H), 4.3 (dxd,1H), 6.8–7.2 (4H)

IIIh-1 Diethyl 2-{3-[4-(cyclohexyl-phenyl-methyl]-piperazin-1-yl]-2-hydroxy-propoxy}-benzyl phosphonate A mixture of 30 mmol diethyl 2-(oxiran-2-yl methoxy)-benzyl phosphonate and 30 mmol 1-cyclohexyl-phenyl-methyl-piperazin in 150 ml ethanol was heated under reflux for 5 h. The solvent was evaporated under reduced pressure. The remaining residue was chromatographed over silica gel. The product was isolated as an viscous oil (14.3 g).

$^{13}$C-NMR [DMSO; δ (ppm)] (citrate) : 15.1, 16.1, 25.5, 25.6, 26.3 29.6, 30.4, 36.3, 43.6, 52.8, 58.9, 61.3, 64.4, 70.1, 71.6, 73.3, 111.5, 120.1, 120.4, 126.9, 127.7, 128.1, 129.0 131.1, 136.2, 155.9, 171.2, 176.0

Precursors for Phosphonates IIIc

Precursor for diethyl (3-trifluoromethyl-isoxazol-5-yl)-methyl phosphonate (IIIc-1)

5-Chloromethyl-3-trifluoromethyl-isoxazole

To a solution of 36.2 g of 1-bromo-2-trifluoro-ethanal oxime in dimethylformamide were added 140 ml of a 70% solution of propargyl chloride in toluene. 59.8 g sodium carbonate was added in small portions over a period of 6 h. The suspension was stirred overnight and then filtrated. The filtrate was poured into water. After extraction with dichloromethane the combined organic phases were dried over sodium sulfate. Evaporation of the solvent gave 18.7 g of an oily residue which contained 69% product and 31% toluene due to gas chromatography analysis.

$^1$H-NMR [CDCl$_3$; δ (ppm)]: 4.7 (s, 2 H), 6.5 (s, 1 H)

Precursor for Diethyl (3-Methoxy-isoxazole-5-yl)-methyl phosphate (IIIc-2)

a) 5-Chloromethyl-3-methoxy-isoxazole

A mixture of 1.0 g 5-hydroxymethyl-3-methoxy-isoxazole and 10 g thionyl chloride was stirred at room temperature for 20 h. The excess thionylchloride was removed in vacuo, dissolved in toluene and the solvent evaporated. 1.0 g of an oil was obtained.

$^1$H-NMR [CDCl$_3$; δ(ppm)]: 4.0 (s,31 H), 4.5 (s, 2 H), 6.0 (s, 1 H)

b) 5-Hydroxymethyl-3-methoxy-isoxazole

To a solution of 7.0 g 3-methoxy-5-carbethoxy-isoxazole in 80 ml tetrahydrofuran a 2m solution of lithiumborohydride in tetrahydrofuran was added at 15°–20° C. The reaction mixture was stirred for 2 h at room temperature, then poured into saturated ammoniumchloride solution and extracted with dichloromethane. The organic phase was dried over magnesium sulfate and evaporated togive 4.87 g alcohol.

$^1$H-NMR [250 MHz; CDCl$_3$; δ(ppm)]: 4.0 (s,3 H), 4.6 (s, 2 H), 5.9 (s, 1 H)

Precursor for Diethyl (5-Methoxymethyl-isoxazol-3-yl)-methyl phosphonate (IIIc-3)

a) 3-Chloromethyl-5-methoxymethyl-isoxazole 8.2 g of 3-hydroxymethyl-5-methoxymethyl-isoxazole were added to 34 g thionyl chloride at 0° C. The resulting mixture was stirred overnight. Excess thionylchloride was removed in vacuo. The residue was dissolved in toluene and then the solution was evaporated again. This procedure was repeated three times to give 8.2 g of crude chloromethyl-isoxazole.

$^1$H-NMR [CDCl$_3$; δ(ppm)]: 3.4 (s, 3 H), 4.5 (s, 2 H), 4.5 (s, 2 H), 6.4 (s, 1 H)

b) 3-Hydroxymethyl-5-methoxymethyl-isoxazole

To a solution of 6.55 g of 3-carbonylethoxy-5-methoxymethyl-isoxazole in 70 ml dry tetrahydrofuran were added 77.6 ml of a 1 N solution of L-selectride® at 0° C. The solution was stirred overnight at room temperature. After cooling to 0° C. 13 ml of water and 33 ml of ethanol were added, then simultaneously 33 ml of a 6 N solution of sodium hydroxide and 49 ml hydrogen peroxide were added with caution. After stirring for half an hour the supernatant was decanted, the residue washed several times with methylene chloride. The aqueous phase was extracted with dichloromethane in an extraction apparatus for one day. The organic phase was dried over sodium sulfate and the solvent evaporated to give 4.1 g product.

$^1$H-NMR [CDCl$_3$; δ(ppm)]: 3.3 (s, 1 H), 3.4 (s, 3 H), 4.6 (s, 2 H), 4.8 (s, 2 H), 6.3 (s, 1H)

c) 3-Carbonylethoxy-5-methoxymethyl-isoxazole

A solution of 10.1 g of dry triethylamine in 180 ml diethyl ether was given dropwise to a stirred solution of 15.15 g of ethyl chlorooximinoacetate and 17.52 g propargyl methyl ether in 360 ml ether over a period of 5 h at room temperature. After stirring overnight the suspension was diluted with 500 ml diethyl ether and then filtered. The filtrate was washed twice with water, dried over sodium sulfate and concentrated to give 14.8 g product.

$^1$H-NMR [CDCl$_3$; δ(ppm)]: 1.4 (t, 3H), 3.5 (s, 3 H), 4.5 (q, 2 H), 4.6 (s, 2 H), 6.7 (s, 1 H)

Precursor for Diethyl (2-Methoxymethyl-1,3-thiazol-4-yl)-methyl phosphonate (IIIc-4)

a) 4-Chloromethyl-2-methoxymethyl-1,3-thiazole

A solution of 9 g of 2-methoxy-thioacetamide and 10.87 g 1,3-dichloroacetone in 90 ml ethanol was refluxed for 2 h. The solvent was evaporated and the residue neutralized with saturated sodium bicarbonate solution. After extraction with ether the organic phase was washed twice with water and dried over sodium sulfate. Evaporation of the solvent left 13.0 g crude product.

$^1$H-NMR [CDCl$_3$; δ(ppm)]: 3.5 (s, 3H), 4.7 (s, 2H), 4.8 (s, 2H), 7.3 (s, 1 H)

b) 2-Methoxy-thioacetamide 18 g of hydrogen sulfide was bubbled into a solution of 30 g. of 2-methoxy-acetonitrile and 34.1 g of triethylamine in 200 ml dry dimethylformamide during 30 min at a temperature betwen 55° and 60° C. After stirring overnight nitrogen was passed through the dark mixture. The solvent was removed in vacuo, the residue diluted with ether and the organic phase was washed three times with water. After drying over sodium sulfate and evaporation of the organic solvent the residue was destilled to give 17.9 g product.

Bp=90°–94° C./0.2 mm Hg

Precursor for Diethyl [2-(4-methoxyphenyl)-1,3-oxazol-4-yl]-methyl phosphonate (IIIc-5)

a) N-Chloroacetyl-N'-(4-methylbenzoyl)-hydrazide 56.5 g of Chloroacetylchloride were added to a solution of 75.0 g of 4-toluic hydrazide and 50.5 g of triethylamine in 1l dimethylformamide at 0° C. After stirring for 1.5 h at room temperature the mixture was given into ice water. The precipitate was filtered and washed with water and ethyl acetate. After drying at 30° C. 71.3 g of solid hydrazide were obtained.

Mp=174°–178° C.

b) 4-Chloromethyl-2-(4-methoxyphenyl)-1,3-oxazole 70 g of N-chloroacetyl-N'-(4-methylbenzoyl)-hydrazide and 100 ml of were stirred for 10 h under reflux. Afterwards the excess of phosphoroxychloride was evaporated in vacuo, the obtained residue diluted with water and extracted with methyltert. butylether. The organic phase was dried with sodium sulfate, evaporation of the solvent left 36 g of 4-chloromethyl-2-(4-methoxyphenyl)-1,3-oxazole.

Mp=114°–116° C.

Precursor for Diethyl [2-(4-methoxyphenyl)-1,3-oxazol-4-yl]-methyl phosphonate (IIIc-6)

4-Chloromethyl-2-(4-methoxy -phenyl)-oxazole 25 g of 4-methoxy-benzamide and 21 g of 1,3-dichloro-acetone were heated to 140° C. under nitrogen for 3 h. After cooling dichloromethane was added and the suspension was filtered. Chromatography on silica gel with heptane/ethyl acetate (1:2) gave 22.5 g oxazole.

$^1$H-NMR [CDCl$_3$; δ(ppm)]: 3.9 (s, 3 H), 4.6 (s, 2 H), 6.9–7.0 (m, 2 H), 7.6 (s, 2H), 7.9–8.0 (m, 2 H).

Precursor for Diethyl (2-methoxymethyl-1,3,4-thiadiazol-5-yl)-methyl phosphonate (IIIc-7)

a) N-(2-Chloroacetyl)-N'-(2-methoxyacetyl)-hydrazide 104 g of N-(2-methoxyacetyl)-hydrazide and 101 g of triethylamine were dissolved in 1200 ml of dichloromethane. At 15° C. 113 g of 2-chloroacetylchloride were added dropwise. After the reaction was completed the precipitate was filtered off, the filtrate diluted with water and and then extracted continuously with ethylacetate using a perforator. Cristallization of the obtained crude product from ethylacetate afforded 121 g of the product as a white solid.

Mp.: 97°–100° C.

b) 5-Chloromethyl-2-methoxymethyl-1,3,4-thiadiazole 100 g of N-(2-chloroacetyl)-N'-(2-methoxyacetyl)-hydrazide were dissolved in 1200 ml of 1,4-dioxane, 61.5 g of phosphoropentasulfide and 60 g of potassium bicarbonate were added subsequently and this mixture was refluxed until the reaction was completed. After evaporation of the solvent the obtained brown-red residue was dissolved in ethylacetate, washed with saturated sodium bicarbonate- and sodium chloride-solution and dried with magnesium sulfate. After evaporation of the solvent the residue was destilled in vacuo to yield 23 g of the product as yellow oil.

Bp.: 155°–160° C./0.8mm Hg $^1$H-NMR (CDCl$_3$: δ (ppm)]: 3.5 (s, 3H), 4.9 (s, 2H), 4.95 (s, 2H).

VIIc a) 2-(3-Methyl-isoxazol-5-yl)-1-(2-tert.butyldimethylsiloxy-phenyl)-ethanone 52 ml of 1N solution of n-butyllithium in hexane were added to a solution of 6 g of 3,5-dimethylisoxazol in 200 ml of tetrahydrofuran at −78° C. After stirring for 1 h 15 g of methyl 2-tert.butyldimethylsiloxybenzoate in 50 ml of tetrahydrofuran were added at the same temperature. The reaction mixture was slowly warmed up to −20° C. A saturated aqueous solution of ammonium chloride was added, the mixture was extracted several times with ethylacetate. The organic phase was separated, washed with water and dried over magnesium sulfate. Chromatography on silica gel with heptane/ethylacetate gave 9.4 g of the product.

$^1$H-NMR (CDCl$_3$; δ (ppm)]: 0.3 (s, 9H), 1.0 (s, 3H), 2.3 (s, 3H), 4.4 (s, 2H), 6.1 (s, 1H), 6.9 (d, 1H), 7.0 (dd, 1H), 7.4 (dd, 1H), 7.6 (d, 1H).

b) 2-(3-Methyl-isoxazol-5-yl-ethinyl)-phenyl-tert.butyldimethylsilyl-ether 14.6 g of triethylamine were added to a suspension of 6 g of 2-(3-methyl-isoxazol-5-yl)-1-(2-tert.butyldimethylsiloxy-phenyl)-ethanone and 5.8 g 2-chloro-3-ethylbenzoxazolium tetrafluoroborate in 150 ml of dichloromethane at 0° C. After stirring at room temperature overnight the reaction mixture was poured into water and extracted with ethylacetate. The organic phase was separated and dried over magnesium sulfate. After filtration and evaporation the residue was chromatographed on silica gel to afford 1.2 g of the 2-(3-methyl-isoxazol-5-yl-ethinyl)-phenyl-tert.butyldimethylsilyl-ether.

$^1$H-NMR (CDCl$_3$; δ (ppm)]: 0.3 (s, 9H), 1.0 (s, 6H), 2.3 (s, 3H), 6.3 (s, 1H), 6.9 (d, 1H), 7.0 (dd, 1H), 7.3 (dd, 1H), 7.5 (d, 1H).

The compounds of the present invention may be used to treat tumors by administration of the compound to the mammal in combination with usual chemotherapy. Usual chemotherapy means treatment with chemotherapeutic agents such as:

a) antibiotics such as actinomycine D, doxorubicine (adriamycine), daunorubicine, mithramycine, bleomycine or other intercalating agents, b) alkaloids such as vincristine, vinblastine, vindevinblastine, vindesine, etoposide and tenoposide, c) alkylating agents such as cyclophosphamide, nitrosoureas, cisplatin d) antimetabolites such as methotrexate, 5-fluorouracile and analogues, 6-mercaptopurine, 6-thioguanine and cytarabine, and combinations of thereof.

DESCRIPTION OF BIOLOGICAL MODES

In Vivo Tumor Models

Murine Tumor model

The tumor line M109H2 is a subline of the murine Madison lung carcinoma M109 selected for resistance to Adriamycin (ADR). M109 is of spontaneous origin in BALB/c mice. The M109H2 subline grows as a monolayer in 90% RPMI-1640 and 10% fetal bovine serum.

On day 0, mice are inoculated subcutaneously with 1×10$^6$ cells. The mice used are 4–6 weeks old athymic female nude mice obtained from Taconic or Charles River Laboratories. On day 7, the tumor bearing mice are randomized into groups of 5. In the M109H2 model, for each experiment there is a negative control group (receiving ADR only) and a positive control group (receiving a known modulator and ADR). The new compounds (modulators) are given i.p. or p.o. twice daily for three consecutive days starting on day 7 of tumor growth. ADR is administered i.v. ½ hour after the first injection on the second day of treatment tumor measurements, using vernier calipers, begin on day seven and continue 2 or 3 times per week for two weeks. On day 20–22 after initial injection the mice are sacrificed.

Human Tumor Xenograph

The tumor line MIP-4 is a human colon carcinoma which is intrisically resistant to Adriamycin. The cell line grows as a monolayer in 90% RPMI-1640 and 10% fetal bovine serum.

On day 0, mice are inoculated intramuscularly with 1.5×10$^6$ cells. The mice used are 4–6 weeks old athymic female nude mice obtained from Taconic or Charles River Laboratories. On day 7, the tumor bearing mice are randomized into groups of 5. In the MIP-4 model, for each experiment there is a tumor growth control group (receiving vehicle only), a negative control group (receiving Vinblastine [VBL] only) and a positive control group (receiving a known modulator and VBL). The remaining groups are used for testing modulators and VBL.

The modulators are given i.p. or p.o. once per day on days 6, 13, and 20 of tumor growth. VBL is administered i.v. 1 hour after modulator injection on all days of treatment. Tumor measurements are made on days 7 and 13, then, and continue 2 or 3 times per week. 30–35 days after initial injection the mice are sacrificed and the tumor bearing legs removed and weighted.

The efficacy of the modulators is determined by comparing the tumor growth of treated mice versus ADR only control mice. Tumor volumes are calculated from the tumor diameters using the formula for a ellipsoid volume (μl of tumor volume=L×W$^2$/2). Results are expressed as a percentage relative to the mean tumor volume for the ADR only control group.

$$\% \text{ tumor growth} = \frac{\text{mean tumor volume of treated}}{\text{mean tumor volume of } ADR \text{ only}} \times 100$$

In Vitro Tumor Models

ME180R cells were plated in 100 μl of DMEM media at a concentration of 5×10⁵ cells/ml and incubated overnight. Spent media was removed by blotting on day 2 and replaced with 100 μl of fresh media containig $1\times10^{-7}$M [³H] Vinblastine sulphate (8.3 Ci/mmol) and varying concentrations of modulator compounds ranging from $1\times10^{-5}$M to $1\times10^{-7}$M. Plates were incubated for 4–5 hours at 37° C., 5% $CO_2$. Plates were washed 5× with 100 μl PBS to remove free Vinblastine. Cells were trypsinized and harvested into 3 mls of scintillation fluid. Enhancement of drug accumulation in the presence of modulator was monitored via LSC.

The compounds of the present invention show good activity in the models described.

The compounds of the formula 1 can be administered together with or seperately from the cancerostatics. However, seperate prior administration, and seperate prior administration with subsequent simultaneous administration of a new compound plus cancerostatic is preferred. Administration may be any of the means which are conventional for pharmaceutical, preferably oncological agents, including oral and parenteral means such as subcutaneously, intravenously, intramuscularly and intraperitoneally. The compounds may be administered alone or in the form of pharmaceutical compositions containing a compound of formula 1 together with a pharmaceutically accepted carrier appropriate for the desired route of administration. Such pharmaceutical compositions may be combination products, i.e., may also contain other therapeutically active ingredients.

The dosage to be administered to the mammal will contain an effective resistance-modulating amount of active ingredient which will depend upon conventional factors including the biological activity of the particular compound employed; the means of administration; the age, health and body weight of the recipient; the nature and extent of the symptoms; the frequency of treatment; the administration of other therapies; and the effect desired. A typical daily dose will be about 5 to 1000 milligrams per kilogramm of body weight on oral administration and about 1 to 100 mg milligrams per kilogramm of body weight on parenteral administration.

The novel compounds can be administered alone or together with the cancerostatics in conventional solid or liquid pharmaceutical administration forms, eg. incoated or film-coated tablets, capsules, powders, granules, suppositories or solutions. These are produced in a conventional manner. The active substances can for this purpose be processed with conventional pharmaceutical aids such as tablet binders, fillers, preservatives, tablet disintegrants, flow regulators, plasticizers, wetting agents, dispersants, emulsifiers, solvents, sustained release compositions, antioxidants, and/or propellant gases (cf. H. Sucker et al in "Pharmazeutische Technologie", Thieme Verlag, Stuttgart, 1978). The administration forms obtained in this way normally contain up to 90% by weight of the active substances.

What we claim is:

1. A 1-amino-3-phenoxy-propane derivative of formula 1

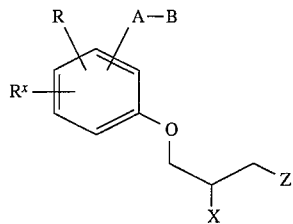

where
X is H or OH:
Z is selected from the group consisting of

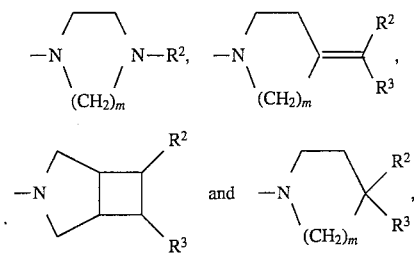

where
m is 2; and
$R^2$ and $R^3$ independently from each other are hydrogen or phenyl; with the proviso that $R^2$ and $R^3$ are not hydrogen at the same time; and wherein the phenyl moiety may be substituted by up to three members selected from the group consisting of linear or branched alkyl, alkoxy, halogen, nitro,

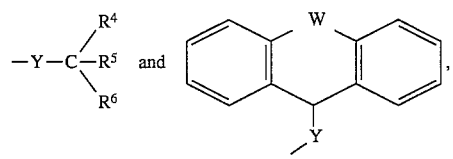

where
$R^4$ is hydrogen;
$R^5$ is hydrogen;
$R^6$ is cycloalky; or
$R^5$ and $R^6$ are each phenyl which may be substituted by a member selected from the group consisting of alkoxy, alkylenedioxy and halogen;
Y is a carbonyl- or a $(CH_2)_n$-moiety, where n is 0, 1 or 2; and
W is —CH=CH— or —$(CH_2)_p$—, where p is 2;
A is a member selected from the group consisting of

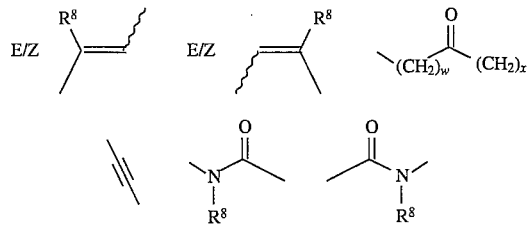

where
$R^8$ is hydrogen or linear or branched alkyl;

w and x are 0 or 1;

y and z independently from each other are 0 or 1;

B is a member selected from the group consisting of phenyl, pyridyl, furanyl, thienyl, oxazolyl, isoxazolyl and thiazolyl; with the proviso that B is not phenyl when A is $-O-CH_2-$; where B may be substituted by up to two members selected from the group consisting of linear or branched alkyl, alkoxy, methoxyalkyl, carbonylalkoxy, $CF_3$, halogen, pyrazolyl, 1,2,4-oxadiazolyl and 1,2,4-thiadiazolyl; where the substituents on B may be substituted by a member selected from the group consisting of methoxyalkyl, carbonylalkoxy, $CF_3$, halogen, phenyl and benzyl;

wherein the phenyl and benzyl resides may be independently substituted by up to two members selected from the group consisting of halogen, alkyl, alkoxy and $CF_3$; and R and $R^x$ are selected from the group consisting of hydrogen, linear or branched alkyl, alkoxy, halogen, nitro, $CF_3$ and NR'R"; where R' and R" are linear alkyl or a cyclic hydrocarbon, annellated to the phenyl moiety of formula 1 to form a naphthalene group.

2. A pharmaceutical composition for the potentiation of anticancer drugs, which comprises a pharmaceutically effective amount of a compound of formula 1 or pharmaceutically acceptable salts thereof as set forth in claim 1 together with a pharmaceutically acceptable carrier or diluent.

3. An antitumor composition comprising an effective amount of a chemotherapeutic agent and an effective amount of the compound of formula 1 as defined in claim 6.

4. A method of treating colon cancer, which comprises administering to a patient in need thereof an effective amount of the composition as defined in claim 1.

* * * * *

UNITED STATES PATENT AND TRADEMARK OFFICE
CERTIFICATE OF CORRECTION

PATENT NO. : 5,622,953
DATED : April 22, 1997
INVENTOR(S) : JANSSEN et al.

It is certified that error appears in the above-indentified patent and that said Letters Patent is hereby corrected as shown below:

Col. 100, claim 1, line 44, "cycloalky" should be --cycloalkyl--.

Signed and Sealed this

Eighth Day of July, 1997

Attest:

BRUCE LEHMAN

Attesting Officer      Commissioner of Patents and Trademarks